(12) United States Patent
Payne et al.

(10) Patent No.: US 8,524,705 B2
(45) Date of Patent: Sep. 3, 2013

(54) 2-OXO-2-(2-PHENYL-5,6,7,8-TETRAHYDRO-INDOLIZIN-3-YL)-ACETAMIDE DERIVATIVES AND RELATED COMPOUNDS AS ANTIFUNGAL AGENTS

(75) Inventors: Lloyd James Payne, Cheshire (GB); Robert Downham, New market (GB); Graham Edward Morris Sibley, Manchester (GB); Philip Edwards, Stockport (GB); Gareth Morse Davies, Macclesfield (GB)

(73) Assignee: F2G Limited British Body Corporate, Greater Manchester (GB)

( * ) Notice: Subject to any disclaimer, the term of this patent is extended or adjusted under 35 U.S.C. 154(b) by 519 days.

(21) Appl. No.: 12/601,284

(22) PCT Filed: May 21, 2008

(86) PCT No.: PCT/GB2008/001738
§ 371 (c)(1),
(2), (4) Date: Sep. 23, 2010

(87) PCT Pub. No.: WO2008/145963
PCT Pub. Date: Dec. 4, 2008

(65) Prior Publication Data
US 2011/0009390 A1    Jan. 13, 2011

(30) Foreign Application Priority Data
May 25, 2007  (GB) .................................. 0710121.5

(51) Int. Cl.
| A61K 31/437 | (2006.01) |
| A61K 31/496 | (2006.01) |
| A61K 31/551 | (2006.01) |
| A61K 31/5377 | (2006.01) |
| A01N 43/90 | (2006.01) |

(52) U.S. Cl.
USPC ... 514/218; 514/253.04; 514/299; 514/233.2; 546/112; 544/362; 544/121; 540/575

(58) Field of Classification Search
USPC ......... 514/218, 253.04, 299, 233.2; 546/112; 544/362, 121; 540/575
See application file for complete search history.

(56) References Cited

FOREIGN PATENT DOCUMENTS
| EP | 0 252 809 | 1/1988 |
| JP | 09-249669 | 9/1997 |
| WO | WO 02/098876 | 12/2002 |
| WO | WO 2006/123145 | 11/2006 |
| WO | WO 2008/062182 | 5/2008 |

OTHER PUBLICATIONS

Galbraith et al., Journal of the American Chemical Society (1961), 83, 453-8.*
Isham et al., Journal of clinical microbiology, (2006), vol. 44(12), pp. 4342-4344.*
Cardellini et al., "Indolizine derivatives with biological activity I: N'-substituted hydrazides of indolizine-2-carboxylic acid," *J Pharm Sci.*, 66(2):259-262, 1977.
Galbraith et al., "The formation of Cycl[3,2,2] azine derivatives via the reaction of pyrrocoline with dimethyl acetylenedicarboxylate," *Journal of the American Chemical Society*, 83:453-458, 1961.
Groll et al., "Trends in the postmortem epidemiology of invasive fungal infections at a university hospital," *J Infect.*, 33:23-32, 1996.
Ribaud et al., "Survival and prognostic factors of invasive aspergillosis after allogeneic bone marrow transplantation," *Clin. Infect. Dis.*, 28:322-330, 1999.
Savage et al., "Efficient synthesis of 4-, 5-, and 6-methyl-2,2'-bipyridine by a negishi cross-coupling strategy followed by high-yield conversion to bromo- and chloromethyl-2,2'-bipyridines," *J. Org. Chem.*, 63:10048-10051, 1998.

* cited by examiner

*Primary Examiner* — Niloofar Rahmani
(74) *Attorney, Agent, or Firm* — Fulbright & Jaworski L.L.P.

(57) ABSTRACT

The invention provides compounds of formula (I), and pharmaceutically and agriculturally acceptable salts thereof: wherein: R1, R2, R3, R4, R5, R6, R7, R8, A1, L1 and n are as defined herein. These compounds and their pharmaceutically acceptable salts are useful in the manufacture of medicaments for use in the prevention or treatment of a fungal disease. Compounds of formula (I), and agriculturally acceptable salts thereof, may also be used as agricultural fungicides.

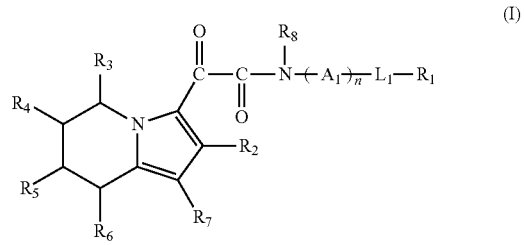

16 Claims, No Drawings

2-OXO-2-(2-PHENYL-5,6,7,8-TETRAHYDRO-INDOLIZIN-3-YL)-ACETAMIDE DERIVATIVES AND RELATED COMPOUNDS AS ANTIFUNGAL AGENTS

CROSS-REFERENCE TO RELATED APPLICATIONS

This is a U.S. national stage application, under 35 U.S.C. §371, of international application PCT/GB2008/001738, filed on May. 21, 2008, and claims priority to United Kingdom patent application number 0710121.5, filed May. 25, 2007.

FIELD OF THE INVENTION

This invention relates to tetrahydroindolizine compounds and their therapeutic use in prevention or treatment of fungal diseases. It also relates to the use of the compounds as agricultural fungicides.

BACKGROUND OF THE INVENTION

Invasive fungal infections are well recognised as diseases of the immunocompromised host. Over the last twenty years there have been significant rises in the number of recorded instances of fungal infection (Groll et al., 1996. *J Infect* 33, 23-32). In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic haemopoetic stem cell transplant recipients is as high as 15% (Ribaud et al., 1999, *Clin Infect Dis.* 28:322-30).

Currently only four classes of antifungal drug are available to treat systemic fungal infections. These are the polyenes (e.g., amphotericin B), the azoles (e.g., ketoconazole or itraconazole), the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14α-demethylase via a cytochrome P450-dependent mechanism. This leads to a depletion of the membrane sterol ergosterol and the accumulation of sterol precursors resulting in a plasma membrane with altered fluidity and structure.

Echinocandins work by the inhibition of the cell wall synthetic enzyme β-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucyotosine limits its therapeutic use.

It can be seen that to date the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases, resistance by fungi will inevitably occur.

The identification of new classes of antifungal agent is required to give the promise of positive therapeutic outcomes to patients.

SUMMARY OF THE INVENTION

The present inventors have found that certain tetrahydroindolizine compounds are antifungal. In particular, the compounds inhibit the growth of human pathogenic fungi such as *Aspergillus* and therefore may be used to treat fungal infection and disease.

Accordingly, the present invention provides a tetrahydroindolizinyl derivative of formula (I) or a pharmaceutically or agriculturally acceptable salt thereof:

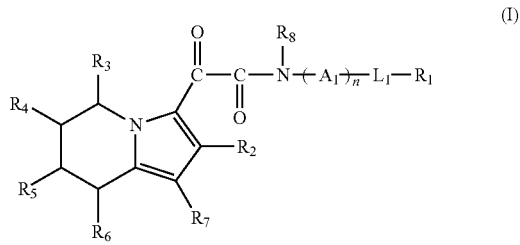

wherein:

R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2 or -A2-L3-A3;

A1, A2 and A3 are the same or different and represent C3-C6 cycloalkyl or an unsubstituted or substituted C6-C10 aryl or 5- to 12-membered heterocyclyl group;

L1 represents a bond, a C1-C6 alkylene group in which none, one, two or three —CH$_2$— groups are independently replaced by —O—, —S— or —NR'—, or a 5- to 12-membered heterocyclyl group;

L2 represents —NR'—, —O—, —CO—, —OCO—, —OCONR'R"—, —CONR'R"— or —SO$_2$—;

L3 represents a bond or a C1-C4 alkylene group in which none, one or two —CH$_2$— groups are independently replaced by —O—, —S— or —NR'—;

n represents 0 or 1;

R8 represents hydrogen or C1-C4 alkyl;

R2 represents an unsubstituted or substituted group selected from C6-C10 aryl, a 5- to 12-membered heterocyclyl group, C1-C8 alkyl and C3-C6 cycloalkyl, halogen or a group of formula —B1-B2;

B1 represents an unsubstituted or substituted C6-C10 aryl group;

B2 represents an unsubstituted or substituted C6-C10 aryl or 5- to 12-membered heterocyclyl group;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, C1-C8 alkyl, C2-C8 alkenyl, C2-C8 alkynyl, halogen, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R";

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13—C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and R' and R" independently represent hydrogen, C1-C8 alkyl, C2-C8 alkenyl or C2-C8 alkynyl.

The invention also provides a derivative or pharmaceutically acceptable salt as defined above for use in a method of treatment of the human or animal body. Also provided is the use of a derivative or pharmaceutically acceptable salt as defined above for the manufacture of a medicament for the prevention or treatment of a fungal disease. The invention further provides a pharmaceutical composition comprising a derivative or pharmaceutically acceptable salt as defined above and a pharmaceutically acceptable carrier or diluent, as well as a composition comprising a derivative or agriculturally acceptable salt as defined above and an agriculturally acceptable carrier or diluent.

The invention also provides an agent for the treatment of a fungal disease comprising a derivative or pharmaceutically acceptable salt as defined above. There is further provided a method of treating a subject suffering from or susceptible to a fungal disease, which method comprises administering to said subject an effective amount of a derivative or pharmaceutically acceptable salt as defined above, as well as a method of controlling a fungal disease in a plant, which method comprises applying to the locus of the plant a derivative or agriculturally acceptable salt as defined above. The invention also provides the use of a derivative or agriculturally acceptable salt as defined above as an agricultural fungicide.

DETAILED DESCRIPTION OF THE INVENTION

As used herein, a C1-C8 alkyl group or moiety can be linear, branched or cyclic but is preferably linear. It is preferably a C1-C6 alkyl group, more preferably a C1-C4 alkyl group, most preferably a C1-C3 alkyl group. Suitable such alkyl groups and moieties include methyl, ethyl, n-propyl, i-propyl, n-butyl, sec-butyl and tert-butyl, as well as pentyl, e.g. CH$_2$C(CH$_3$)$_3$, hexyl, heptyl and octyl and isomers thereof. As used herein, a C1-C8 alkylene group or moiety is a divalent alkyl group or moiety as defined above.

As used herein, a C2-C8 alkenyl group or moiety can be linear, branched or cyclic but is preferably linear. It contains one or more carbon-carbon double bonds. It is preferably a C2-C6 alkenyl group, more preferably a C2-C4 alkenyl group, most preferably a C2-C3 alkenyl group. Suitable such alkenyl groups and moieties include vinyl, allyl, propenyl, butenyl, e.g. CH$_2$C(Me)=CH$_2$, pentenyl, hexenyl, heptenyl and octenyl and isomers thereof.

As used herein, a C2-C8 alkynyl group or moiety can be linear or branched but is preferably linear. It contains one or more carbon-carbon triple bonds. It is preferably a C2-C6 alkynyl group, more preferably a C2-C4 alkynyl group, most preferably a C2-C3 alkynyl group. Suitable such alkynyl groups and moieties include ethynyl, propynyl, butynyl, pentynyl, hexynyl, heptynyl and octynyl and isomers thereof.

An alkyl, alkenyl or alkynyl group or moiety can be substituted or unsubstituted. Typically, it carries up to three substituents, e.g. one or two substituents. Suitable substituents are preferably themselves unsubstituted and include halogen such as fluorine, hydroxy, amino, (C1-C4 alkyl)amino, di(C1-C4 alkyl)amino, C1-C4 alkoxy such as methoxy or ethoxy, —CO$_2$H and —CO$_2$(C1-C4 alkyl). Examples of these substituents include unsubstituted substituents such as halogen (for example fluorine), hydroxy, amino, (C1-C4 alkyl)amino, di(C1-C4 alkyl)amino and C1-C4 alkoxy such as methoxy or ethoxy. C1-C4 alkoxy, such as methoxy, and halogen, such as fluorine, are preferred.

As used herein, a C3-C6 cycloalkyl group is typically a C5 or C6 cycloalkyl group. Typically a cycloalkyl group is unsubstituted or substituted with up to three substituents, e.g. one or two substituents. Suitable substituents include C1-C8 alkyl, C2-C8 alkenyl, C2-C8 alkynyl, Z and —Y—Z wherein Y and Z are as hereinbefore defined. Where present, preferably the substituents are themselves unsubstituted. Typically, a cycloalkyl group is unsubstituted.

When Y is C1-C8 alkylene, it is preferably C1-C4 alkylene, more preferably methylene or ethylene.

When Y is C2-C8 alkenylene, it is preferably C2-C4 alkenylene, more preferably ethenylene.

When Y is C2-C8 alkynylene, it is preferably C2-C4 alkynylene, more preferably ethynylene.

When R' or R" is C1-C8 alkyl, it is preferably C1-C4 alkyl, more preferably methyl or ethyl.

When R' or R" is C2-C8 alkenyl, it is preferably C2-C4 alkenyl, more preferably ethenyl.

When R' or R" is C2-C8 alkynyl, it is preferably C2-C4 alkynyl, more preferably ethynyl.

As used herein, an aryl group or moiety is typically phenyl or naphthyl, more preferably phenyl.

As used herein and unless otherwise stated, a heterocyclyl group or moiety is a saturated or unsaturated, 5- to 12-membered ring system in which the ring contains at least one heteroatom. Typically, the ring contains up to three or four heteroatoms, e.g. one or two heteroatoms, selected from O, S and N. Thus, a heterocyclyl group or moiety is typically a 5- to 12-membered ring containing one, two or three heteroatoms selected from O, S and N. Suitable such heterocyclyl groups and moieties include, for example, monocyclic saturated 5- to 8-membered rings, more preferably 5- to 6-membered rings, such as tetrahydrofuranyl, piperidinyl, oxazolidinyl, morpholinyl, thiomorpholinyl, pyrrolidinyl, dioxolanyl, piperidonyl, azepanyl, piperazinyl, tetrahydropyranyl and 1,4-diazepanyl, more preferably morpholinyl, piperazinyl, tetrahydropyranyl, piperidinyl and 1,4-diazepanyl; monocyclic at least partially unsaturated 5- to 8-membered rings, more preferably 5- to 6-membered rings, such as furanyl, pyrrolyl, thiophenyl, oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, e.g. oxazolyl, imidazolyl, furanyl, thiophenyl, pyrimidinyl or pyridinyl, more preferably furanyl, thiophenyl, pyrimidinyl or pyridinyl; bicyclic 8- to 10-membered ring systems such as indolyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, cirmolinyl, purinyl and cyclopentapyridines which may optionally be partially unsaturated, for example dihydroindolyl and dihydrobenzofuranyl; and tricyclic 11- or 12-membered ring systems such as acridinyl, pteridinyl and benzathiazinyl. Particular examples of such heterocyclyl groups and moieties include monocyclic saturated 5- to 8-membered rings, more preferably monocyclic saturated 5- to 6-membered rings such as morpholinyl, piperazinyl, tetrahydropyranyl, piperidinyl and 1,4-diazepanyl; monocyclic at least partially unsaturated 5- to 8-membered rings, more preferably monocyclic unsaturated 5- to 6-membered rings such as pyrimidinyl and pyridinyl.

A heterocyclyl or aryl group or moiety may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl or aryl group or moiety carries up to three substituents, e.g. one or two substituents. The heterocycle may be connected to the remainder of the molecule by a bond to any of its available ring positions.

Suitable substituents include C1-C8 alkyl, C2-C8 alkenyl, C2-C8 alkynyl, Z, —Y—Z, —Y—X—Z and —Y—X-A4 wherein Y and Z are as hereinbefore defined, X represents —O—(C1-C8 alkylene)- and A4 represents a C3-C6 cycloalkyl or C6-C10 aryl group. Where groups of formula —Y—X—Z or —Y—X-A4 are present they are preferably present as substituents on the A1 moiety only. Furthermore, where groups of formula —Y—X—Z or —Y—X-A4 are present then preferably only one such group is present on any one heterocyclyl or aryl group or moiety. In one embodiment preferred substituents include C1-C8 alkyl, C2-C8 alkenyl, C2-C8 alkynyl, Z and —Y—Z wherein Y and Z are as hereinbefore defined.

When substituents are of formula —Y—Z, —Y—X—Z or —Y—X-A4, preferably Y is an unsubstituted C1-C8 alkylene group, more preferably an unsubstituted methylene group.

When substituents are of formula —Y—Z, —Y—X—Z or —Y—X-A4, preferably X is a —O—(C2-C3 alkylene) group. When substituents are of formula —Y—Z, —Y—X—Z or —Y—X-A4, preferably Z is —OR' or —NR'R" where R' and R" independently represent hydrogen or C1-C2 alkyl, more preferably where R' and R" are both methyl. When substituents are of formula —Y—Z, —Y—X—Z or —Y—X-A4, preferably A4 is a 5- or 6-membered heterocyclyl group which is unsubstituted or substituted by one C1-C2 alkyl group. More preferably A4 is morpholinyl or piperazinyl, which groups are preferably unsubstituted or substituted with one methyl group.

Preferred substituents on an aryl or heterocyclyl group or moiety are unsubstituted substituents selected from halogen, —CO₂R', —CONR'R", OCOR', hydroxyl, cyano, —NR'R", —COR', —NSO₂R', —O(C2-C4 alkenyl), C2-C4 alkenyl, —SO₂R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino and C1-C4 alkoxy, preferably C1-C4 alkoxy, or groups of formula —Y—Z, —Y—X—Z or —Y—X-A4 where X, Y, Z and A4 are as defined above. Preferred substituents on an aryl or heterocyclyl group or moiety are unsubstituted substituents selected from halogen, —CO₂R', —CONR'R", OCOR', hydroxyl, cyano, —NR'R", —COR', —NSO₂R', —O(C2-C4 alkenyl), C2-C4 alkenyl, —SO₂R', —OCONR'R" and —CR'=NOR", or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino and C1-C4 alkoxy, preferably C1-C4 alkoxy.

In one embodiment examples of more preferred substituents on an aryl or heterocyclyl group or moiety are unsubstituted substituents selected from halogen, C1-C6 alkyl, —CO₂R', —CONR'R", —OCOR', hydroxyl and cyano, wherein R' and R" are independently selected from hydrogen and C1-C4 alkyl, or unsubstituted C1-C4 alkoxy or C1-C4 alkoxy substituted with a further unsubstituted C1-C4 alkoxy group, or groups of formula —Y—Z, —Y—X—Z or —Y—X-A4 where Y represents unsubstituted C1-C8 alkylene, X represents an unsubstituted group —O—(C1-C8 alkylene)-, Z represents a group —OR' or —NR'R" where R' and R" represent hydrogen or unsubstituted C1-C2 alkyl, and A4 represents a 5- to 6-membered heterocyclyl group or moiety. Typically none or one cyano substituent is present. Examples of more preferred substituents on an aryl or heterocyclyl group or moiety are unsubstituted substituents selected from halogen, C1-C6 alkyl, —CO₂R', —CONR'R", —OCOR', hydroxyl and cyano, wherein R' and R" are independently selected from hydrogen and C1-C4 alkyl, or unsubstituted C1-C4 alkoxy or C1-C4 alkoxy substituted with a further unsubstituted C1-C4 alkoxy group. Typically none or one cyano substituent is present.

Most preferable substituents include C1-C6 alkyl (for example methyl) or C1-C4 alkoxy substituted with 1 or 2 C1-C4 alkoxy groups (for example —OCH₂CH₂OCH₃). Most preferred substituents on the A1 group also include groups of formula —Y—Z, —Y—X—Z or —Y—X-A4 where Y represents unsubstituted C1-C8 alkylene, X represents an unsubstituted group —O—(C1-C8 alkylene)-, Z represents a group —OR' or —NR'R" where R' and R" represent hydrogen or unsubstituted C1-C2 alkyl, and A4 represents a 5- to 6-membered heterocyclyl group or moiety. Preferably Y is an unsubstituted C1-C8 alkylene group, more preferably an unsubstituted methylene group. Preferably X is a —O—(C2-C3 alkylene) group. Preferably Z is —OR' or —NR'R" where R' and R" independently represent hydrogen or C1-C2 alkyl, more preferably where R' and R" are both methyl. Preferably A4 is a 5- or 6-membered heterocyclyl group which is unsubstituted or substituted by one C1-C2 alkyl group. More preferably A4 is morpholinyl or piperazinyl, which groups are preferably unsubstituted or substituted with one methyl group.

A heterocyclyl group may also be substituted with >C=O, >SO₂, >C=NOR', >C—CH₂ or —OCH₂CH₂O— such that one or two ring atoms are replaced with the >C=O, >SO₂, >C=NOR', >C=CH₂ or —OCH₂CH₂O— group. R' in this embodiment is typically hydrogen or C1-C4 alkyl.

As used herein, a halogen is typically chlorine, fluorine, bromine or iodine, and is preferably chlorine, fluorine or bromine, more preferably chlorine or fluorine.

In one embodiment of the invention, n=0 and the group -L1—R1 represents hydrogen, C1-C8 alkyl, C2-C8 alkenyl, C2-C8 alkynyl, —COR', wherein R' represents hydrogen or C1-C4 alkyl, C6-C10 aryl, a 5- to 12-membered heterocyclyl group, C3-C6 cycloalkyl, (C1-C4 alkylene)-C6-C10 aryl or (C1-C4 alkylene) -5- to 12-membered heterocyclyl. In this embodiment, aryl and heterocyclyl groups may be unsubstituted or substituted with one, two or three unsubstituted groups selected from C1-C4 alkyl, C1-C4 alkoxy, halogen, —CO₂R', —CONR'R", —OCOR', hydroxyl, cyano, —NR'R", —COR', NSO₂R', —O(C2-C4 alkenyl), C2-C4 alkenyl, —SO₂R', —OCONR'R" and —CR'=NOR", wherein R' and R" are independently hydrogen or C1-C4 alkyl. Preferred substituents are C1-C4 alkyl, C1-C4 alkoxy and halogen. In this embodiment, the group -L1—R1 is preferably unsubstituted.

In another embodiment, n=0 and L1 represents a C1-C6 alkylene group in which none, one, two or three —$CH_2$— groups are independently replaced by —O—, —S— or —NR'—, where R' is hydrogen or unsubstituted C1-C4 alkyl. In this embodiment preferably L1 represents a C3-C4 alkylene group in which one or two more preferably two, —$CH_2$— groups are independently replaced by —O—, —S— or —NR'—. Preferred L1 groups include —O—$CH_2$—$CH_2$—O—.

In another embodiment, n=0 and L1 represents a 5- to 7-membered heterocyclyl group.

In another embodiment, n=1 and A1 represents phenyl or a 5- or 6-membered heterocyclyl group. Preferably A1 represents phenyl, pyridyl or piperidinyl. More preferably A1 represents phenyl or pyridyl. A1 may be unsubstituted or substituted with one, two or three unsubstituted groups selected from C1-C4 alkyl, C1-C4 alkoxy, halogen, —$CO_2R'$, —CONR'R", —OCOR', hydroxyl, cyano, —NR'R", —COR', $NSO_2R'$, —O(C2-C4 alkenyl), —C2-C4 alkenyl, —$SO_2R'$, —OCONR'R" and —CR'═NOR", wherein R' and R" are independently hydrogen or C1-C4 alkyl. Typically only one cyano group is present. Preferred substituents are C1-C4 alkyl, C1-C4 alkoxy and halogen. Preferably A1 is unsubstituted. A1 may also be substituted with a group of formula —Y—Z, —Y—X—Z or —Y—X-A4 where X, Y, Z and A4 are as defined above. When a substituent of formula —Y—Z, —Y—X—Z or —Y—X-A4 is present, preferably there are no other substituents.

When n=1, L1 preferably represents a bond, a 5- to 7-membered heterocyclyl group, a group of formula —$(CH_2)_3$-Het- or a group of formula -Het-$(CH_2)_2$-Het-, wherein each Het may be the same or different and represents —O— or —NR'—, wherein R' is hydrogen or C1-C4 alkyl.

When L1 represents a 5- to 7-membered heterocyclyl group, it may be linked to A1 and R1 via a carbon atom or a heteroatom. Preferred 5- to 7-membered heterocyclyl groups are saturated groups which contains at least two nitrogen atoms, wherein the heterocyclyl group is linked to both A1 and R1 via a nitrogen atom. Examples of suitable heterocycles for L1 include piperazinyl and 1,4-diazepanyl. Other suitable heterocyclyl groups include piperidinyl. When L1 represents a 5- to 7-membered heterocyclyl group, it can be unsubstituted or substituted. If it is substituted, the substituent can be present on an atom connecting L1 to R1 or to the rest of the molecule (i.e. to the —NR8- group). For example, when L1 is piperidinyl attached to the —NR8- group by the carbon atom para to the nitrogen atom in the piperidine ring, this carbon atom can also bear a substituent such as a hydroxyl group. When L1 represents a 5- to 7-membered heterocyclyl group it is typically unsubstituted.

When n=1, L1 is most preferably an unsubstituted, saturated 5- to 7-membered heterocyclyl group containing at least two nitrogen atoms, a group of formula —$(CH_2)_{m+1}$-Het- or a group of formula -Het-$(CH_2)_m$-Het-, wherein m represents 1, 2, 3 or 4, preferably 2 or 3, and each Het may be the same or different and represents —O— or —NR'—, wherein R' is hydrogen or unsubstituted C1-C4 alkyl.

When n=1 and L1 is a bond, R1 preferably represents L2-A2. When n=1 and L1 is other than a bond, R1 is preferably a C1-C6 alkyl group, a C2-C6 alkenyl group, a C2-C6 alkynyl group, unsubstituted —$SO_2$(C1-C4 alkyl) or a group -A2L2-A2, -L3-A2 or -A2-L3-A3. The alkyl, alkenyl and alkynyl groups are unsubstituted or substituted with 1, 2 or 3 substituents selected from halogen (e.g. fluorine), hydroxyl, amino, C1-C4 alkoxy, $CO_2H$ and $CO_2$(C1-C4 alkyl). Halogen, e.g. fluorine, is preferred. The substituents are themselves unsubstituted.

A2 preferably represents C3-C6 cycloalkyl, phenyl or a 5- to 12-membered heterocyclyl group. Preferred heterocyclyl groups include monocyclic, unsaturated 5- to 6-membered rings, each of which may contain one, two or three, e.g. one or two, heteroatoms selected from N, O and S. Unsaturated 5- or 6-membered rings are preferred, e.g. pyridinyl, pyrimidinyl, thienyl and furanyl. Other preferred A2 groups include bicyclic 8- to 10-membered ring systems and naphthyl groups. Preferred bicyclic 8- to 10-membered ring include dihydrobenzofuranyl. In one embodiment preferably A2 is phenyl.

A2 may be unsubstituted or substituted by one, two or three substituents. Examples of suitable substituents are unsubstituted groups selected from C1-C4 alkyl, halogen, —$CO_2R'$, —CONR'R", —OCOR', hydroxyl, cyano, —NR'R", —COR', —$NSO_2R'$, —O(C2-C4 alkenyl), —C2-C4 alkenyl, —$SO_2R'$, —OCONR'R" and —CR'═NOR", wherein R' and R" are independently hydrogen or C1-C4 alkyl, or unsubstituted C1-C4 alkoxy or C1-C4 alkoxy substituted with one or two unsubstituted C1-C4 alkoxy groups. Typically only one cyano group is present. Preferred substituents are unsubstituted C1-C4 alkyl, halogen, unsubstituted C1-C4 alkoxy or C1-C4 alkoxy substituted with —OMe or —OEt. Methyl, ethyl, unsubstituted C1-C4 alkoxy and C1-C4 alkoxy substituted with —OMe are preferred substituents, with methyl and C1-C4 alkoxy substituted with —OMe being particularly preferred.

In one embodiment, L2 represents —$SO_2$—.

In one embodiment, L3 represents a bond or a C1-C4 alkylene group in which none, one or two —$CH_2$— moieties are independently replaced with —O— or —NR'— wherein R' represents hydrogen or unsubstituted C1-C4 alkyl. In another embodiment, L3 represents a bond or an unsubstituted C1-C4 alkylene group. Preferably, L3 represents a bond or unsubstituted methylene or ethylene, more preferably unsubstituted methylene. In the group -L3-A2, L3 preferably represents unsubstituted methylene or ethylene, more preferably unsubstituted methylene.

In one embodiment, A3 represents phenyl or a 5- to 12-membered heterocyclyl group. Preferred heterocyclyl groups include monocyclic, saturated 5- to 6-membered rings, each of which may contain one, two or three, e.g. one or two, heteroatoms selected from N, O and S. Saturated 5- or 6-membered rings are preferred, e.g. morpholinyl, tetrahydropyranyl, piperidinyl or piperazinyl, in particular morpholinyl.

A3 may be unsubstituted or substituted by one, two or three unsubstituted groups selected from C1-C4 alkyl, C1-C4 alkoxy, halogen, —$CO_2R'$, —CONR'R", —OCOR', hydroxyl, cyano, —NR'R", —COR', —$NSO_2R'$, —O(C2-C4 alkenyl), —C2-C4 alkenyl, —$SO_2R'$, —OCONR'R" and —CR'═NOR", wherein R' and R" are independently hydrogen or C1-C4 alkyl. Typically only one cyano group is present.

Preferred substituents are C1-C4 alkyl, C1-C4 alkoxy and halogen. Most preferably A3 is unsubstituted.

In one embodiment, where R1 is -A2-L3-A3 preferably A2 is pyridinyl, L3 is unsubstituted methylene and A3 is morpholinyl.

In one embodiment, R8 is hydrogen or methyl, more preferably R8 is hydrogen.

In one embodiment, R2 is halogen or an unsubstituted or substituted group selected from C6-C10 aryl, a 5- to 12-membered heterocyclyl group, C1-C8 alkyl, and C3-C6 cycloalkyl. R2 is preferably phenyl, C1-C4 alkyl, C3-C6 cycloalkyl or a 5- or 6-membered heterocycle. The phenyl and heterocyclyl groups are unsubstituted or substituted with one, two or three unsubstituted substituents selected from halogen, C1-C4 alkyl, C1-C4 alkoxy, —CO₂R', —CONR'R", —OCOR' or cyano, wherein R' and R" are independently selected from hydrogen and unsubstituted C1-C4 alkyl. Typically only one cyano substituent is present. Preferred substituents are halogen, C1-C4 alkyl and C1-C4 alkoxy. More preferably R2 is unsubstituted phenyl, unsubstituted C1-C4 alkyl, unsubstituted C5 or C6 cycloalkyl, unsubstituted tetrahydropyranyl or N-methyl-piperidinyl. Most preferably R2 is unsubstituted phenyl.

Typically, when R3, R4, R5 or R6 is aryl, heterocyclyl, —(C1-C4 alkylene)-aryl or (C1-C4 alkylene)-heteroaryl, it is phenyl, benzyl or pyridyl. Typically, none, one or two, preferably none or one, of R3, R4, R5 and R6 is aryl, heterocyclyl, —(C1-C4 alkylene)-aryl or (C1-C4 alkylene)-heterocyclyl. R3, R4, R5 and R6 are typically unsubstituted.

In one embodiment, R3, R4, R5 and R6 independently represent hydrogen, C1-C8 alkyl, C2-C8 alkenyl, C2-C8 alkynyl, halogen, C3-C6 cycloalkyl, —OR', —SR', —SOR', —SO₂R', —SO₂NR'R", —SO₃H, —NR'R", —NR'COR', —CO₂R', —CONR'R", —COR', —OCOR', —CF₃, —NSO₂R' or —OCONR'R", wherein R' and R" are independently hydrogen or C1-C4 alkyl. In another embodiment, R3, R4, R5 and R6 independently represent hydrogen, halogen, C1-C4 alkyl, or C1-C4 alkoxy, e.g. hydrogen, halogen or C1-C4 alkyl. Preferably, R3, R4, R5 and R6 each represent hydrogen.

Typically, when R7 is or contains an aryl or heterocyclyl group, the aryl or heterocyclyl group is phenyl, benzyl or pyridyl.

In one embodiment, R7 represents hydrogen, halogen, C1-C4 alkyl, C2-C4 alkenyl, C2-C4 alkynyl, —OR', —CO₂R', CONR'R", —COR', —CN, —NO₂, —NR'R" or —CF₃ wherein R' and R" are independently hydrogen or C1-C4 alkyl. In another embodiment R7 represents hydrogen, halogen or C1-C4 alkyl, preferably hydrogen. Where R7 is capable of being substituted, it is typically unsubstituted.

Typically, Z is halogen, OR', SR', —NR'R', —CO₂R', —CONR'R", —COR', —OCOR' or CN, wherein R' and R" are independently hydrogen or C1-C4 alkyl.

In a preferred embodiment of the invention, n=1 and A1 represents phenyl, pyridyl or piperidinyl;

R1 is a C1-C6 alkyl, C2-C6 alkenyl or C2-C6 alkynyl group which is unsubstituted or substituted with 1, 2 or 3 substituents selected from halogen (e.g. fluorine), hydroxyl, amino, C1-C4 alkoxy, CO₂H and CO₂(C1-C4 alkyl); unsubstituted —SO₂(C1-C4 alkyl); or a group -A2, -L2-A2, -L3-A2 or -A2-L3-A3;

A2 is unsubstituted C3-C6 cycloalkyl, phenyl or a monocyclic, saturated or unsaturated 5- or 6-membered heterocyclyl group;

A3 is phenyl or a monocyclic, saturated or unsaturated, 5- or 6-membered heterocyclyl group;

L1 is a bond, an unsubstituted 5- to 7-membered heterocyclyl group, a group of formula —(CH₂)ₘ₊₁-Het- or a group of formula -Het-(CH₂)ₘ-Het-, wherein m is 1, 2, 3 or 4 and each Het may be the same or different and represents —O— or —NR'—, wherein R' is hydrogen or unsubstituted C1-C4 alkyl;

L2 is as defined above;

L3 represents a bond or a C1-C4 alkylene group in which none, one or two —CH₂— groups are independently replaced by —O— or —NR'—, wherein R' represents hydrogen or unsubstituted C1-C4 alkyl;

R8 is hydrogen or methyl;

R2 is phenyl, C1-C4 alkyl, C3-C6 cycloalkyl or a 5- or 6-membered heterocyclyl group, each of which is unsubstituted or substituted with one, two or three unsubstituted substituents selected from halogen, C1-C4 alkyl, C1-C4 alkoxy, —CO₂R', —CONR'R", —OCOR' or cyano, wherein R' and R" are independently selected from hydrogen and unsubstituted C1-C4 alkyl;

R3, R4, R5 and R6 are unsubstituted and each independently represents hydrogen, C1-C8 alkyl, C2-C8 alkenyl, C2-C8 alkynyl, halogen, C3-C6 cycloalkyl, —OR', —SR', —SOR', —SO₂R', —SO₂NR'R", —SO₃H, —NR'R", —NR'COR', —CO₂R', —CONR'R", —COR', —OCOR', —CF₃, —NSO₂R' or —OCONR'R", wherein R' and R" are independently hydrogen or C1-C4 alkyl; and R7 is an unsubstituted group selected from hydrogen, halogen, C1-C4 alkyl, C2-C4 alkenyl, C2-C4 alkynyl, —OR', —CO₂R', CONR'R", —COR', —CN, —NO₂, —NR'R" and —CF₃ wherein R' and R" are independently hydrogen or C1-C4 alkyl;

wherein the aryl and heterocyclyl groups A1, A2 and A3 are unsubstituted or substituted with one, two or three unsubstituted substituents selected from halogen, —CO₂R', —CONR'R", OCOR', hydroxyl, cyano, —NR'R", —COR', —NSO₂R', —O(C2-C4 alkenyl), C2-C4 alkenyl, —SO₂R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy, cyano, —COR' and —CO₂R', wherein R' and R" are independently selected from hydrogen and C1-C4 alkyl. In this embodiment the aryl and heterocyclyl groups A1, A2 and A3 can also or alternatively be substituted by one, two or three, more preferably by one, substituent of formula —Y—Z, —Y—X—Z or —Y—X-A4 where X, Y, Z and A4 are as defined earlier.

In an alternative embodiment, the tetrahydroindolizinyl derivative is of formula (Ia):

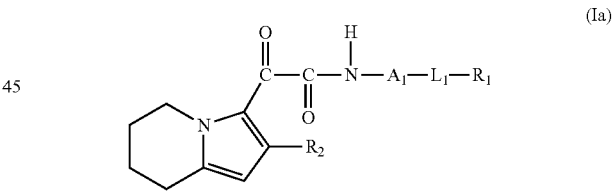

(Ia)

wherein:
R1 is a C1-C6 alkyl, C2-C6 alkenyl or C2-C6 alkynyl group which is unsubstituted or substituted with 1, 2 or 3 halogen atoms; unsubstituted —SO₂(C1-C4 alkyl); or a group -A2, -L2-A2, -L3-A2 or -A2-L3-A3;

A1 is unsubstituted phenyl or pyridyl;

A2 is unsubstituted C3-C6 cycloalkyl, or a phenyl, or monocyclic, saturated or unsaturated, 5- or 6-membered heterocyclyl group which is unsubstituted or substituted with one, two or three substituents selected from halogen, unsubstituted C1-C4 alkyl, unsubstituted C1-C4 alkoxy or C1-C4 alkoxy which is substituted with —OMe or —OEt;

A3 is phenyl or a monocyclic, saturated or unsaturated, 5- or 6-membered heterocyclyl group which is unsubstituted or substituted with one, two or three substituents selected from halogen, unsubstituted C1-C4 alkyl and unsubstituted C1-C4 alkoxy;

L1 is an unsubstituted, saturated 5- to 7-membered heterocyclyl group containing at least two nitrogen atoms, a group of formula —(CH$_2$)$_{m+1}$-Het- or a group of formula -Het-(CH$_2$)$_m$-Het-, wherein m is 2 or 3 and each Het may be the same or different and represents —O— or —NR'—, wherein R' is hydrogen or C1-C4 alkyl;

L2 is —SO$_2$—;

L3 is unsubstituted methylene; and

R2 is unsubstituted C1-C4 alkyl, unsubstituted phenyl, unsubstituted C5 or C6 cycloalkyl, unsubstituted tetrahydropyranyl or N-methyl-piperidinyl. In another embodiment the tetrahydroindolizinyl derivative is of formula (Ia) above but A1 is substituted by one, two or three, more preferably one, group of formula —Y—Z, —Y—X—Z or —Y—X-A4 where X, Y, Z and A4 are as defined earlier.

Specific examples of compounds of formula (I) include:

N-{4-[2-(4,6-Dimethyl-pyridin-2-yloxy)-ethoxy]-phenyl}-2-oxo-2-(2-phenyl-5,6,7,8-tetrahydro-indolizin-3-yl)-acetamide;

N-{4-[4-(4-Methoxy-6-methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-(2-isopropyl-5,6,7,8-tetrahydro-indolizin-3-yl)-2-oxo-acetamide;

2-(2-Cyclohexyl-5,6,7,8-tetrahydro-indolizin-3-yl)-N-{4-[4-(4,6-dimethyl-pyridin-2-yl)-piperazin-1-yl]-phenyl}-2-oxo-acetamide;

2-Oxo-2-(2-phenyl-5,6,7,8-tetrahydro-indolizin-3-yl)-N-[4-(4-pyridin-3-yl-piperazin-1-yl)-phenyl]-acetamide;

2-Oxo-2-(2-phenyl-5,6,7,8-tetrahydro-indolizin-3-yl)-N-{4-[2-(pyridin-2-yloxy)-ethylamino]-phenyl}-acetamide;

N-(4-{4-[4-(2-Methoxy-ethoxy)-6-methyl-pyridin-2-yl]piperazin-1-yl}-phenyl)-2-oxo-2-(2-phenyl-5,6,7,8-tetrahydro-indolizin-3-yl)-acetamide;

N-[4-({2-[(4,6-Dimethyl-pyridin-2-yl)-methyl-amino]-ethyl}-methyl-amino)-phenyl]-2-oxo-2-(2-phenyl-5,6,7,8-tetrahydro-indolizin-3-yl)-acetamide;

N-{5-[4-(2,2-Dimethyl-propyl)-piperazin-1-yl]-pyridin-2-yl}-2-oxo-2-(2-phenyl-5,6,7,8-tetrahydro-indolizin-3-yl)-acetamide;

N-{4-[4-(4-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(6-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyrimidin-2-yl)-piperazin-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-{4-[4-(3,3,3-trifluoro-propyl)-piperazin-1-yl]-phenyl}-acetamide;

N-{6-[4-(2,2-Dimethyl-propyl)-piperazin-1-yl]-pyridin-3-yl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-pyridin-2-yl-piperazin-1-yl)-phenyl]-acetamide;

N-[4-(4-Benzyl-piperazin-1-yl)-phenyl]-2-oxo-2-(2-phenyl-5,6,7,8-tetrahydro-indolizin-3-yl)-acetamide;

N-[4-(4-Isobutyl-piperazin-1-yl)-phenyl]-2-oxo-2-(2-phenyl-5,6,7,8-tetrahydro-indolizin-3-yl)-acetamide;

N-[4-(4-Cyclopropyl-piperazin-1-yl)-phenyl]-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-thiophen-2-ylmethyl-piperazin-1-yl)-phenyl]-acetamide;

N-[4-(4-Furan-2-ylmethyl-piperazin-1-yl)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-[2-tetrahydro-pyran-4-yl)-5,6,7,8-tetrahydro-indolizin-3-yl]-acetamide;

N-{5-[4-(4,6-Dimethyl-pyridin-2-yl)-piperazin-1-yl]-pyridin-2-yl}-2-oxo-2-(2-phenyl-5,6,7,8-tetrahydro-indolizin-3-yl)-acetamide;

N-{6-[4-(4,6-Dimethyl-pyridin-2-yl)-piperazin-1-yl]-pyridin-3-yl}-2-oxo-2-(2-phenyl-5,6,7,8-tetrahydro-indolizin-3-yl)-acetamide;

N-{4-[4-(5-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4-Methyl-pyridin-2-yl)-[1,4]diazepan-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-pyridin-2-yl-[1,4]diazepan-1-yl)-phenyl]-acetamide;

N-{4-[4-(6-Methyl-pyridin-2-yl)-[1,4]diazepan-1-yl}-phenyl]-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-propyl-piperazin-1-yl)-phenyl]-acetamide;

N-{4-[4-(3-Methyl-butyl)-piperazin-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-prop-2-ynyl-piperazin-1-yl)-phenyl]-acetamide;

N-[4-(4-Butyl-piperazin-1-yl)-phenyl]-2-oxo-2-(2-phenyl-5,6,7,8-tetrahydro-indolizin-3-yl)-acetamide;

N-[4-(4-Allyl-piperazin-1-yl)-phenyl]-2-oxo-2-(2-phenyl-5,6,7,8-tetrahydro-indolizin-3-yl)-acetamide;

N-{4-[4-(3-Methyl-but-2-enyl)-piperazin-1-yl]-phenyl}-2-oxo-2-(2-phenyl-5,6,7,8-tetrahydro-indolizin-3-yl)-acetamide;

N-{-4-[((E)-4-But-2-enyl)-piperazin-1-yl]-phenyl}-2-oxo-2-(2-phenyl-5,6,7,8-tetrahydro-indolizin-3-yl)-acetamide;

N-{4-[((Z)-4-But-2-enyl)-piperazin-1-yl]-phenyl}-2-oxo-2-(2-phenyl-5,6,7,8-tetrahydro-indolizin-3-yl)-acetamide;

2-(2-Isopropyl-5,6,7,8-tetrahydro-indolizin-3-yl)-N-{4-[4-(2-methyl-allyl)-piperazin-1-yl]-phenyl}-2-oxo-acetamide;

N-{4-[4-(2,2-Dimethyl-propyl)-piperazin-1-yl]-phenyl}-2-(2-isopropyl-5,6,7,8-tetrahydro-indolizin-3-yl)-2-oxo-acetamide;

N-{4-[4-(4,6-Dimethyl-pyridin-2-yl)-[1,4]diazepan-1-yl]-phenyl}-2-(2-isopropyl-5,6,7,8-tetrahydro-indolizin-3-yl)-2-oxo-acetamide;

2-(2-Cyclohexyl-5,6,7,8-tetrahydro-indolizin-3-yl)-N-{4-[4-(2-methyl-allyl)-piperazin-1-yl]-phenyl}-2-oxo-acetamide;

2-(2-Cyclohexyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclohexyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-N-{4-[4-(2-methyl-allyl)-piperazin-1-yl]-phenyl}-2-oxo-acetamide;

2-(2-Cyclopentyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclopentyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-2-oxo-N-[4-(4-pyridin-2-yl-piperazin-1-yl)-phenyl]-acetamide;
2-(2-Cyclopentyl-5,6,7,8-tetrahydro-indolizin-3-yl)-N-{4-[4-(4-methyl-pyridin-2-yl)-piperazin-1-yl]-phenyl}-2-oxo-acetamide;
2-(2-Cyclopentyl-5,6,7,8-tetrahydro-indolizin-3-yl)-N-{4-[4-(6-methyl-pyridin-2-yl)-piperazin-1-yl]-phenyl}-2-oxo-acetamide;
2-(2-Cyclopentyl-5,6,7,8-tetrahydro-indolizin-3-yl)-N-{4-[2-(4,6-dimethyl-pyridin-2-yloxy)-ethoxy]-phenyl}-2-oxo-acetamide;
2-(2-Cyclopentyl-5,6,7,8-tetrahydro-indolizin-3-yl)-N-{4-[4-(4-methoxy-6-methyl-pyridin-2-yl)-piperazin-1-yl]-phenyl}-2-oxo-acetamide;
2-(2-Cyclopentyl-5,6,7,8-tetrahydro-indolizin-3-yl)-N-[4-({2-[(4,6-dimethyl-pyridin-2-yl)-methyl-amino]-ethyl}-methyl-amino)-phenyl]-2-oxo-acetamide;
N-{4-({3-[(4,6-Dimethyl-pyridin-2-yl)-methyl-amino]-propyl}-methyl-amino)-phenyl}-2-oxo-2-(2-phenyl-5,6,7,8-tetrahydro-indolizin-3-yl)-acetamide;
N-{4-[4-(2-Methyl-allyl)piperazin-1-yl]-phenyl}-2-oxo-2-(2-phenyl-5,6,7,8-tetrahydro-indolizin-3-yl)-acetamide;
N-{4-[4-(2,2-Dimethyl-propyl)-piperazin-1-yl]-phenyl}-2-oxo-2-(2-phenyl-5,6,7,8-tetrahydro-indolizin-3-yl)-acetamide;
N-{4-[4-(4,6-Dimethyl-pyridin-2-yl)-piperazin-1-yl]-phenyl}-2-oxo-2-(2-phenyl-5,6,7,8-tetrahydro-indolizin-3-yl)-acetamide;
2-(2-Cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide;
N-{4-[4-(4,6-Dimethyl-pyridin-2-yl)-[1,4]diazepan-1-yl]-phenyl}-2-oxo-2-(2-phenyl-5,6,7,8-tetrahydro-indolizin-3-yl)-acetamide; and
N-{4-[4-(4,6-Dimethyl-pyridin-2-yl)-piperazin-1-yl]-phenyl}-N-methyl-2-oxo-2-(2-phenyl-5,6,7,8-tetrahydro-indolizin-3-yl)-acetamide.

In another embodiment of the invention preferred examples of compounds of formula (I) include:

N-{4-[2-(4,6-Dimethyl-pyridin-2-yloxy)-ethoxy]-phenyl}-2-oxo-2-(2-phenyl-5,6,7,8-tetrahydro-indolizin-3-yl)-acetamide;
N-{4-[4-(4-Methoxy-6-methyl-pyridin-2-yl)-piperazin-1-yl]-phenyl}-2-oxo-2-(2-phenyl-5,6,7,8-tetrahydro-indolizin-3-yl)-acetamide;
N-{4-[4-(4,6-Dimethyl-pyridin-2-yl)-piperazin-1-yl]-phenyl}-2-(2-isopropyl-5,6,7,8-tetrahydro-indolizin-3-yl)-2-oxo-acetamide;
2-(2-Cyclohexyl-5,6,7,8-tetrahydro-indolizin-3-yl)-N-{4-[4-(4,6-dimethyl-pyridin-2-yl)-piperazin-1-yl]-phenyl}-2-oxo-acetamide;
2-Oxo-2-(2-phenyl-5,6,7,8-tetrahydro-indolizin-3-yl)-N-[4-(4-pyridin-3-yl-piperazin-1-yl)-phenyl]-acetamide;
2-Oxo-2-(2-phenyl-5,6,7,8-tetrahydro-indolizin-3-yl)-N-{4-[2-(pyridin-2-yloxy)-ethylamino]-phenyl}-acetamide;
N-(4-{4-[4-(2-Methoxy-ethoxy)-6-methyl-pyridin-2-yl]-piperazin-1-yl}-phenyl)-2-oxo-2-(2-phenyl-5,6,7,8-tetrahydro-indolizin-3-yl)-acetamide;
N-[4-({2-[(4,6-Dimethyl-pyridin-2-yl)-methyl-amino]-ethyl}-methyl-amino)-phenyl]-2-oxo-2-(2-phenyl-5,6,7,8-tetrahydro-indolizin-3-yl)-acetamide;
N-{5-[4-(2,2-Dimethyl-propyl)-piperazin-1-yl]-pyridin-2-yl}-2-oxo-2-(2-phenyl-5,6,7,8-tetrahydro-indolizin-3-yl)-acetamide;
N-{4-[4-(4-Methyl-pyridin-2-yl)-piperazin-1-yl]-phenyl}-2-oxo-2-(2-phenyl-5,6,7,8-tetrahydro-indolizin-3-yl)-acetamide;
N-{4-[4-(6-Methyl-pyridin-2-yl)-piperazin-1-yl]-phenyl}-2-oxo-2-(2-phenyl-5,6,7,8-tetrahydro-indolizin-3-yl)-acetamide;
N-{4-[4-(4,6-Dimethyl-pyrimidin-2-yl)-piperazin-1-yl]-phenyl}-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-{4-[4-(3,3,3-trifluoro-propyl)-piperazin-1-yl]-phenyl}-acetamide;
N-{6-[4-(2,2-Dimethyl-propyl)-piperazin-1-yl]-pyridin-3-yl}-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-[4-(4-pyridin-2-yl-piperazin-1-yl)-phenyl]-acetamide;
N-[4-(4-Benzyl-piperazin-1-yl)-phenyl]-2-oxo-2-(2-phenyl-5,6,7,8-tetrahydro-indolizin-3-yl)-acetamide;
N-[4-(4-Isobutyl-piperazin-1-yl)-phenyl]-2-oxo-2-(2-phenyl-5,6,7,8-tetrahydro-indolizin-3-yl)-acetamide;
N-[4-(4-Cyclopropyl-piperazin-1-yl)-phenyl]-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-[4-(4-thiophen-2-ylmethyl-piperazin-1-yl)-phenyl]-acetamide;
N-[4-(4-Furan-2-ylmethyl-piperazin-1-yl)-phenyl]-2-oxo-2-(2-phenyl-5,6,7,8-tetrahydro-indolizin-3-yl)-acetamide;
N-{4-[4-(4,6-Dimethyl-pyridin-2-yl)-piperazin-1-yl]-phenyl}-2-oxo-2-[2-tetrahydro-pyran-4-yl)-5,6,7,8-tetrahydro-indolizin-3-yl]-acetamide;
N-{5-[4-(4,6-Dimethyl-pyridin-2-yl)-piperazin-1-yl]-pyridin-2-yl}-2-oxo-2-(2-phenyl-5,6,7,8-tetrahydro-indolizin-3-yl)-acetamide;
N-{6-[4-(4,6-Dimethyl-pyridin-2-yl)-piperazin-1-yl]-pyridin-3-yl}-2-oxo-2-(2-phenyl-5,6,7,8-tetrahydro-indolizin-3-yl)-acetamide;
N-{4-[4-(5-Methyl-pyridin-2-yl)-piperazin-1-yl]-phenyl}-2-oxo-2-(2-phenyl-5,6,7,8-tetrahydro-indolizin-3-yl)-acetamide;
N-{4-[4-(4-Methyl-pyridin-2-yl)-[1,4]diazepan-1-yl]-phenyl}-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-[4-(4-pyridin-2-yl-[1,4]diazepan-1-yl)-phenyl]-acetamide;
N-{4-[4-(6-Methyl-pyridin-2-yl)-[1,4]diazepan-1-yl]-phenyl}-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-[4-(4-propyl-piperazin-1-yl)-phenyl]-acetamide;
N-{4-[4-(3-Methyl-butyl)-piperazin-1-yl]-phenyl}-2-oxo-2-(2-phenyl-5,6,7,8-tetrahydro-indolizin-3-yl)-acetamide;
2-Oxo-2-(2-phenyl-5,6,7,8-tetrahydro-indolizin-3-yl)-N-[4-(4-prop-2-ynyl-piperazin-1-yl)-phenyl]-acetamide;
N-[4-(4-Butyl-piperazin-1-yl)-phenyl]-2-oxo-2-(2-phenyl-5,6,7,8-tetrahydro-indolizin-3-yl)-acetamide;
N-[4-(4-Allyl-piperazin-1-yl)-phenyl]-2-oxo-2-(2-phenyl-5,6,7,8-tetrahydro-indolizin-3-yl)-acetamide;
N-{4-[4-(3-Methyl-but-2-enyl)-piperazin-1-yl]-phenyl}-2-oxo-2-(2-phenyl-5,6,7,8-tetrahydro-indolizin-3-yl)-acetamide;
N-{4-[((E)-4-But-2-enyl)-piperazin-1-yl]phenyl}-2-oxo-2-(2-phenyl-5,6,7,8-tetrahydro-indolizin-3-yl)-acetamide;
N-{4-[((Z)-4-But-2-enyl)-piperazin-1-yl]-phenyl}-2-oxo-2-(2-phenyl-5,6,7,8-tetrahydro-indolizin-3-yl)-acetamide;
2-(2-Isopropyl-5,6,7,8-tetrahydro-indolizin-3-yl)-N-{4-[4-(2-methyl-allyl)-piperazin-1-yl]-phenyl}-2-oxo-acetamide;

N-{4-[4-(2,2-Dimethyl-propyl)-piperazin-1-yl]-phenyl}-2-(2-isopropyl-5,6,7,8-tetrahydro-indolizin-3-yl)-2-oxo-acetamide;

N-{4-[4-(4,6-Dimethyl-pyridin-2-yl)-[1,4]diazepan-1-yl]-phenyl}-2-(2-isopropyl-5,6,7,8-tetrahydro-indolizin-3-yl)-2-oxo-acetamide;

2-(2-Cyclohexyl-5,6,7,8-tetrahydro-indolizin-3-yl)-N-{4-[4-(2-methyl-allyl)-piperazin-1-yl]-phenyl}-2-oxo-acetamide;

2-(2-Cyclohexyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclohexyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-N-{4-[4-(2-methyl-allyl)-piperazin-1-yl]-phenyl}-2-oxo-acetamide;

2-(2-Cyclopentyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclopentyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-2-oxo-N-[4-(4-pyridin-2-yl-piperazin-1-yl)-phenyl]-acetamide;

2-(2-Cyclopentyl-5,6,7,8-tetrahydro-indolizin-3-yl)-N-{4-[4-(4-methyl-pyridin-2-yl)-piperazin-1-yl]-phenyl}-2-oxo-acetamide;

2-(2-Cyclopentyl-5,6,7,8-tetrahydro-indolizin-3-yl)-N-{4-[4-(6-methyl-pyridin-2-yl)-piperazin-1-yl]-phenyl}-2-oxo-acetamide;

2-(2-Cyclopentyl-5,6,7,8-tetrahydro-indolizin-3-yl)-N-{4-[2-(4,6-dimethyl-pyridin-2-yloxy)-ethoxy]-phenyl}-2-oxo-acetamide;

2-(2-Cyclopentyl-5,6,7,8-tetrahydro-indolizin-3-yl)-N-{4-[4-(4-methoxy-6-methyl-pyridin-2-yl)-piperazin-1-yl]-phenyl}-2-oxo-acetamide;

2-(2-Cyclopentyl-5,6,7,8-tetrahydro-indolizin-3-yl)-N-[4-({2-[(4,6-dimethyl-pyridin-2-yl)-methyl-amino]-ethyl}-methyl-amino)-phenyl]-2-oxo-acetamide;

N-[4-({3-[(4,6-Dimethyl-pyridin-2-yl)-methyl-amino]-propyl}-methyl-amino)-phenyl]-2-oxo-2-(2-phenyl-5,6,7,8-tetrahydro-indolizin-3-yl)-acetamide;

N-{4-[4-(2-Methyl-allyl)piperazin-1-yl]-phenyl}-2-oxo-2-(2-phenyl-5,6,7,8-tetrahydro-indolizin-3-yl)-acetamide;

N-{4-[4-(2,2-Dimethyl-propyl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-(2-phenyl-5,6,7,8-tetrahydro-indolizin-3-yl)-acetamide;

2-(2-Cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide;

N-{4-[4-(4,6-Dimethyl-pyridin-2-yl)-[1,4]diazepan-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-N-methyl-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-[2-(1-methyl-piperidin-4-yl)-5,6,7,8-tetrahydro-indolizin-3-yl]-2-oxo-acetamide;

2-Oxo-N-(1-phenyl-piperidin-4-yl)-2-(2-phenyl-5,6,7,8-tetrahydro-indolizin-3-yl)-acetamide;

N-{4-[4-(6-Methoxy-4-methyl-pyridin-2-yl)-piperazin-1-yl]-phenyl}-2-oxo-2-(2-phenyl-5,6,7,8-tetrahydro-indolizin-3-yl)-acetamide;

N-{4-[2-(2,6-Dimethyl-pyridin-4-yloxy)-ethoxy]-phenyl}-2-oxo-2-(2-phenyl-5,6,7,8-tetrahydro-indolizin-3-yl)-acetamide;

N-{4-[4-(6-Ethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4-Ethyl-pyridin-2-yl)-piperazin-1-yl]-phenyl}-2-oxo-2-(2-phenyl-5,6,7,8-tetrahydro-indolizin-3-yl)-acetamide;

N-{4-[4-(5-Morpholin-4-ylmethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methyl-phenyl}-2-oxo-2-(2-phenyl-5,6,7,8-tetrahydro-indolizin-3-yl)-acetamide;

N-[4-(4-Hydroxy-4',6'-dimethyl-3,4,5,6-tetrahydro-2H-[1,2]bipyridinyl-4-yl)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-[3-(4-methyl-piperazin-1-yl)-propoxymethyl]-phenyl}-2-oxo-2-(2-phenyl-5,6,7,8-tetrahydro-indolizin-3-yl)-acetamide;

N-[4-[4-(4,6-Dimethyl-pyridin-2-yl)-piperazin-1-yl]-3-(3-morpholin-4-yl-propoxymethyl)-phenyl]-2-oxo-2-(2-phenyl-5,6,7,8-tetrahydro-indolizin-3-yl)-acetamide;

N-{3-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-Naphthalen-1-yl-2-oxo-2-(2-phenyl-5,6,7,8-tetrahydro-indolizin-3-yl)-acetamide;

N-{3-(2-Dimethylamino-ethoxymethyl)-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{2-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-hydroxy-phenyl}-2-oxo-2-(2-phenyl-5,6,7,8-tetrahydro-indolizin-3-yl)-acetamide; and N-(2,3-Dihydro-benzofuran-6-yl)-2-oxo-2-(2-phenyl-5,6,7,8-tetrahydro-indolizin-3-yl)-acetamide.

Particularly preferred examples of compounds of formula (I) include:

N-{4-[4-(2-Methyl-allyl)piperazin-1-yl]-phenyl}-2-oxo-2-(2-phenyl-5,6,7,8-tetrahydro-indolizin-3-yl)-acetamide;

N-{4-[4-(2,2-Dimethyl-propyl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-(2-phenyl-5,6,7,8-tetrahydro-indolizin-3-yl)-acetamide;

2-(2-Cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide;

N-{4-[4-(4,6-Dimethyl-pyridin-2-yl)-[1,4]diazepan-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-N-methyl-2-oxo-2-(2-phenyl-5,6,7,8-tetrahydro-indolizin-3-yl)-acetamide;

N-[4-({2-[(4,6-Dimethyl-pyridin-2-yl)-methyl-amino]-ethyl}-methyl-amino)-phenyl]-2-oxo-2-(2-phenyl-5,6,7,8-tetrahydro-indolizin-3-yl)-acetamide;

N-{4-[4-(4-Methoxy-6-methyl-pyridin-2-yl)-piperazin-1-yl]-phenyl}-2-oxo-2-(2-phenyl-5,6,7,8-tetrahydro-indolizin-3-yl)-acetamide;

N-{4-[2-(4,6-Dimethyl-pyridin-2-yloxy)-ethoxy]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-[2-(tetrahydro-pyran-4-yl)-5,6,7,8-tetrahydro-indolizin-3-yl]-acetamide;

N-{4-[4-(4,6-Dimethyl-pyridin-2-yl)-piperazin-1-yl]-phenyl}-2-[2-(1-methyl-piperidin-4-yl)-5,6,7,8-tetrahydro-indolizin-3-yl]-2-oxo-acetamide;

2-Oxo-N-(1-phenyl-piperidin-4-yl)-2-(2-phenyl-5,6,7,8-tetrahydro-indolizin-3-yl)-acetamide;

N-{4-[4-(6-Methoxy-4-methyl-pyridin-2-yl)-piperazin-1-yl]-phenyl}-2-oxo-2-(2-phenyl-5,6,7,8-tetrahydro-indolizin-3-yl)-acetamide;

N-{4-[2-(2,6-Dimethyl-pyridin-4-yloxy)-ethoxy]-phenyl}-2-oxo-2-(2-phenyl-5,6,7,8-tetrahydro-indolizin-3-yl)-acetamide;

N-{4-[4-(6-Ethyl-pyri din-2-yl)-piperazin-1-yl]-phenyl}-2-oxo-2-(2-phenyl-5,6,7,8-tetrahydro-indolizin-3-yl)-acetamide;

N-{4-[4-(5-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4-Ethyl-pyridin-2-yl)-piperazin-1-yl]-phenyl}-2-oxo-2-(2-phenyl-5,6,7,8-tetrahydro-indolizin-3-yl)-acetamide;

N-{4-[4-(5-Morpholin-4-ylmethyl-pyridin-2-yl)-piperazin-1-yl]-phenyl}-2-oxo-2-(2-phenyl-5,6,7,8-tetrahydro-indolizin-3-yl)-acetamide;

N-[4-({3-[(4,6-Dimethyl-pyridin-2-yl)-methyl-amino]-propyl}-methyl-amino)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methyl-phenyl}-2-oxo-2-(2-phenyl-5,6,7,8-tetrahydro-indolizin-3-yl)-acetamide;

N-[4-(4-Hydroxy-4',6'-dimethyl-3,4,5,6-tetrahydro-2H-[1,2']bipyridinyl-4-yl)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-[3-(4-methyl-piperazin-1-yl)-propoxymethyl]-phenyl}-2-oxo-2-(2-phenyl-5,6,7,8-tetrahydro-indolizin-3-yl)-acetamide;

N-[4-[4-(4,6-Dimethyl-pyridin-2-yl)-piperazin-1-yl]-3-(3-morpholin-4-yl-propoxymethyl)-phenyl]-2-oxo-2-(2-phenyl-5,6,7,8-tetrahydro-indolizin-3-yl)-acetamide;

N-{3-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-Naphthalen-1-yl-2-oxo-2-(2-phenyl-5,6,7,8-tetrahydro-indolizin-3-yl)-acetamide;

N-{3-(2-Dimethylamino-ethoxymethyl)-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{2-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-hydroxy-phenyl}-2-oxo-2-(2-phenyl-5,6,7,8-tetrahydro-indolizin-3-yl)-acetamide; and N-(2,3-Dihydro-benzofuran-6-yl)-2-oxo-2-(2-phenyl-5,6,7,8-tetrahydro-indolizin-3-yl)-acetamide.

Compounds of the invention containing one or more chiral centre may be used in enantiomerically or diastereoisomerically pure form, or in the form of a mixture of isomers. For the avoidance of doubt, the compounds of the invention can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic, hydroiodic or nitric acid and organic acids such as citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines, lysine, guanidine, diethanolamine and choline.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

The present invention also provides prodrugs of the compounds of the invention. A prodrug is an analogue of a compound of the invention which will be converted in vivo to the desired active compound. Examples of suitable prodrugs include compounds of formula (I) which have been modified at a carboxylic acid group to form an ester, or at hydroxyl group to form an ester or carbamate. Other suitable methods will be known to those skilled in the art. Further suitable prodrugs include those in which a nitrogen atom of a compound of formula (I) is quaternised by addition of an ester or alkyl ester group. For example, the nitrogen atom of an amine group or heterocyclyl ring on a substituent $R_1$ or $R_2$ may be quaternised by addition of a —$CH_2$—O—COR group, wherein R is typically methyl or tert-butyl.

Suitable salts of the compounds of the invention include those mentioned herein as examples of pharmaceutically and agriculturally acceptable salts.

The compounds of the invention may be synthesised by reacting a compound of formula (II), wherein R2, R3, R4, R5, R6 and R7 are as hereinbefore defined, with a compound of formula (III), wherein R8, A1, n, L1 and R1 are as hereinbefore defined, and subsequently reducing the indolizinyl ring using Raney Ni in MeOH/EtOAc. Typically the initial stage of the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete. Compounds of formula (III) are typically available from commercial sources or can be prepared by known methods. Details of the synthesis of certain compounds of formula (III) are provided hereinafter.

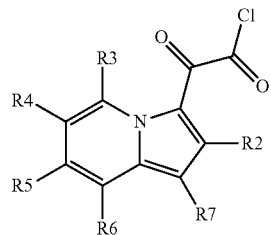

(II)

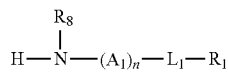

(III)

A compound of formula (II) may be prepared by reacting a compound of formula (IV), wherein R2, R3, R4, R5, R6 and R7 are as hereinbefore defined, with preferably oxalyl chloride. Typically the reaction takes place in an organic solvent. Preferably, the solvent is a tetrahydrofuran, a mixture of tetrahydrofuran/toluene, or diethyl ether. Typically, the reaction is carried out at 0° C. initially while the reagents are added and then stirred at room temperature until the reaction is complete.

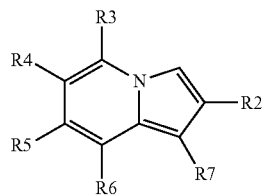

(IV)

A compound of formula (IV) may be prepared by reacting a compound of formula (V), wherein R2, R3, R4, R5, R6, and R7 are as hereinbefore defined, with a base. Preferably the solvent is water and the base is $NaHCO_3$. Typically, the reaction is heated to reflux.

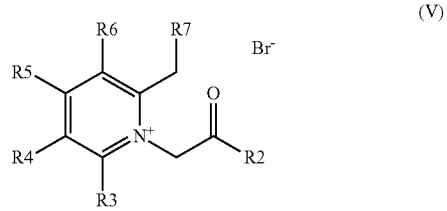

(V)

A compound of formula (V) may be prepared by reacting a compound of formula (VI), wherein R2 is hereinbefore defined, with a compound of formula (VII), wherein R3, R4, R5, R6, R7 are as hereinbefore defined. Typically, the reaction takes place in the presence of an organic solvent. Preferably the solvent is methanol. Typically, the reaction is heated to reflux.

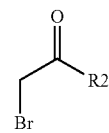

(VI)

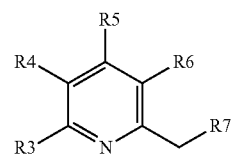

(VII)

Compounds of formula (VI) are available from standard commercial sources or may be prepared by reacting a compound of formula (VIII), which are available from standard commercial sources or can be prepared by analogy with known techniques, wherein R2 is hereinbefore defined, with a suitable brominating agent. Typically, the brominating conditions are hydrobromic acid in acetic acid, followed by pyridinium tribromide or bromine in dioxane/ether. Typically, the reaction is kept at room temperature.

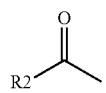

(VIII)

An alternative method for the preparation of the compounds of the invention involves reacting a compound Int-III, wherein R2, R3, R4, R5, R6 and R7 are as hereinbefore defined, with a compound of formula (III). Typically the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete.

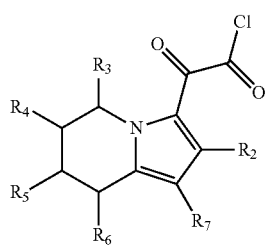

Int III

Int-III can be prepared by reducing a compound of formula (IV) in the presence of $H_2$, Raney Ni, and MeOH to produce a compound Int IIIa, followed by reacting Int IIIa with oxalyl chloride. Typically the reaction with oxalyl chloride takes place in an organic solvent. Preferably, the solvent is a tetrahydrofuran, a mixture of tetrahydrofuran/toluene, or diethyl ether. Typically, the reaction is carried out at 0° C. initially while the reagents are added and then stirred at room temperature until the reaction is complete.

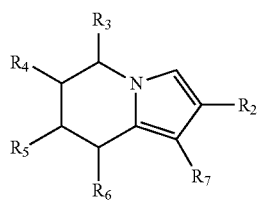

Int IIIa

Many of the starting materials referred to in the reactions described above are available from commercial sources or can be prepared by analogy with known methods.

The compounds of the invention have antifungal activity. Accordingly, they may be used in a method of treating a subject suffering from or susceptible to a fungal disease, which method comprises administering to said subject an effective amount of an tetrahydroindolizinyl derivative of formula (I) or (IA) or a pharmaceutically acceptable salt thereof. The tetrahydroindolizinyl derivatives of formula (I) or (IA) or the pharmaceutically acceptable salts thereof may also be used in the manufacture of a medicament for use in the prevention or treatment of a fungal disease.

Preferably, the fungal disease comprises an infection by a fungus, for example an Ascomycete. Preferably, the fungal disease comprises an infection by an organism selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fusarium; Histoplasma; Leptosphaeria; Microsporum; Mycosphaerella; Neurospora, Paecilomyces; Phytophthora; Plasmopara; Pneumocystis; Pyricularia; Pythium; Puccinia; Rhizoctonia; Rhizomucor; Scedosporium; Scopulariopsis; Trichophyton; Trichosporon*; and *Ustilago*.

Preferably, the fungal disease comprises an infection by an organism of the genus *Aspergillus* or *Candida*.

Preferably, the fungal disease comprises an infection by an organism selected from the species *Absidia corymbifera; Acremonium* spp; *Alternaria alternata; Aspergillus flavus; Aspergillus fumigatus; Aspergillus nidulans; Aspergillus niger; Aspergillus parasiticus; Aspergillus terreus; Bipolaris* spp; *Blastomyces dermatitidis; Blumeria graminis; Candida albicans; Candida glabrata; Candida krusei; Candida parapsilosis; Candida tropicalis; Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrum; Epidermophyton floccosum; Exophiala* spp; *Exserohilum rostratum; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oiyzae; Pythium ultimum; Rhizoctonia solani; Rhizomucor* spp; *Rhizopus* spp; *Scedosporium apiospermum; Scedosporiuni prolificans; Scopulariopsis brevicaulis; Trichophyton mentagrophytes; Trichophyton interdigitale; Trichophyton rubrum; Trichosporon asahii; Trichosporon beigelii*; and *Ustilago maydis*.

Preferably, the fungal disease comprises an infection by *Aspergillus fumigatus*.

Examples of fungal diseases, which can be prevented or treated using the compounds of the invention, include both systemic and superficial infections. The fungal diseases include invasive fungal diseases caused by *Aspergillus* and *Candida* species such as aspergillosis or candidiasis, but also local forms of these infections. The compounds of the invention are particularly useful against diseases caused by *Aspergillus* species, for which a fungicidal drug is required which has lower toxicity than amphotericin. The invention also provides for the treatment of dermatological infections.

The diseases caused by *Aspergillus* species include diseases caused by *A. fumigatus, A. flavus, A. terreus* and *A. niger*.

The diseases cause by *Candida* species include diseases caused by *C. albicans, C. glabrata, C. krusei, C. tropicalis* and *C. parapsillosis*.

Examples of systemic infections which might be prevented or treated using the compounds of the invention include: systemic candidiasis; pulmonary aspergillosis, e.g. in immunosuppressed patients such as bone marrow recipients or AIDS patients; systemic aspergillosis; cryptococcal meningitis; rhinocerebral mucomycosis; blastomycosis; histoplasmosis; coccidiomycosis; paracoccidiomycosis; lobomycosis; sporotrichosis; chromoblastomycosis; phaeohyphomycosis; zygomycosis; cryptococcosis and disseminated sporotrichosis.

Examples of superficial infections, which can be prevented or treated using the compounds of the invention, include: ring worm; athlete's foot; tinea unguium (nail infection); candidiasis of skin, mouth or vagina; and chronic mucocutaneous candidiasis.

Examples of diseases or conditions which are caused by fungi or where fungi exacerbate an allergic response, and which can be prevented or treated using the compounds of the invention, include allergic bronchopulmonary asthma (ABPA); asthma, rhinosinusitis and sinusitis.

The present invention includes a pharmaceutical composition comprising a compound according to the invention and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen free. Where a compound of the invention can exist as optical isomers, the pharmaceutical compositions provided by the invention typically contain a substantially pure optical isomer.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, either subcutaneously, intravenously, intramuscularly, intrasternally, transdermally or by infusion techniques. The compounds may also be administered as suppositories. The compounds may be administered by inhalation in the form of an aerosol via an inhaler or nebuliser.

A compound of the invention is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

A therapeutically effective amount of a compound of the invention is administered to a patient. A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg. The compound of the invention is typically administered to the patient in a non-toxic amount.

The present invention also provides a method of controlling a fungal disease of a plant, which comprises applying to the locus of the plant a derivative of formula (I) or formula (IA) or an agriculturally acceptable salt thereof.

The compounds of the invention may, for example, be applied to the seeds of the plants, to the medium (e.g. soil or water) in which the plants are grown, or to the foliage of the plants.

Examples of fungal diseases of plants which can be controlled using the compounds of the invention include fungal diseases caused by the following plant pathogens: *Blumeria graminis; Colletotrichium trifolii; Fusarium graminearium; Fusarium solani; Fusarium sporotrichoides; Leptosphaeria nodorum; Magnaporthe grisea; Mycosphaerella graminicola; Neurospora crassa; Phytophthora capsici; Phytophthora infestans; Plasmopara viticola; Puccinia coronata; Puccinia graminis; Pyricularia oryzae; Pythium ultimum; Rhizoctonia solani; Trichophyton rubrum*; and *Ustilago maydis.*

The present invention includes a composition comprising a compound of the invention, or an agriculturally acceptable salt thereof, and an agriculturally acceptable carrier or diluent. Said agricultural composition typically contains up to 85 wt % of a compound of the invention. More typically, it contains up to 50 wt % of a compound of the invention.

Suitable agriculturally acceptable salts include salts with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Salts may also be formed with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. A preferred agriculturally acceptable salt is the hydrochloride salt.

The compounds of the invention may be applied in combination with inert carriers or diluents, as in aqueous sprays, granules and dust formulations in accordance with established practice in the art. An aqueous spray is usually prepared by mixing a wettable powder or emulsifiable concentrate formulation of a compound of the invention with a relatively large amount of water to form a dispersion.

Wettable powders may comprise an intimate, finely divided mixture of a compound of the invention, an inert solid carrier and a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates may comprise a solution of a compound of the invention in a liquid carrier which is a mixture of a water-immiscible solvent and a surfactant, including an emulsifier. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The fungicide formulations desirably contain from 0.1 percent to 95 percent by weight of the compound of the invention and from 0.1 to 75 percent of an inert carrier or surfactant. The direct application to plant seeds prior to planting may be accomplished in some instances by mixing either a powdered solid compound of the invention or a dust formulation with seed to obtain a substantially uniform coating which is very thin and represents only one or two percent by weight or less, based on the weight of the seed. In some instances, however, a non-phytotoxic solvent such as methanol is conveniently employed as a carrier to facilitate the uniform distribution of the compound of the invention on the surface of the seed.

When a compound of the invention is to be applied to the soil, as for pre-emergence protection, granular formulations or dusts are sometimes more convenient than sprays. A typical granular formulation comprises a compound of the invention dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

The following examples illustrate the invention but are not intended to limit the scope of the invention. In this regard, it is important to understand that the particular assays used in the Examples section are designed only to provide an indication of anti-fungal activity. There are many assays available to determine such activity, and a negative result in any one particular assay is therefore not determinative.

EXAMPLES

Reference Example 1

1-Methyl-piperidine-4-carboxylic Acid Hydrochloride a) Preparation of 1-methyl-piperidine-4-carboxylic acid ethyl ester Ethyl isonipecotate (3.0 g, 19.1 mmol) was added to a mixture of 90% formic acid (10 mL) and 30% aqueous formaldehyde (10 mL, 100 mmol) then the mixture was heated at reflux for 24 h. After cooling, the mixture was concentrated in vacuo to give an oil which was dissolved in dichloromethane. Solid sodium bicarbonate (1 g) was added and the mixture stirred for 1 h then filtered. The filtrate was concentrated in vacuo to afford 1-methyl-piperidine-4-carboxylic acid ethyl ester (2.0 g, 61%) as a liquid, which was used as such for the next step.

b) Preparation of 1-methyl-piperidine-4-carboxylic Acid Ethyl Ester

A solution of 1-methyl-piperidine-4-carboxylic acid ethyl ester (2.0 g, 11.7 mmol) in conc. hydrochloric acid (20 mL) was heated to 100° C. and maintained for 6 h. The mixture was then concentrated to dryness in vacuo to give a solid, which was washed with acetonitrile-diethyl ether (1:1) and dried in vacuo to afford 1-methyl-piperidine-4-carboxylic acid hydrochloride (1.0 g, 48%) as an off-white solid.

Reference Example 2

Tetrahydro-pyran-4,4-dicarboxylic Acid Diethyl Ester

A solution of diethyl malonate (15.2 mL, 99.8 mmol) in ethanol (10 mL) was added dropwise to a solution of sodium ethoxide in ethanol [freshly prepared from sodium (2.3 g, 100 mmol) and ethanol (30 mL)] at ambient temperature and stirred for 10 min. Bis(2-chloroethyl)ether (12 mL, 102 mmol) was added dropwise then the mixture was heated at reflux overnight. It was then cooled to 10° C. before another portion of freshly-prepared sodium ethoxide in ethanol [prepared from sodium (2.3 g, 100 mmol) and ethanol (30 mL)] was added. The mixture was heated at reflux for 48 h then cooled, filtered to remove the precipitated sodium chloride then the filtrate was concentrated to dryness. Water was added to the residue which was then extracted with ether (3×25 mL). The combined ether layers were washed with water, brine and dried over anhydrous sodium sulfate. Concentration under reduced pressure yielded tetrahydropyran-4,4-dicarboxylic acid diethyl ester (10.1 g, 44%) as a mobile oil.

Reference Example 3

Tetrahydro-pyran-4,4-dicarboxylic Acid 6M potassium hydroxide solution (10 mL, 60 mmol) was added to an ice-cooled solution of tetrahydropyran-4,4-dicarboxylic acid diethyl ester (5 g, 21.7 mmol) in ethanol (40 mL) and heated at reflux overnight. The volatiles were evaporated, the residue diluted with water and acidified with conc. hydrochloric acid. The mixture was allowed to stand overnight then extracted with ether (3×25 mL). The combined ether layers were washed with brine, dried over sodium sulfate, and concentrated in vacuo to afford tetrahydro-pyran-4,4-dicarboxylic acid (2.3 g, 61%) as a white solid.

Reference Example 4

Tetrahydro-pyran-4-carboxylic Acid

Tetrahydro-pyran-4,4-dicarboxylic acid (2.3 g, 13.2 mmol) was heated at 178-180° C. for 30 minutes. The reaction mixture was cooled to ambient temperature and washed with pentane to afford tetrahydro-pyran-4-carboxylic acid (1.1 g, 64%) as a solid.

Reference Example 5

2-bromo-1-(tetrahydro-pyran-4-yl)-ethanone

Thionyl chloride (2 mL, 27 mmol) was added to tetrahydro-pyran-4-carboxylic acid (1.1 g, 8.4 mmol) at 10° C. The mixture was warmed to ambient temperature and stirred for 2 h. Excess thionyl chloride was evaporated and the residue co-distilled with toluene to remove the traces of thionyl chloride. The resulting crude acid chloride was dissolved in dry acetonitrile (3 mL) and cooled to 0° C. Trimethylsilyl diazomethane (12.6 mL, 25.3 mmol) was added and the reaction mixture was stirred at ambient temperature for 2 h. It was then cooled to −10° C. and a solution of 15% HBr in acetic acid (2 mL) was added. The mixture was stirred at room temperature for 1 h then quenched with saturated sodium bicarbonate solution and extracted with ether (3×20 mL). The combined ether extracts were washed with brine, dried over anhydrous sodium sulfate and concentrated in vacuo to afford 2-bromo-1-(tetrahydro-pyran-4-yl)-ethanone (620 mg, 35%) as an oil.

Reference Example 6

The compound set out below was prepared in a manner analogous to Reference Example 5 (2-bromo-1-(tetrahydro-pyran-4-yl)-ethanone), the product being isolated by filtration and washing with ether after the treatment with HBr.

| Reference Example | Compound |
|---|---|
| 6 | 2-Bromo-1-(1-methyl-piperidin-4-yl)-ethanone (HBr salt) |

Reference Example 7

2-cyclopentanecarbonyl Malonic Acid Diethyl Ester

Cyclopentanecarboxylic acid (10 g, 88 mmol) was heated under reflux with thionyl chloride (13 mL, 176 mmol). After 2 hrs, excess thionyl chloride was distilled under reduced pressure and the acid chloride (9.8 g) was collected as a liquid.

In another vessel, sodium hydride (50% dispersion in oil, 4.28 g, 89 mmol) was suspended in THF (100 mL) and diethyl malonate (11.9 g, 74.2 mmol) was added dropwise at 0° C. The previously-prepared acid chloride (9.8 g, 74 mmol) was added dropwise at 0° C. and the mixture stirred at room temperature for 1 hr. The mixture was quenched with cold water and extracted with ethyl acetate. The organic layer was washed with water, sodium bicarbonate solution and brine, dried over sodium sulfate and concentrated to afford 2-cyclopentanecarbonyl malonic acid diethyl ester (19.2 g, 85%) as a liquid.

Reference Example 8

1-cyclopentyl-ethanone

2-Cyclopentanecarbonyl malonic acid diethyl ester (19.0 g, 74.2 mmol) was heated with concentrated hydrochloric acid at 90° C. overnight. The reaction mixture was cooled to room temperature and diluted with water. The mixture was extracted with diethyl ether, the organic layer then being washed with water, sodium bicarbonate solution and brine. It was dried over sodium sulfate and concentrated to give 1-cyclopentyl-ethanone as a liquid (3.1 g, 37%).

Reference Example 9

2-bromo-1-(1-bromo-cyclopentyl)-ethanone

Bromine (1.1 mL, 21.4 mmol) was added dropwise at 0° C. to a solution of 1-cyclopentyl-ethanone (2.4 g, 21.4 mmol) in 1:1 ether/petroleum-ether (50 mL). The reaction mixture was warmed to 20° C. and stirred for 1 hour then quenched with cold water and extracted with diethyl ether (×2). The combined organic phase was washed with water, sodium bicarbonate solution and brine. It was dried over sodium sulfate and concentrated to afford 2-bromo-1-(1-bromo-cyclopentyl)-ethanone (3.7 g, 64%) as a liquid.

Reference Example 10

1-(2-cyclopent-1-enyl-2-oxo-ethyl)-2-methyl-pyridinium Bromide

2-Bromo-1-(1-bromo-cyclopentyl)-ethanone (3.7 g, 13.7 mmol) and α-picoline (1.02 g, 11.0 mmol) in acetone were heated at reflux overnight. The reaction mixture was allowed to cool then concentrated in vacuo. The crude mass was washed with 30% ethyl acetate/petroleum ether and diethyl ether. 1-(2-Cyclopent-1-enyl-2-oxo-ethyl)-2-methyl-pyridinium bromide salt (3.65 g, 94%) was obtained as a semi-solid material and taken for next step without purification.

Reference Example 11

1-(2-cyclopentyl-2-oxo-ethyl)-2-methyl-pyridinium Bromide

A solution of 1-(2-cyclopent-1-enyl-2-oxo-ethyl)-2-methyl-pyridinium bromide salt (3.65 g, 12.9 mmol) in methanol (25 mL) was hydrogenated over 10% Pd/C (180 mg). After completion of the reaction the catalyst was removed by filtration, washing with methanol, and concentration of the filtrate gave 1-(2-cyclopentyl-2-oxo-ethyl)-2-methyl-pyridinium bromide salt (3.4 g, 93%).

Reference Example 12

2-Methyl-1-[2-oxo-2-(tetrahydro-pyran-4-yl)-ethyl]-pyridinium Bromide

A mixture of 2-bromo-1-(tetrahydro-pyran-4-yl)-ethanone (0.6 g, 2.89 mmol) and 2-picoline (0.4 mL, 4.3 mmol) in methanol (10 mL) was heated to reflux and maintained overnight. The solvent was removed in vacuo to give a residue which was washed with 20% ethyl acetate in hexane to afford 2-methyl-1-[2-oxo-2-(tetrahydro-pyran-4-yl)-ethyl]-pyridinium bromide (0.75 g, 86%) as a semi-solid.

Reference Example 13

The compound set out below was prepared in a manner analogous to Reference Example 12 (2-methyl-1-[2-oxo-2-(tetrahydro-pyran-4-yl)-ethyl]-pyridinium bromide).

| Reference Example | Compound |
|---|---|
| 13 | 2-Methyl-1-[2-(1-methyl-piperidin-4-yl)-2-oxo-ethyl]-pyridinium bromide |

Reference Example 14

2-cyclopentyl-indolizine 1-(2-Cyclopentyl-2-oxo-ethyl)-2-methyl-pyridinium bromide salt (3.4 g, 12.0 mmol) was heated at reflux in saturated sodium bicarbonate solution for 3 hrs. The mixture was allowed to cool, diluted with water and extracted with ethyl acetate (×2). The combined organic phases were washed with water and brine, dried over sodium sulfate and concentrated to give a residue which was purified by column chromatography using 100-200 mesh silica-gel and 1% ethyl acetate/petroleum-ether as eluent to afford 2-cyclopentyl-indolizine (0.91 g, 41%) as a solid.

Reference Examples 15 and 16

The compounds set out below were prepared in a manner analogous to Reference Example 14 (2-cyclopentyl-indolizine).

| Reference Example | Compound |
|---|---|
| 15 | 2-(Tetrahydro-pyran-4-yl)-indolizine |
| 16 | 2-(1-Methyl-piperidin-4-yl)-indolizine |

Reference Example 17

2-phenyl-5,6,7,8-tetrahydro-indolizine

Raney nickel (6 g) was slurried in ethanol (100 mL) and a solution of 2-phenylindolizine (48 g, 0.24 mol) in ethanol (1 L) was added. The reaction mixture was stirred under hydrogen at room temperature and 50-60 psi overnight. The mixture was filtered through Celite then the solvent was evaporated under vacuum to yield 2-phenyl-5,6,7,8-tetrahydro-indolizine (32 g, 65%) as a white solid.

Reference Example 18

2-cyclopentyl-5,6,7,8-tetrahydro-indolizine

2-Cyclopentyl-indolizine (0.25 g, 1.35 mmol) was dissolved in methanol (5 mL) and hydrogenated over Raney nickel (50 mg) under balloon pressure at room temperature for 1 h. The reaction mixture was filtered through celite, washing with methanol. Concentration of the filtrate afforded 2-cyclopentyl-5,6,7,8-tetrahydro-indolizine (0.24 g, 94%) as a solid.

Reference Examples 19 and 20

The compounds set out below were prepared in a manner analogous to Reference Example 17 (2-phenyl-5,6,7,8-tetrahydro-indolizine) and 18 (2-cyclopentyl-5,6,7,8-tetrahydro-indolizine).

| Reference Example | Compound |
|---|---|
| 19 | 2-(Tetrahydro-pyran-4-yl)-5,6,7,8-tetrahydro-indolizine |
| 20 | 2-(1-Methyl-piperidin-4-yl)-5,6,7,8-tetrahydro-indolizine |

Reference Example 21

Oxo-(2-phenyl-5,6,7,8-tetrahydro-indolizin-3-yl)-acetyl Chloride

Oxalyl chloride (17.2 mL, 0.19 mol) was added to an ice-cold solution of 2-phenyl-5,6,7,8-tetrahydro-indolizine (32 g, 0.16 mol) in a mixture of toluene (20 mL) and THF (30 mL). The reaction mixture was allowed to warm to room temperature and stirred for 30 min. then concentrated under vacuum. The residue was triturated with petrol (5×300 mL) to afford oxo-(2-phenyl-5,6,7,8-tetrahydro-indolizin-3-yl)-acetyl chloride (42 g, 89%) as a dark yellow solid.

Reference Example 22

(2-cyclopentyl-5,6,7,8-tetrahydro-indolizin-3-yl)-oxo-acetyl Chloride

2-Cyclopentyl-5,6,7,8-tetrahydro-indolizine (0.24 g, 1.27 mmol) was dissolved in THF (1 mL) and toluene (1.5 mL) and cooled to 0° C. Oxalyl chloride (0.14 mL, 1.52 mmol) was added dropwise and the mixture was stirred at 0° C. for 30 min, then at room temperature for 1 hour. Concentration in vacuo afforded (2-cyclopentyl-5,6,7,8-tetrahydro-indolizin-3-yl)-oxo-acetyl chloride (0.31 g, 88%) as a semi-solid.

Reference Examples 23 and 24

The compounds set out below were prepared in a manner analogous to Reference Example 21 (oxo-(2-phenyl-5,6,7,8-tetrahydro-indolizin-3-yl)-acetyl chloride) and Reference Example 22 ((2-cyclopentyl-5,6,7,8-tetrahydro-indolizin-3-yl)-oxo-acetyl chloride).

| Reference Example | Compound |
|---|---|
| 23 | Oxo-[2-(tetrahydro-pyran-4-yl)-5,6,7,8-tetrahydro-indolizin-3-yl]-acetyl chloride |
| 24 | [2-(1-Methyl-piperidin-4-yl)-5,6,7,8-tetrahydro-indolizin-3-yl]-oxo-acetyl chloride |

Reference Example 25

4-chloro-2-methoxymethyl-1-nitro-benzene

Sodium hydroxide (1.88 g, 44.0 mmol) in water (15 mL) was added to a solution of (5-chloro-2-nitro-phenyl)-methanol (1.1 g, 5.88 mmol) in dichloromethane (15 mL) and stirred for 10 min. Dimethyl sulfate (1.12 mL, 11.8 mmol) and tetrabutylammonium hydrogen sulfate (100 mg) were added and the mixture stirred vigorously for 8 h at room temperature. The reaction mixture was diluted with dichloromethane and the organic phase was separated, washed with water, brine, dried over anhydrous sodium sulfate, filtered and concentrated under vacuum to give the crude compound. Purification by column chromatography over silica gel (100-200 mesh) using 2% ethyl acetate in petroleum ether as eluent afforded 4-chloro-2-methoxymethyl-1-nitro-benzene (850 mg, 72%) as a pale yellow liquid.

Reference Example 26

The compound set out below was prepared a manner analogous to Reference Example 25 (4-chloro-2-methoxymethyl-1-nitro-benzene).

| Example | Compound |
|---|---|
| 26 | 1-Chloro-2-methoxymethyl-4-nitro-benzene |

Reference Example 27

2-chloro-5-nitro-phenol

A saturated solution of sodium nitrite (1.8 g, 26.0 mmol) in water (12 mL) was added dropwise to a suspension of 2-amino-5-nitro-phenol (2.0 g, 13.0 mmol) in concentrated hydrochloric acid (10 mL) at 0° C. and stirred for 30 min. In another flask, copper (I) chloride (5.15 g, 52.0 mmol) and concentrated hydrochloric acid (20 mL) were heated to between 60 and 70° C. and the diazonium salt solution was added dropwise to this over a period of 30 min. The reaction mixture was heated to 80° C. and stirred for 15 min. It was then cooled to room temperature and ethyl acetate (50 mL) was added and stirred for 5 min. The organic phase was separated and the aqueous phase was extracted with ethyl acetate (2×50 mL). The combined organic phases were washed with water (4×50 mL), brine, dried over anhydrous sodium sulfate and concentrated in vacuo to give a residue which was purified by column chromatography over silica gel (100-200 mesh) using 5% ethyl acetate in petroleum ether as eluent to afford 2-chloro-5-nitro-phenol (2.08 g, 92%) as a crystalline yellow solid.

Reference Example 28

2-benzyloxy-1-chloro-4-nitro-benzene

Benzyl bromide (0.6 mL, 5.04 mmol) was added dropwise to a mixture of 2-chloro-5-nitro-phenol (800 mg, 4.61 mmol) and potassium carbonate (1.27 g, 9.22 mmol) in acetone (20 mL) at room temperature and heated at reflux for 2 h. Inorganic salts were filtered off and washed with acetone (20 mL). The combined filtrate and washings were concentrated in vacuo, the resulting residue then being dissolved in ethyl acetate (25 mL) and washed successively with water (2×20 mL), brine (20 mL), dried over anhydrous sodium sulfate and concentrated in vacuo to yield 2-benzyloxy-1-chloro-4-nitro-benzene (1.20 g, 99%) as a cream solid.

Reference Example 29

1-(4-nitro-phenyl)-piperazine

A solution of 1-chloro-4-nitrobenzene (15 g, 94.5 mmol) in 1-butanol (75 mL) was added over 20-30 minutes to a refluxing solution of anhydrous piperazine (24.4 g, 284 mmol) in 1-butanol (75 mL) and the mixture maintained at reflux overnight. The solvent was removed under reduced pressure to afford a solid, to which was added 2N hydrochloric acid (400 mL). The aqueous layer was washed twice with ethyl acetate, cooled to below 10° C. and basified with a cold solution of 40% sodium hydroxide to pH 10, keeping temperature below 20° C. The mixture was extracted with ethyl acetate (4×200 mL) then the combined organic layers were washed with brine and dried over sodium sulfate. Filtration and concentration under reduced pressure afforded 1-(4-nitro-phenyl)-piperazine (13.7 g, 70%) as a yellow solid.

Reference Example 30

1-(4-nitro-phenyl)-[1,4]diazepane

A solution of homopiperazine (11.4 g, 114 mmol) in 1-butanol (40 mL) was added to a refluxing solution of 1-chloro-4-nitrobenzene (6.0 g, 38 mmol) in 1-butanol (40 mL) over 15 minutes. The mixture was maintained at reflux for 24 hours then cooled to room temperature and extracted with 2N hydrochloric acid. The aqueous layer was basified with potassium carbonate and extracted with ethyl acetate. The organic layer was dried over sodium sulfate and concentrated to afford 1-(4-nitro-phenyl)-[1,4]diazepane (3.5 g, 42%) as a yellow solid.

Reference Example 31

3-[Methyl-(4-nitro-phenyl)-amino]-propionic Acid

Methyl-(4-nitro-phenyl)-amine (3.0 g, 19.7 mmol) and acrylic acid (4.06 mL, 59.2 mmol) were added at 0° C. to a solution of concentrated sulfuric acid (2.15 mL, 39.5 mmol) in water (28 mL). The reaction mixture was heated at 80° C. for 30 min, cooled to room temperature and diluted with water. The precipitated solid was filtered and dried to give a crude product which was purified by washing with diethyl ether and pentane, affording 3-[methyl-(4-nitro-phenyl)-amino]-propionic acid (4.0 g, 91%) as a yellow solid.

Reference Example 32

N-(4,6-Dimethyl-pyridin-2-yl)-N-methyl-3-[methyl-(4-nitro-phenyl)-amino]-propionamide a) Preparation of 3-[methyl-(4-nitro-phenyl)-amino]-propionyl chloride 3-[Methyl-(4-nitro-phenyl)-amino]-propionic acid (1.2 g, 5.35 mmol) in dichloromethane (10 mL) was cooled to 0° C. and thionyl chloride (1.55 mL, 21.4 mmol) was added. The mixture was heated to reflux for 4 h. The solvent was evaporated to give the crude compound which was azeotroped with toluene to remove the traces of thionyl chloride, affording 3-[methyl-(4-nitro-phenyl)-amino]-propionyl chloride (1.15 g, 88%) as a yellow solid.

b) Preparation of N-(4,6-dimethyl-pyridin-2-yl)-N-methyl-3-[methyl-(4-nitro-phenyl)-amino]-propionamide A solution of 3-[methyl-(4-nitro-phenyl)-amino]-propionyl chloride (550 mg, 4.04 mmol) in dichloromethane (5 mL) was cooled to 0° C., triethylamine (1.12 mL, 8.08 mmol) was added followed, after 5 min, by (4,6-dimethyl-pyridin-2-yl)-methyl-amine (1.14 g, 4.73 mmol). The reaction mixture was warmed to room temperature and stirred for 30 min then partitioned between water and dichloromethane. The organic phase was separated, washed with saturated bicarbonate solution, brine, dried over anhydrous sodium sulfate and concentrated under reduced pressure to give a residue which was purified by column chromatography over silica gel (60-120 mesh) using 20% ethyl acetate in hexane as eluent to afford N-(4,6-dimethyl-pyridin-2-yl)-N-methyl-3-[methyl-(4-nitro-phenyl)-amino]-propionamide (600 mg, 43%) as a yellow solid.

Reference Example 33

N-(4,6-Dimethyl-pyridin-2-yl)-N,N-dimethyl-N'-(4-amino-phenyl)-propane-1,3-diamine Borane-dimethylsulfide complex (0.72 mL, 7.02 mmol) was added to a solution of N-(4,6-dimethyl-pyridin-2-yl)-N-methyl-3-[methyl-(4-nitro-phenyl)-amino]-propionamide (600 mg, 1.75 mmol) in tetrahydrofuran (10 mL) at 0° C. The mixture was warmed to room temperature then heated at reflux overnight. After cooling to room temperature the solvent was evaporated in vacuo. The residue was quenched into ice water, extracted with ethyl acetate then the organic phase was washed with water and brine, dried over anhydrous sodium sulfate and concentrated in vacuo. Purification of the residue by column chromatography over silica gel (60-120 mesh) using 10% ethyl acetate in hexane as eluent afforded N-(4,6-dimethyl-pyridin-2-yl)-N,N'-dimethyl-N'-(4-nitrophenyl)-propane-1,3-diamine (350 mg, 61%) as yellow semi solid.

Reference Example 34

N*1*-(4-nitro-phenyl)-ethane-1,2-diamine

A mixture of 1-chloro-4-nitro-benzene (10 g, 64 mmol) and ethane-1,2-diamine (38 mL) was heated at reflux for 4 h. Excess ethane-1,2-diamine was evaporated under reduced pressure and water was added to the residue. The precipitated solid was filtered off and dried under vacuum to afford N*1*-(4-nitro-phenyl)-ethane-1,2-diamine (10.8 g, quantitative).

Reference Example 35

N-(4,6-Dimethyl-pyridin-2-yl)-N'-(4-nitrophenyl)-ethane-1,2-diamine

To a solution of trifluoro-methanesulfonic acid 4,6-dimethyl-pyridin-2-yl ester (prepared according to J. Org. Chem., 63, 10048-51, 1998), using pyridine as base. 0.6 g, 2.35 mmol) in diglyme (2 mL) was added N*1*-(4-nitro-phenyl)-ethane-1,2-diamine (0.51 g, 2.82 mmol). The reaction mixture was heated to 165° C. for 24 h. The resulting reaction mixture was concentrated under reduced pressure and the residue diluted with chloroform. The organic layer was washed with brine and water and dried over sodium sulfate. The solvent was evaporated and the crude residue was purified by column chromatography (60-120 mesh) using 20% ethyl acetate/petroleum ether as eluent to afford N-(4,6-dimethyl-pyridin-2-yl)-N'-(4-nitro-phenyl)-ethane-1,2-diamine (0.38 g, 55%) as a cream solid.

Reference Example 36

N-(4,6-Dimethyl-pyridin-2-yl)-N,N'-dimethyl-N'-(4-nitro-phenyl)-ethane-1,2-diamine A solution of N-(4,6-Dimethyl-pyridin-2-yl)-N'-(4-nitrophenyl)-ethane-1,2-diamine (0.3 g, 1.05 mmol) in THF (8 mL) was cooled to 0° C. Sodium hydride (50% in mineral oil; 0.16 g, 3.3 mmol) was added portionwise and the mixture was stirred for 30 min at r.t. Methyl iodide (0.27 mL) was added dropwise at 0° C. and the mixture was stirred at r.t. for 3 h. The reaction was quenched with ice-cold water and extracted with chloroform (3×50 mL). The combined organic layers were washed with brine and dried over sodium sulfate. Concentration gave a residue which was purified by column chromatography using 15% ethyl acetate/petroleum ether as eluent to afford N-(4,6-dimethyl-pyridin-2-yl)-N,N'-dimethyl-N'-(4-nitro-phenyl)-ethane-1,2-diamine (0.12 g, 38%) as light yellow solid.

Reference Example 37

1-(2-Bromo-ethoxy)-4-nitro-benzene

A mixture of p-nitro-phenol (6.0 g, 43.1 mmol), potassium carbonate (14.9 g, 108 mmol) and 1,2-dibromoethane (24.3 g, 129 mmol) in butanone (80 mL) was heated at reflux for 18 h. The mixture was cooled, the inorganic salts filtered and the filtrate concentrated under vacuum to give a brown viscous liquid, which was partitioned between dichloromethane and water. The organic phase was separated and concentrated in vacuo to obtain a residue which was purified by column chromatography using 4% ethyl acetate in petroleum ether as eluent to afford 1-(2-bromo-ethoxy)-4-nitro-benzene (7.5 g, 70%) as a light yellow solid.

Reference Example 38

2,4-Dimethyl-6-[2-(4-nitro-phenoxy)-ethoxy]-pyridine

A mixture of 2-hydroxy-4,6-dimethylpyridine (1.7 g, 13.8 mmol), potassium carbonate (3.82 g, 27.6 mmol) and 1-(2-bromo-ethoxy)-4-nitro-benzene (4.0 g, 16.6 mmol) in DMF (30 mL) was heated to 120° C. and maintained for 15 h. The mixture was cooled to ambient temperature, filtered and concentrated to give a residue which was purified by column chromatography using 4% ethyl acetate/petroleum ether as eluent to afford 2,4-dimethyl-6-[2-(4-nitro-phenoxy)-ethoxy]-pyridine as yellow solid (530 mg, 11%).

Reference Example 39

The compound set out below was prepared in a manner analogous to Reference Example 38 (2,4-Dimethyl-6-[2-(4-nitro-phenoxy)-ethoxy]pyridine).

| Reference Example | Compound |
|---|---|
| 39 | 2,6-Dimethyl-4-[2-(4-nitro-phenoxy)-ethoxy]-pyridine |

Reference Example 40

1-(2-methyl-allyl)-4-(4-nitrophenyl)-piperazine

To a solution of 1-(4-nitrophenyl)-piperazine (prepared as described in Reference Example 29; 13 g, 63 mmol) in acetonitrile (150 mL) were added, successively, 3-chloro-2-methyl-propene (6.82 g, 75.4 mmol) and triethylamine (17.6 mL, 126 mmol). The mixture was heated at reflux for 8 hours then the solvent was evaporated under reduced pressure to give a residue which was partitioned between water (150 mL) and ethyl acetate (2×100 mL). The combined organic layers were washed twice with water then dried over sodium sulfate. Filtration and concentration afforded 1-(2-methyl-allyl)-4-(4-nitrophenyl)-piperazine (13.2 g, 79%) as a yellow solid.

Reference Example 41

2,2-dimethyl-1-[4-(4-nitro-phenyl)-piperazin-1-yl]-propan-1-one

To an ice-cooled solution of 1-(4-nitro-phenyl)-piperazine (prepared as described in Reference Example 29; 5 g, 24 mmol) in DCM (40 mL) was added pivaloyl chloride (4.36 g, 36.2 mmol) and triethylamine (8.73 mL, 60 mmol) at 0-5° C. The mixture was warmed to room temperature and stirred for 1 hour then diluted with DCM (150 mL), washed with water (2×50 mL) and brine (50 mL), dried over sodium sulfate and concentrated to dryness to afford 2,2-dimethyl-1-[4-(4-nitro-phenyl)-piperazin-1-yl]-propan-1-one (6 g, 85.7%) as a yellow solid.

Reference Example 42

1-(2,2-dimethyl-propyl)-4-(4-nitro-phenyl)-piperazine

A solution of 2,2-dimethyl-1-[4(4-nitro-phenyl)-piperazin-1-yl]-propan-1-one (8.0 g, 27.5 mmol) in THF (100 mL) was added dropwise to a solution of borane-dimethylsulfide complex (16 mL, 166 mmol) in THF (100 mL) over 30 minutes and stirred for 3 h at room temperature. The mixture was quenched with saturated ammonium chloride solution (200 mL) and concentrated to remove organic solvents under reduced pressure (<45° C.). The aqueous layer was extracted with ethyl acetate (3×100 mL) then the combined extracts were washed with water (100 mL) and brine (100 mL), dried over sodium sulfate and concentrated to dryness to afford 1-(2,2-dimethyl-propyl)-4-(4-nitro-phenyl)-piperazine (6 g, 79%) as a yellow solid.

Reference Example 43

1-(4-Nitro-phenyl)-piperidin-4-one

Piperidin-4-one hydrochloride was added to a methanolic solution of sodium methoxide (prepared from anhydrous methanol (50 mL) and sodium metal (0.85 g, 37 mmol)) and heated at reflux for 2 h then concentrated to dryness in vacuo. The residue was dissolved in acetonitrile (100 mL), then potassium carbonate (10.22 g, 74 mmol) and 1-fluoro-4-nitro-benzene (3.92 mL, 37 mmol) were added and the mixture was heated at reflux overnight. The solvent was evaporated in vacuo, the residue being washed with water then 50% diethyl ether/petroleum ether and dried in vacuo to afford 1-(4-nitro-phenyl)-piperidin-4-one (3.01 g, 37%) as a yellow solid.

Reference Example 44

1-(4-Amino-phenyl)-piperidin-4-one

A solution of 1-(4-nitro-phenyl)-piperidin-4-one (2.8 g, 12.7 mmol) in a mixture of 1:4 dioxane: methanol (100 mL) was hydrogenated over Raney nickel (1 g) under balloon pressure at ambient temperature overnight. The mixture was filtered through Celite and the filtrate was concentrated under vacuum. The resulting solid was washed with petroleum ether (2×10 mL) and dried to afford 1-(4-amino-phenyl)-piperidin-4-one (1.34 g, 55%).

Reference Example 45

1-Phenyl-piperidin-4-one

A solution of 1-(4-amino-phenyl)-piperidin-4-one (1.34 g, 7.05 mmol) in 50% hydrochloric acid (10 mL) was stirred at ambient temperature for 15 min. The reaction mixture was cooled to 0° C. and a solution of sodium nitrite (1.46 g) in water (5 mL) added and stirred for 30 min. To this reaction mixture was added cold 30-32% hypophosphorus acid (10 mL), the mixture then being warmed to ambient temperature and stirred for 2 h. The reaction mixture was neutralised with saturated sodium bicarbonate solution and extracted with ethyl acetate. The organic layer was washed with water, brine solution, dried over anhydrous sodium sulfate and concentrated to give a residue which was purified by column chromatography over silica gel (60-120 mesh) using 17% ethyl acetate in petroleum ether as eluent to afford 1-phenyl-piperidin-4-one (0.18 g, 15%) as a liquid.

Reference Example 46

1-Phenyl-piperidin-4-one Oxime

A mixture of 1-phenyl-piperidin-4-one (180 mg, 1.03 mmol) and hydroxylamine hydrochloride (142 mg, 2.06 mmol) in methanol (10 mL) was heated at reflux for 6 h. The solvent was evaporated and the residue diluted with water. The mixture was extracted with ethyl acetate then the organic phase was washed with water, brine, dried over anhydrous sodium sulfate and concentrated to afford 1-phenyl-piperidin-4-one oxime (0.18 g, 92%) as a liquid.

Reference Example 47

1-Phenyl-piperidin-4-ylamine

A solution of 1-phenyl-piperidin-4-one oxime (0.18 g, 0.95 mmol) in methanol (10 mL) was hydrogenated over Raney nickel (0.15 g) under balloon pressure at ambient temperature for 6 h. The reaction mixture was filtered through Celite and the filtrate was concentrated in vacuo. The semi-solid residue was treated with n-pentane (2×5 mL) and dried to afford 1-phenyl-piperidin-4-ylamine (0.13 g, 78%) as a solid.

Reference Example 48

2-chloro-4,6-dimethylpyridine

2-Amino-4,6-dimethyl-pyridine (4 g, 32.7 mmol) was dissolved in conc. hydrochloric acid (50 mL) and cooled to 0° C. A solution of sodium nitrite (3.39 g, 49.1 mmol) in water (20 mL) was added dropwise, followed by a solution of sodium chloride (3.8 g, 65 mmol) in water (20 mL). The mixture was stirred for 30 min. then basified with 20% sodium hydroxide solution and extracted with ethyl acetate. The combined extracts were washed with brine, dried over sodium sulfate and concentrated in vacuo to give a residue which was purified by column chromatography on silica gel (60-120 mesh) using 5% ethyl acetate/petroleum ether as eluent to afford 2-chloro-4,6-dimethyl-pyridine (1 g, 22%) as a solid.

Reference Examples 49 and 50

The compounds set out below were prepared in a manner analogous to Reference Example 48 (2-chloro-4,6-dimethylpyridine).

| Reference Example | Compound |
| --- | --- |
| 49 | 2-Chloro-6-ethyl-pyridine |
| 50 | 2-Chloro-4-ethyl-pyridine |

Reference Example 51

2-Chloro-4-methyl-pyridine 1-oxide

40% meta-chloroperbenzoic acid (13.5 g, 31.4 mmol) was added at ambient temperature to a solution of 2-chloro-4-methyl-pyridine (2.0 g, 1.5 mmol) in chloroform (20 mL) and heated at reflux for 24 h. After allowing to cool, the mixture was washed with water followed by sodium bicarbonate solution. The separated organic phase was further washed with water and brine, dried over anhydrous sodium sulfate and concentrated to give a residue which was purified by column chromatography over silica gel (60-120 mesh) using 10% methanol in ethyl acetate as eluent to afford 2-chloro-4-methyl-pyridine 1-oxide (1.0 g, 45%) as a deep brown oily liquid.

Reference Example 52

2,6-dichloro-4-methyl-pyridine

A mixture of 2-chloro-4-methyl-pyridine 1-oxide (1.0 g, 7.0 mmol) and phosphorus oxychloride (10 mL) was heated at reflux for 4 h. The volatiles were evaporated and the residue dissolved in ethyl acetate. The solution was washed with ice-water followed by sodium bicarbonate solution. The organic phase was again washed with water, brine solution, dried over anhydrous sodium sulfate and concentrated to obtain a residue which was purified by column chromatography over silica gel (60-120 mesh) using petroleum ether as eluent to afford 2,6-dichloro-4-methyl-pyridine (491 mg, 43%) as a white solid.

Reference Example 53

2-chloro-6-methoxy-4-methyl-pyridine

A solution of 2,6-dichloro-4-methyl-pyridine (250 mg, 1.5 mmol) in methanol (2 mL) was added to a solution of sodium methoxide (prepared from sodium (71 mg, 3.0 mmol) and anhydrous methanol (20 mL)) and heated at reflux for 48 h. The solvent was evaporated and the residue partitioned between water and dichloromethane. The organic layer was separated, washed with water, brine, dried over anhydrous sodium sulfate and concentrated to afford 2-chloro-6-methoxy-4-methyl-pyridine (150 mg, 61%) as a pale orange oily liquid.

Reference Example 54

4-(6-chloro-pyridin-3-yl-methyl)-morpholine a) Preparation of 5-bromomethyl-2-chloro-pyridine
N-bromosuccinimide (6.1 g, 3.44 mmol) and benzoyl peroxide (218 mg, 0.09 mmol) were added successively to a solution of 2-chloro-5-methyl-pyridine (4.0 g, 3.13 mmol) in carbon tetrachloride (20 mL) and refluxed for 90 min. The reaction mixture was cooled to room temperature, water added and the organic layer separated. The organic layer was washed successively with water, brine, dried over anhydrous sodium sulfate and filtered. The resultant solution of 5-bromomethyl-2-chloro-pyridine was used as such for the next step.
b) Preparation of 4-(6-chloro-pyridin-3-yl-methyl)-morpholine
Morpholine (7.0 g, 8.8 mmol) was added to the solution of 5-bromomethyl-2-chloro-pyridine in carbon tetrachloride (20 mL) and stirred at room temperature for 6 h. Water was added to the reaction mixture and the separated organic layer was washed with water, brine, dried over anhydrous sodium sulfate, filtered and concentrated to afford the crude product. Purification by column chromatography using silica gel (60-120 mesh) and ethyl acetate as eluent afforded 4-(6-chloro-pyridin-3-yl-methyl)-morpholine (1.2 g, 21%) as a brown oily liquid.

Reference Example 55

2-Bromo-6-methyl-pyridine 1-oxide

Hydrogen peroxide (30%, 1.76 mL, 17.4 mmol) was added to a solution of 2-bromo-6-methyl-pyridine (1.0 g, 5.80 mmol) in acetic acid (20 mL), and heated for 24 h at 90° C. The reaction mixture was cooled to ambient temperature, and partitioned between dichloromethane and water. The aqueous phase was separated and extracted with dichloromethane. The combined organic phases were washed thoroughly with water and dried over anhydrous sodium sulfate. Concentration in vacuo afforded 2-bromo-6-methyl-pyridine 1-oxide (820 mg, 75%) as a brown liquid which was used in the next step without further purification.

Reference Example 56

2-Bromo-6-methyl-4-nitro-pyridine 1-oxide

Concentrated nitric acid (4 mL) was added to cold concentrated sulfuric acid (7 mL). 2-Bromo-6-methyl-pyridine 1-oxide (820 mg, 4.36 mmol) was added to this and then heated at 70° C. for 4 h. The mixture was cooled and poured slowly into ice-cold water (100 mL) and basified to pH ~8 with sodium bicarbonate solution. This was extracted with ethyl acetate (4×50 mL) then the combined organic layers were dried over anhydrous sodium sulfate and concentrated to give a residue which was purified by washing with pentane (50 mL) to afford 2-bromo-6-methyl-4-nitro-pyridine 1-oxide (0.41 g, 40%) as a free flowing yellow solid.

Reference Example 57

2-Bromo-4-methoxy-6-methyl-pyridine 1-oxide

Sodium methoxide (94 mg, 1.74 mmol) was added to a solution of 2-bromo-6-methyl-4-nitro-pyridine 1-oxide (408 mg, 1.74 mmol) in dry methanol (20 mL) at 0° C., then warmed to ambient temperature and maintained overnight. The volatiles were evaporated in vacuo and the residue extracted with chloroform (5×40 mL). The combined organic layers were washed with water, dried over anhydrous sodium sulfate and concentrated to afford a residue which was purified by column chromatography over silica gel (60-120 mesh) using 3% methanol in chloroform as eluent to afford 2-bromo-4-methoxy-6-methyl-pyridine 1-oxide (0.32 g, 84%) as a white solid.

Reference Example 58

1-(4-Methoxy-6-methyl-1-oxy-pyridin-2-yl)-4-(4-nitro-phenyl)-piperazine

A mixture of 2-bromo-4-methoxy-6-methyl-pyridine 1-oxide (320 mg, 1.46 mmol), 1-(4-nitro-phenyl)-piperazine (302 mg, 1.46 mmol) and potassium carbonate (403 mg, 2.92 mmol) in diglyme (5 mL) was heated at reflux for 16 h. The mixture was cooled to ambient temperature and filtered then the filtrate was concentrated to dryness in vacuo. The residue was washed successively with pentane (2×10 mL), dichloromethane (10 mL), and ether (2×10 mL) to afford 1-(4- methoxy-6-methyl-1-oxy-pyridin-2-yl)-4-(4-nitro-phenyl)-piperazine (350 mg, 70%) as a free flowing yellow solid.

Reference Example 59

1-(4-Methoxy-6-methyl-pyridin-2-yl)-4-(4-nitro-phenyl-piperazine

Phosphorus trichloride (0.27 mL, 3.05 mmol) was added dropwise to a solution of 1-(4-methoxy-6-methyl-1-oxy-pyridin-2-yl)-4-(4-nitro-phenyl)-piperazine (350 mg, 1.02 mmol) in dry chloroform (20 mL) and heated at reflux overnight. The reaction mixture was diluted with chloroform and quenched slowly into saturated sodium carbonate solution at 0° C. The organic phase was separated and the aqueous phase extracted with chloroform. The combined organic phases were dried over anhydrous sodium sulfate and concentrated in vacuo to afford 1-(4-methoxy-6-methyl-pyridin-2-yl)-4-(4-nitro-phenyl)-piperazine (166 mg, 50%) as a yellow solid.

Reference Example 60

1-(4,6-dimethyl-pyridin-2-yl)-4-(4-nitro-phenyl)-[1,4]diazepane

A solution of 1-(4-nitro-phenyl)-[1,4]diazepane (1.5 g, 6.78 mmol) in dry toluene (30 mL) was purged with argon gas for 1 hour then 2-chloro-4,6-dimethylpyridine (0.960 g, 6.78 mmol) and caesium carbonate (13.3 g, 40.7 mmol) were added and the reaction mixture again purged with argon gas for 1 hour.
Meanwhile, a suspension of palladium (II) acetate (60 mg, 0.27 mmol) and (2'-dicyclohexylphosphanyl-biphenyl-2-yl)-dimethyl-amine (53 mg, 0.13 mmol) in dry THF (2 mL) was purged with argon gas for 1 hour then added to reaction mixture. The mixture was heated to reflux for 15 hours then filtered and concentrated under vacuum to give a residue which was purified by flash column chromatography on silica (60-120 mesh), eluting with 1:1 ethyl acetate/petroleum ether, to afford 1-(4,6-dimethyl-pyridin-2-yl)-4-(4-nitro-phenyl)-[1,4]diazepane (940 mg, 43%) as a brown solid.

Reference Examples 61 to 65

The compounds set out below were prepared in a manner analogous to Reference Example 60 (1-(4,6-dimethyl-pyridin-2-yl)-4-(4-nitro-phenyl)-[1,4]diazepane).

Reference Example 66

1-(4,6-dimethyl-pyridin-2-yl)-piperazine

A solution of 2-chloro-4,6-dimethylpyridine (30 g, 0.212 mol) in diglyme (100 mL) was added over 25-30 min. to a refluxing solution of anhydrous piperazine (147 g, 1.70 mol) in diglyme (150 mL). Heating was continued for 18 h (whereby TLC showed absence of 2-chloro-4,6-dimethylpyridine), then the mixture was cooled to room temperature and diluted with water (3 L). Sodium chloride (50 g) was added and the solution was extracted with ethyl acetate (300 mL×3); the combined extracts were washed with brine (200 mL), dried over anhydrous sodium sulfate and concentrated in vacuo (up to 110° C. & ~15 mmHg; to remove maximum diglyme) to afford 1-(4,6-dimethyl-pyridin-2-yl)-piperazine (42 g, 103.3%, the G.C. spectrum showed 86.4% product, 10.7% diglyme, and 2.1% dimer.)

Reference Example 67

4',6'-Dimethyl-2,3,5,6-tetrahydro-[1,2']bipyridinyl-4-one

Caesium carbonate (48.05 g, 141.3 mmol) was added to a solution of piperidin-4-one hydrochloride (7.6 g, 56.5 mmol) in toluene (20 mL) and stirred for 15-20 min under argon. A solution of 2-chloro-4,6-dimethyl-pyridine (4.0 g, 28.3 mmol) in tetrahydrofuran (10 mL) was added dropwise followed successively by palladium acetate (63 mg, 0.28 mmol) and (±)-(1,1'-binaphthalene-2,2'-diyl)bis(diphenylphosphine) (BINAP) (0.174 g, 0.28 mmol). The reaction mixture was heated at reflux overnight then cooled to 0° C., diluted with water and extracted with ethyl acetate. The organic phase was washed with brine, dried over anhydrous sodium sulfate and concentrated in vacuo to give a residue which was purified by column chromatography over silica gel (60-120 mesh) using 10% ethyl acetate in hexane as eluent to afford 4',6'-dimethyl-2,3,5,6-tetrahydro-[1,2']bipyridinyl-4-one (450 mg, 8%) as a yellow solid.

Reference Example 68

The compound set out below was prepared in a manner analogous to Reference Example 67 (4',6'-Dimethyl-2,3,5,6-tetrahydro-[1,2']bipyridinyl-4-one).

| Reference Example | Starting materials | Compound |
|---|---|---|
| 61 | 1-(4-nitro-phenyl)-piperazine and 2-chloro-6-methoxy-4-methyl-pyridine. | 1-(6-Methoxy-4-methyl-pyridin-2-yl)-4-(4-nitro-phenyl)-piperazine |
| 62 | 1-(4-nitro-phenyl)-piperazine and 2-chloro-6-ethyl-pyridine | 1-(6-Ethyl-pyridin-2-yl)-4-(4-nitro-phenyl)-piperazine |
| 63 | 1-(4-nitro-phenyl)-piperazine and 2-chloro-5-methyl-pyridine | 1-(5-Methyl-pyridin-2-yl)-4-(4-nitro-phenyl)-piperazine |
| 64 | 1-(4-Nitro-phenyl)-piperazine and 2-chloro-4-ethyl-pyridine | 1-(4-Ethyl-pyridin-2-yl)-4-(4-nitro-phenyl)-piperazine |
| 65 | 1-(4-Nitro-phenyl)-piperazine and 4-(6-chloro-pyridin-3-ylmethyl)-morpholine | 4-{6-[4-(4-nitro-phenyl)-piperazin-1-yl]-pyridin-3-yl-methyl}-morpholine |

| Reference Example | Starting materials | Compound |
|---|---|---|
| 68 | 1-(4,6-Dimethyl-pyridin-2-yl)-piperazine and 4-chloro-2-methoxymethyl-1-nitro-benzene | 1-(4,6-Dimethyl-pyridin-2-yl)-4-(3-methyl-4-nitro-phenyl)-piperazine |

Reference Example 69

1-(4,6-dimethyl-pyridin-2-yl)-4-(4-nitro-phenyl)-piperazine

To a stirred solution of 1-(4,6-dimethyl-pyridin-2-yl)-piperazine (42 g, equivalent to 36 g after correcting for purity, 0.188 mol) in diglyme (150 mL) was added potassium carbonate (52.3 g, 0.376 mol) and stirred at room temperature for 15 min. A solution of 1-chloro-4-nitro-benzene (44 g, 0.282 mol) in diglyme (100 mL) was added and the whole heated at reflux for 16 h. Another portion of 1-chloro-4-nitro-benzene (15.8 g, 0.1 mol) in diglyme (50 mL) was added and reflux continued for a further 18 h. The mixture was cooled to room temperature and filtered to remove salts, which were washed with ethyl acetate (100 mL×2). The filtrate was concentrated to remove ethyl acetate, and most of diglyme was removed by high vacuum distillation (~7 mmHg) to give a solid, which was dissolved in DCM (700 mL). 6N HCl (500 mL) was added and the solid that precipitated was filtered off. The organic phase of the filtrate was separated and treated again with 6N HCl (2×500 mL). Each time the resulting precipitated solid was filtered off; after three treatments the DCM layer no longer contained product.

The solid (42 g) was taken in water (500 mL), basified to pH~9 with ammonium hydroxide and extracted with DCM (3×250 mL), washed with brine solution (2×150 mL), dried and evaporated to dryness to yield the product (first crop, 27 g, 46%). The combined aqueous layers were washed with DCM (300 mL), basified with ammonium hydroxide solution to pH ~9 and extracted with DCM (250 mL×3). The organic layers were combined, washed with brine solution (2×150 mL), dried over $Na_2SO_4$, and concentrated to dryness to afford a residue, which was purified over silica gel (60-120 mesh) using 11% ethyl acetate in pet ether as eluent to afford a second crop (5.5 g, 9%). Total yield: 32.5 g (55%) of 1-(4,6-dimethyl-pyridin-2-yl)-4-(4-nitro-phenyl)-piperazine

Reference Examples 70 to 74

The compounds set out below were prepared in a manner analogous to Reference Example 69 (1-(4,6-dimethyl-pyridin-2-yl)-4-(4-nitro-phenyl)-piperazine) by reacting 1-(4,6-dimethyl-pyridin-2-yl)-piperazine with the appropriate aryl chloride.

| Reference Example | Compound |
|---|---|
| 70 | 1-(4,6-Dimethyl-pyridin-2-yl)-4-(3-methyl-4-nitro-phenyl)-piperazine |
| 71 | 1-(4,6-Dimethyl-pyridin-2-yl)-4-(2-methoxymethyl-4-nitro-phenyl)-piperazine |
| 72 | {2-[4-(4,6-Dimethyl-pyridin-2-yl)-piperazin-1-yl]-5-nitro-phenyl}-methanol |
| 73 | 1-(2-Chloro-4-nitro-phenyl)-4-(4,6-dimethyl-pyridin-2-yl)-piperazine |
| 74 | 5-[4-(4,6-Dimethyl-pyridin-2-yl)-piperazin-1-yl]-2-nitro-phenylamine |

Reference Example 75

1-(4,6-Dimethyl-pyridin-2-yl)-4-(2-methyl-4-nitro-phenyl)-piperazine

Caesium carbonate (10.19 g, 31.38 mmol), 1-chloro-2-methyl-4-nitro-benzene (0.98 g, 5.75 mmol) and 1-(4,6-dimethyl-pyridin-2-yl)-piperazine (1.0 g, 5.23 mmol) were taken in toluene (35 mL) and degassed with argon for 15 min. A slurry of 2-dicyclophosphino-2'-(N,N-dimethylamino)-biphenyl (0.2 g, 0.52 mmol) and palladium acetate (0.116 g, 0.52 mmol) in toluene (5 mL) was added, the mixture degassed for another 10 min and then heated at reflux for 16 h. The mixture was cooled to room temperature and filtered, washing with ethyl acetate. The filtrate was washed with 2N hydrochloric acid, water, and brine, dried over anhydrous sodium sulfate, filtered and concentrated under vacuum to obtain the crude compound. Purification by column chromatography over silica gel (100-200 mesh) using 0-12% ethyl acetate in petroleum ether as eluent gave 1-(4,6-dimethyl-pyridin-2-yl)-4-(2-methyl-4-nitro-phenyl)-piperazine (0.463 g, 27%) as a solid.

Reference Example 76

The compound set out below was prepared in a manner analogous to Reference Example 75 (1-(4,6-dimethyl-pyridin-2-yl)-4-(2-methyl-4-nitro-phenyl)-piperazine) by reaction of 1-(4,6-dimethyl-pyridin-2-yl)-piperazine with the appropriate aryl chloride.

| Reference Example | Compound |
|---|---|
| 76 | 1-(2-Benzyloxy-4-nitro-phenyl)-4-(4,6-dimethyl-pyridin-2-yl)-piperazine |

Reference Example 77

2-[4-(4,6-Dimethyl-pyridin-2-yl)-piperazin-1-yl]-5-nitro-phenol

Trifluoroacetic acid (5 mL) was added to 1-(2-benzyloxy-4-nitro-phenyl)-4-(4,6-dimethyl-pyridin-2-yl)-piperazine (720 mg, 1.72 mmol) at between 0 and 5° C. followed by concentrated hydrochloric acid (2 mL). The mixture was heated at reflux overnight then cooled to between 0 and 5° C. and quenched with saturated sodium bicarbonate solution (30 mL). Chloroform (30 mL) was added and the mixture stirred for 15 min. The organic phase was separated and the aqueous phase was extracted with chloroform (30 mL). The combined organic phases were washed successively with water (2×30 mL) then brine (30 mL), dried over anhydrous sodium sulfate and concentrated in vacuo to give a residue. Trituration with petroleum ether afforded 2-[4-(4,6-dimethyl-pyridin-2-yl)-piperazin-1-yl]-5-nitro-phenol (510 mg, 90%) as a brownish-yellow solid.

Reference Example 78

Acetic acid 2-[4-(4,6-dimethyl-pyridin-2-yl)-piperazin-1-yl]-5-nitro-phenyl ester Triethylamine (1.0 mL, 7.17 mmol) was added to a solution of 2-[4-(4,6-dimethyl-pyridin-2-yl)-piperazin-1-yl]-5-nitro-phenol (500 mg, 1.52 mmol) in dry dichloromethane (20 mL) followed by the dropwise addition of acetyl chloride (0.2 mL, 2.80 mmol). After stirring for 15 min water was added and the mixture warmed to room temperature. The organic phase was separated and the aqueous phase was extracted with dichloromethane (2×30 mL). The combined organic phases were successively washed with water (2×30 mL) then brine (2×30 mL), dried over anhydrous sodium sulfate and concentrated in vacuo. The residue was triturated with 5% dichloromethane in petroleum ether (2×20 mL) to afford acetic acid 2-[4-(4,6-dimethyl-pyridin-2-yl)-piperazin-1-yl]-5-nitro-phenyl ester (365 mg, 65%) as a pale brownish-yellow solid.

Reference Example 79

4-(3-{2-[4-(4,6-Dimethyl-pyridin-2-yl)-piperazin-1-yl]-5-nitro-benzyloxy}-propyl)-morpholine Aqueous sodium hydroxide (50% w/w, 10 g, 125 mmol) and tetrabutylammonium hydrogen sulfate (0.20 g) were added successively to a solution of {2-[4-(4,6-dimethyl-pyridin-2-yl)-piperazin-1-yl]-5-nitro-phenyl}-methanol (0.50 g, 1.46 mmol) in toluene (5 mL). The mixture was heated to reflux with vigorous stirring for 45 min then 4-(3-chloro-propyl)-morpholine (0.50 g, 3.00 mmol) was added and reflux continued for 28 h. The reaction mixture was cooled and the organic phase separated. The aqueous phase was extracted with ethyl acetate (3×5 mL). The organic phases were combined, washed with water and brine, dried over anhydrous sodium sulfate, filtered and concentrated under vacuum to give a residue which was purified by preparative TLC eluting with 2% methanol in chloroform to afford 4-(3-{2-[4-(4,6-dimethyl-pyridin-2-yl)-piperazin-1-yl]-5-nitro-benzyloxy}-propyl)-morpholine (550 mg, 80%) as a solid.

Reference Examples 80 and 81

The compounds set out below were prepared in a manner analogous to Reference Example 79:

| Reference Example | Compound |
|---|---|
| 80 | (2-{2-[4-(4,6-Dimethyl-pyridin-2-yl)-piperazin-1-yl]-5-nitro-benzyloxy}-ethyl)-dimethyl-amine |
| 81 | 1-(4,6-Dimethyl-pyridin-2-yl)-4-[4-nitro-2-(3-piperazin-1-yl-propoxymethyl)-phenyl]-4-methyl-piperazine |

Reference Example 82

1-(3-Chloro-4-nitro-phenyl)-4-(4,6-dimethyl-pyridin-2-yl)-piperazine

50% aqueous hydrochloric acid (30 mL) was chilled to −20° C., 5-[4-(4,6-dimethyl-pyridin-2-yl)-piperazin-1-yl]-2-nitro-phenylamine (1.4 g, 4.28 mmol) was added and the reaction mixture stirred for 15 min. A solution of sodium nitrite (350 mg, 5.14 mmol) in water (8 mL) was added and the reaction mixture stirred for 15 min. This solution was added dropwise to a cooled solution of copper (I) chloride (635 mg, 6.42 mmol) in 50% hydrochloric acid (20 mL) over a period of 20 min and stirred for a further 10 min before basifying with saturated sodium carbonate solution. The mixture was extracted with ethyl acetate then the organic phase was washed with water and brine, dried over anhydrous sodium sulfate and concentrated under vacuum to give a crude residue. Purification by column chromatography over silica gel (100-200 mesh) using 8% ethyl acetate in petroleum ether as eluent afforded 1-(3-chloro-4-nitro-phenyl)-4-(4,6-dimethyl-pyridin-2-yl)-piperazine (800 mg, 54%) as a yellow solid.

Reference Example 83

2-bromomethyl-1-methoxy-3-nitro-benzene

N-bromosuccinimide (590 mg, 3.30 mmol) was added to a solution of 1-methoxy-2-methyl-3-nitro-benzene (500 mg, 3.0 mmol) in carbon tetrachloride (5 mL) followed by a catalytic amount of dibenzoyl peroxide (25 mg). The reaction mixture was heated at reflux for 3 h then cooled to room temperature and poured into water. The organic phase was separated, washed with water (2×20 mL), dried over the anhydrous sodium sulfate and concentrated in vacuo to afford 2-bromomethyl-1-methoxy-3-nitro-benzene (640 mg, 86%) as a solid.

Reference Example 84

(2-methoxy-6-nitro-phenyl)-acetonitrile

Sodium cyanide (165 mg, 3.36 mmol) was added to a solution of 2-bromomethyl-1-methoxy-3-nitro-benzene (680 mg, 2.56 mmol) in ethanol (5 mL) and the mixture was heated at reflux overnight. The solvent was removed in vacuo, water (30 mL) was added and the mixture was extracted with dichloromethane (25 mL). The organic phase was washed with water (2×20 mL), brine (20 mL), dried over anhydrous sodium sulfate and concentrated under vacuum. The crude compound was purified by column chromatography over silica gel (100-200 mesh) using 8% ethyl acetate in petroleum ether to afford (2-methoxy-6-nitro-phenyl)-acetonitrile (300 mg, 61%).

Reference Example 85

(2-methoxy-6-nitro-phenyl)-acetic Acid Ethyl Ester

Sulfuric acid (1 mL) was slowly added to a solution of (2-methoxy-6-nitro-phenyl)-acetonitrile (200 mg, 1.04 mmol) in 95% ethanol (2 mL). The mixture was heated at reflux overnight then quenched into ice cold water and extracted with diethyl ether (10 mL). The organic phase was washed with water (2×10 mL), dried over anhydrous sodium sulfate and concentrated in vacuo to afford (2-methoxy-6-nitro-phenyl)-acetic acid ethyl ester (180 mg, 72%).

Reference Example 86

2-(2-Methoxy-6-nitro-phenyl)-ethanol

Diisobutylaluminium hydride (20 wt % in toluene; 2.38 g, 16.8 mmol) was added to a solution of (2-methoxy-6-nitrophenyl)-acetic acid ethyl ester (1.0 g, 4.18 mmol) in tetrahydrofuran (8 mL) at −5° C. The reaction mixture was stirred for 1 h at 0° C. and then poured into 1N hydrochloric acid solution. The mixture was extracted with ethyl acetate (30 mL) then the separated organic phase was washed with water (2×30 mL), brine (25 mL), dried over anhydrous sodium sulfate and concentrated in vacuo to afford 2-(2-methoxy-6-nitro-phenyl)-ethanol (780 mg, 94%).

Reference Example 87

4-Nitro-2,3-dihydro-benzofuran 2-(2-Methoxy-6-nitro-phenyl)-ethanol (700 mg, 3.55 mmol) was dissolved in polyphosphoric acid (3 mL) and heated at 120° C. for 1 h. After cooling to r.t. ice-water water was added and the mixture extracted with ethyl acetate. The organic phase was washed with water (2×20 mL), dried over anhydrous sodium sulfate and concentrated in vacuo to afford 4-nitro-2,3-dihydro-benzofuran (400 mg, 68%).

Reference Example 88

4-(4-amino-phenyl)-4',6'-dimethyl-3,4,5,6-tetrahydro-2H-[1,2']-bipyridinyl-4-ol n-Butyl lithium (1 mL, 1.6 M in hexane, 1.6 mmol) was added dropwise to a solution of 2-(4-bromo-phenyl)-1,1,1,3,3,3-hexamethyl-disilazane (0.7 g, 2.20 mmol) in dry diethyl ether (10 mL) and stirred at room temperature for 15 min then cooled in an ice bath. A solution of 4',6'-dimethyl-2,3,5,6-tetrahydro-[1,2']bipyridinyl-4-one (0.3 g, 1.47 mmol) in dry tetrahydrofuran (15 mL) was added and the resulting mixture heated at 50° C. for 2.5 h. The reaction mixture was brought to room temperature and stirred overnight, then cooled to 0° C. and quenched into ammonium chloride solution. The mixture was extracted with ethyl acetate and the organic phase was washed with water, brine, dried over anhydrous sodium sulfate, filtered and concentrated in vacuo to yield the crude compound, to which was added 2N HCl and the resulting mixture was stirred overnight at room temperature. The pH of the solution was adjusted to pH 10 with dilute sodium hydroxide then the mixture was extracted with chloroform. The organic phase was dried over anhydrous sodium sulfate, filtered and concentrated to dryness to give a viscous red oil which was purified by washing with pentane (5×10 mL) to afford 4-(4-amino-phenyl)-4',6'-dimethyl-3,4,5,6-tetrahydro-2H-[1,2']-bipyridinyl-4-ol (0.25 g, 57%).

Reference Example 89

4-[4-(2-Methyl-allyl)-piperazin-1-yl]-phenylamine

Tin (II) chloride dihydrate (67.0 g, 297 mmol) was added in portions to a solution of 1-(2-methyl-allyl)-4-(4-nitro-phenyl)-piperazine (prepared as described in Reference Example 40, 13 g, 50 mmol) in ethyl acetate (200 mL) at room temperature. The mixture was heated to reflux for 4 hours then the solvent was evaporated under reduced pressure. The resulting residue was diluted with water and basified with 10% sodium hydroxide solution to pH ~10 then extracted with ethyl acetate (4×100 mL). The combined organic layers were washed twice with saturated brine then dried over sodium sulfate. Filtration and concentration in vacuo gave a gummy mass which was washed repeatedly with small volumes of 1:3 ether/hexane to afford a solid. This was slurried with hexane, filtered and dried under vacuum at room temperature to afford 1-(2-methyl-allyl)-4-(4-amino-phenyl)-piperazine (8.5 g, 74%) as light yellow solid.

Reference Example 90

4-[4-(4,6-dimethyl-pyridin-2-yl)-[1,4]diazepan-1-yl]-phenylamine

To a solution of 1-(4,6-dimethyl-pyridin-2-yl)-4-(4-nitro-phenyl)-[1,4]diazepane (940 mg, 2.88 mmol) in ethyl acetate (25 mL) was added stannous chloride (3.90 g, 17.3 mmol) and ethanol (5 mL). The reaction mixture was heated to reflux for 15 hours then cooled to room temperature, basified with triethylamine and filtered. The filtrate was concentrated under reduced pressure to afford 4-[4-(4,6-dimethyl-pyridin-2-yl)-[1,4]diazepan-1-yl]-phenylamine (850 mg, 99%) as a brown solid.

Reference Examples 91 and 92

The compounds set out below were prepared in a manner analogous to Reference Example 89 (1-(2-methyl-allyl)-4-(4-amino-phenyl)-piperazine) and Reference Example 90 (4-[4-(4,6-dimethyl-pyridin-2-yl)-[1,4]diazepan-1-yl]-phenylamine):

| Reference Example | Compound |
| --- | --- |
| 91 | 4-[2-(4,6-Dimethyl-pyridin-2-yloxy)-ethoxy]-phenylamine |
| 92 | 2-Chloro-4-[4-(4,6-dimethyl-pyridin-2-yl)-piperazin-1-yl]-phenylamine |

Reference Example 93

4-[4-(2,2-dimethyl-propyl)-piperazin-1-yl-]-phenylamine 1-(2,2-Dimethyl-propyl)-4-(4-nitro-phenyl)-piperazine (4 g, 14.4 mmol) was hydrogenated over Raney nickel (500 mg) in methanol (150 mL) at atmospheric pressure and room temperature for 3 hours. The mixture was filtered through Celite and the filtrate concentrated to dryness to afford 4-[4-(2,2-dimethyl-propyl)-piperazin-1-yl-]-phenylamine (3 g, 84%) as a yellow solid.

Reference Example 94

4-[4-(4,6-dimethyl-pyridin-2-yl)-piperazin-1-yl]-phenyl amine

A slurry of 1-(4,6-dimethyl-pyridin-2-yl)-4-(4-nitro-phenyl)-piperazine (27 g, 86.5 mmol) in methanol (1 L) was hydrogenated over Raney nickel (8 g) at 70-75 psi and room temperature in a Parr hydrogenation apparatus until no starting material was observed on TLC. The mixture was filtered through Celite and the filtrate concentrated in vacuo to afford 4-[4-(4,6-dimethyl-pyridin-2-yl)-piperazin-1-yl]-phenyl amine (22.2 g, 91%) as a solid which needed no further purification and was used as such in the next step.

Reference Examples 95 to 113

The compounds set out below were prepared in a manner analogous to Reference Example 93 (4-[4-(2,2-dimethyl-propyl)-piperazin-1-yl-]-phenyl amine) and Reference Example 94 (4-[4-(4,6-dimethyl-pyridin-2-yl)-piperazin-1-yl]-phenyl amine):

| Reference Example | Compound |
|---|---|
| 95 | N-{2-[(4,6-Dimethyl-pyridin-2-yl)-methyl-amino]-ethyl}-N-methyl-benzene-1,4-diamine |
| 96 | 4-[4-(4-Methoxy-6-methyl-pyridin-2-yl)-piperazin-1-yl]-phenylamine |
| 97 | 4-[4-(6-Methoxy-4-methyl-pyridin-2-yl)-piperazin-1-yl]-phenylamine |
| 98 | 4-[2-(2,6-Dimethyl-pyridin-4-yloxy)-ethoxy]-phenylamine |
| 99 | 4-[4-(6-Ethyl-pyridin-2-yl)-piperazin-1-yl]-phenylamine |
| 100 | 4-[4-(5-methyl-pyridin-2-yl)-piperazin-1-yl]-phenyl amine |
| 101 | 4-[4-(4-ethyl-pyridin-2-yl)-piperazin-1-yl]-phenyl amine |
| 102 | 4-[4-(5-morpholin-4-yl-methyl-pyridin-2-yl)-piperazin-1-yl]-phenyl amine |
| 103 | N-{3-[(4,6-Dimethyl-pyridin-2-yl)-methyl-amino]-propyl}-N-methyl-benzene-1,4-diamine |
| 104 | 4-[4-(4,6-Dimethyl-pyridin-2-yl)-piperazin-1-yl]-2-methyl-phenylamine |
| 105 | 4-[4-(4,6-Dimethyl-pyridin-2-yl)-piperazin-1-yl]-3-methyl-phenylamine |
| 106 | 4-[4-(4,6-Dimethyl-pyridin-2-yl)-piperazin-1-yl]-3-methoxymethyl-phenylamine |
| 107 | 4-[4-(4,6-Dimethyl-pyridin-2-yl)-piperazin-1-yl]-2-methoxymethyl-phenylamine |
| 108 | 4-[4-(4,6-Dimethyl-pyridin-2-yl)-piperazin-1-yl]-3-(3-morpholin-4-yl-propoxymethyl)-phenylamine |
| 109 | 3-(2-Dimethylamino-ethoxymethyl)-4-[4-(4,6-dimethyl-pyridin-2-yl)-piperazin-1-yl]-phenylamine |
| 110 | 4-[4-(4,6-Dimethyl-pyridin-2-yl)-piperazin-1-yl]-3-[3-(4-methyl-piperazin-1-yl)-propoxymethyl]-phenylamine |
| 111 | 3-Chloro-4-[4-(4,6-dimethyl-pyridin-2-yl)-piperazin-1-yl]-phenylamine |
| 112 | 5-Amino-2-[4-(4,6-dimethyl-pyridin-2-yl)-piperazin-1-yl]-phenol (from acetic acid 2-[4-(4,6-dimethyl-pyridin-2-yl)-piperazin-1-yl]-5-nitro-phenyl ester with concomitant ester hydrolysis) |
| 113 | 2,3-Dihydro-benzofuran-4-ylamine |

Example 1

N-{4-[4(2-methyl-allyl)-piperazin-1-yl]-phenyl}-2-oxo-2-(2-phenyl-5,6,7,8-tetrahydro-indolizin-3-yl)-acetamide To an ice-cold solution of 4-[4-(2-methyl-allyl)-piperazin-1-yl]-phenylamine (prepared as described in Reference Example 89, 500 mg, 2.16 mmol) and triethylamine (0.6 mL, 4.32 mmol) in dry DCM (12 mL) was added a solution of oxo-(2-phenyl-5,6,7,8-tetrahydro-indolizin-3-yl)-acetyl chloride (prepared as described in Reference Example 21, 726 mg, 2.52 mmol) in DCM (5 mL). The mixture was warmed to room temperature and stirred for 30 min then diluted with DCM, washed successively with water, sodium bicarbonate solution and brine, then dried over sodium sulfate. Concentration gave a residue which was purified by preparative TLC using ethyl acetate and hexane (3:7) as eluent to afford N-{4-[4-(2-methyl-allyl)-piperazin-1-yl]-phenyl}-2-oxo-2-(2-phenyl-5,6,7,8-tetrahydro-indolizin-3-yl)-acetamide (220 mg, 21%) as a yellow powder.

Example 2

N-{4-[4-(2,2-dimethyl-propyl)-piperazin-1-yl]-phenyl}-2-oxo-2-(2-phenyl-5,6,7,8-tetrahydro-indolizin-3-yl)-acetamide To an ice-cold solution of 4-[4-(2,2-dimethyl-propyl)-piperazin-1-yl]-phenylamine (prepared as described in Reference Example 93, 300 mg, 1.21 mmol) and triethylamine (0.33 mL, 2.4 mmol) in dry DCM (12 mL) was added a solution of oxo-(2-phenyl-5,6,7,8-tetrahydro-indolizin-3-yl)-acetyl chloride (prepared as described in Reference Example 21, 407 mg, 1.41 mmol) in DCM (5 mL). The mixture was warmed to room temperature and stirred for 30 min then diluted with DCM, washed successively with water, sodium bicarbonate solution and brine, then dried over sodium sulfate. Concentration gave a residue which was purified by preparative TLC using ethyl acetate and hexane (3:7) as eluent to afford N-{4-[4-(2,2-dimethyl-propyl)-piperazin-1-yl]-phenyl}-2-oxo-2-(2-phenyl-5,6,7,8-tetrahydro-indolizin-3-yl)-acetamide (220 mg, 36%) as a yellow powder.

Example 3

N-{4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide Oxo-(2-phenyl-5,6,7,8-tetrahydro-indolizin-3-yl)-acetyl chloride (prepared as described in Reference Example 21, 40 g, 0.14 mol) was added portion-wise to a solution of 4-[4-(4,6-dimethyl-pyridin-2-yl)-piperazin-1-yl]-phenylamine (prepared as described in Reference Example 94, 18 g, 63.8 mmol) in pyridine (150 mL). The reaction mass was stirred for 1 hour then quenched slowly into cold water (3 L). The precipitated solid was filtered and washed with water (3×50 mL). The solid was dissolved in chloroform (200 mL) and washed successively with bicarbonate solution (3×200 mL) and brine (200 mL). The chloroform layer was separated, diluted with chloroform (800 mL), and to this was added neutral alumina (150 g) and charcoal (5 g). The mixture was stirred for 2 hours at room temperature then filtered through celite. The treatment was repeated with another 75 g of neutral alumina with over night stirring. Filtration and concentration gave a solid which was dissolved in toluene (500 mL) and extracted with 25% aqueous acetic acid solution (3×500 mL). The combined aqueous layers were basified with 25% ammonium hydroxide solution (2 L) to pH ~7 and extracted with diethyl ether (2×300 mL). The combined ether extracts were washed with bicarbonate solution (2×200 mL), brine (200 mL), dried over sodium sulfate and concentrated in vacuo to give a solid. This was further purified by passing through a short silica pad (60-120 silica gel) eluting with 30% ethyl acetate in chloroform. After concentration, the solid was dissolved at reflux in ethanol (300 mL). The solution was cooled to 0° C., and stirred for 15 minutes, whereupon the precipitated solid was filtered and dried on the sinter. Further drying at 60° C. under high vacuum afforded the title compound N-{4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide (10.4 g, 30.5%) as a yellow powder.

Example 4

2-(2-cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide A solution of 4-[4-(4,6-dimethyl-pyridin-2-yl)-piperazin-1-yl]-phenylamine (prepared as described in Reference Example 94; 0.20 g, 0.71 mmol) and triethylamine (0.3 mL, 2.1 mmol) in THF (5 mL) was cooled to 0° C. A solution of (2-cyclopentyl-5,6,7,8-tetrahydro-indolizin-3-yl)-oxo-acetyl chloride (prepared as described in Reference Example 22, 0.24 g, 0.85 mmol) in THF (2 mL) was added and the mixture stirred under $N_2$ atmosphere at 0° C. for 1 h and then at room temperature for 1 h. The mixture was quenched with sodium bicarbonate solution and extracted twice with ethyl acetate. The combined organic phases were washed with water and brine, dried over sodium sulfate and concentrated in vacuo. The residue was purified by flash chromatography on silica gel (60-120 mesh) eluting with 12% ethyl acetate/chloroform to afford 2-(2-cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide (0.17 g, 46%) as a solid.

Example 5

N-{4-[4-(4,6-dimethyl-pyridin-2-yl)-[1,4]diazepan-1-yl]-phenyl}-2-oxo-2-(2-phenyl-5,6,7,8-tetrahydro-indolizin-3-yl)-acetamide To a solution of 4-[4-(4,6-dimethyl-pyridin-2-yl)-[1,4]diazepan-1-yl]-phenyl amine (prepared as described in Reference Example 90, 800 mg, 2.70 mmol) in DCM (30 mL) was added oxo-(2-phenyl-5,6,7,8-tetrahydro-indolizin-3-yl)-acetyl chloride (prepared as described in Reference Example 21, 930 mg, 3.24 mmol) and triethylamine (0.75 mL, 5.4 mmol). The mixture was stirred for 2 h at room temperature then concentrated in vacuo to give a residue which was purified by flash chromatography on silica gel (60-120 mesh) eluting with 30% ethyl acetate/n-hexane to afford N-{4-[4-(4,6-dimethyl-pyridin-2-yl)-[1,4]diazepan-1-yl]-phenyl}-2-oxo-2-(2-phenyl-5,6,7,8-tetrahydro-indolizin-3-yl)-acetamide (500 mg, 35%) as a yellow solid.

Example 6

N-{4-[4-(4,6-dimethyl-pyridin-2-yl)-piperazin-1-yl]-phenyl}-N-methyl-2-oxo-2-(2-phenyl-5,6,7,8-tetrahydro-indolizin-3-yl)-acetamide Sodium hydride (55% dispersion in oil, 24 mg, 0.56 mmol) was added to an ice-cold solution of N-{4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide (prepared as described in Example 3, 200 mg, 0.37 mmol) in THF, and stirred for 10 minutes at 0° C. Methyl iodide (0.036 mL, 0.56 mmol) was added, the mixture warmed to room temperature and stirred for 30 min. The solvent was evaporated and the residue partitioned between ice-water and DCM. The organic layer was separated and washed successively with water, sodium bicarbonate solution and brine, dried over sodium sulfate and concentrated to give a residue. This was dissolved in the minimum amount of DCM and re-precipitated by addition of petroleum ether to afford N-{4-[4-(4,6-dimethyl-pyridin-2-yl)-piperazin-1-yl]-phenyl}-N-methyl-2-oxo-2-(2-phenyl-5,6,7,8-tetrahydro-indolizin-3-yl)-acetamide (120 mg, 58%) as light yellow powder.

Examples 7 to 32

The compounds set out below were prepared in a manner analogous to Examples 1 to 5 using intermediates generated in the Reference Examples.

| Example | Compound |
|---|---|
| 7 | N-[4-({2-[(4,6-Dimethyl-pyridin-2-yl)-methyl-amino]-ethyl}-methyl-amino)-phenyl]-2-oxo-2-(2-phenyl-5,6,7,8-tetrahydro-indolizin-3-yl)-acetamide |
| 8 | N-{4-[4-(4-Methoxy-6-methyl-pyridin-2-yl)-piperazin-1-yl]-phenyl}-2-oxo-2-(2-phenyl-5,6,7,8-tetrahydro-indolizin-3-yl)-acetamide |
| 9 | N-{4-[2-(4,6-Dimethyl-pyridin-2-yloxy)-ethoxy]-phenyl}-2-oxo-2-(2-phenyl-5,6,7,8-tetrahydro-indolizin-3-yl)-acetamide |
| 10 | N-{4-[4-(4,6-Dimethyl-pyridin-2-yl)-piperazin-1-yl]-phenyl}-2-oxo-2-[2-(tetrahydro-pyran-4-yl)-5,6,7,8-tetrahydro-indolizin-3-yl]-acetamide |
| 11 | N-{4-[4-(4,6-Dimethyl-pyridin-2-yl)-piperazin-1-yl]-phenyl}-2-[2-(1-methyl-piperidin-4-yl)-5,6,7,8-tetrahydro-indolizin-3-yl]-2-oxo-acetamide |
| 12 | 2-Oxo-N-(1-phenyl-piperidin-4-yl)-2-(2-phenyl-5,6,7,8-tetrahydro-indolizin-3-yl)-acetamide |
| 13 | N-{4-[4-(6-Methoxy-4-methyl-pyridin-2-yl)-piperazin-1-yl]-phenyl}-2-oxo-2-(2-phenyl-5,6,7,8-tetrahydro-indolizin-3-yl)-acetamide |
| 14 | N-{4-[2-(2,6-Dimethyl-pyridin-4-yloxy)-ethoxy]-phenyl}-2-oxo-2-(2-phenyl-5,6,7,8-tetrahydro-indolizin-3-yl)-acetamide |
| 15 | N-{4-[4-(6-Ethyl-pyridin-2-yl)-piperazin-1-yl]-phenyl}-2-oxo-2-(2-phenyl-5,6,7,8-tetrahydro-indolizin-3-yl)-acetamide |
| 16 | N-{4-[4-(5-Methyl-pyridin-2-yl)-piperazin-1-yl]-phenyl}-2-oxo-2-(2-phenyl-5,6,7,8-tetrahydro-indolizin-3-yl)-acetamide |

-continued

| Example | Compound |
|---------|----------|
| 17 | N-{4-[4-(4-Ethyl-pyridin-2-yl)-piperazin-1-yl]-phenyl}-2-oxo-2-(2-phenyl-5,6,7,8-tetrahydro-indolizin-3-yl)-acetamide |
| 18 | N-{4-[4-(5-Morpholin-4-ylmethyl-pyridin-2-yl)-piperazin-1-yl]-phenyl}-2-oxo-2-(2-phenyl-5,6,7,8-tetrahydro-indolizin-3-yl)-acetamide |
| 19 | N-[4-({3-[(4,6-Dimethyl-pyridin-2-yl)-methyl-amino]-propyl}-methyl-amino)-phenyl]-2-oxo-2-(2-phenyl-5,6,7,8-tetrahydro-indolizin-3-yl)-acetamide |
| 20 | N-{4-[4-(4,6-Dimethyl-pyridin-2-yl)-piperazin-1-yl]-2-methyl-phenyl}-2-oxo-2-(2-phenyl-5,6,7,8-tetrahydro-indolizin-3-yl)-acetamide |
| 21 | N-[4-(4-Hydroxy-4',6'-dimethyl-3,4,5,6-tetrahydro-2H-[1,2']bipyridinyl-4-yl)-phenyl]-2-oxo-2-(2-phenyl-5,6,7,8-tetrahydro-indolizin-3-yl)-acetamide |
| 22 | N-{4-[4-(4,6-Dimethyl-pyridin-2-yl)-piperazin-1-yl]-3-methyl-phenyl}-2-oxo-2-(2-phenyl-5,6,7,8-tetrahydro-indolizin-3-yl)-acetamide |
| 23 | N-{4-[4-(4,6-Dimethyl-pyridin-2-yl)-piperazin-1-yl]-3-methoxymethyl-phenyl}-2-oxo-2-(2-phenyl-5,6,7,8-tetrahydro-indolizin-3-yl)-acetamide |
| 24 | N-{4-[4-(4,6-Dimethyl-pyridin-2-yl)-piperazin-1-yl]-2-methoxymethyl-phenyl}-2-oxo-2-(2-phenyl-5,6,7,8-tetrahydro-indolizin-3-yl)-acetamide |
| 25 | N-{4-[4-(4,6-Dimethyl-pyridin-2-yl)-piperazin-1-yl]-3-[3-(4-methyl-piperazin-1-yl)-propoxymethyl]-phenyl}-2-oxo-2-(2-phenyl-5,6,7,8-tetrahydro-indolizin-3-yl)-acetamide |
| 26 | N-[4-[4-(4,6-Dimethyl-pyridin-2-yl)-piperazin-1-yl]-3-(3-morpholin-4-yl-propoxymethyl)-phenyl]-2-oxo-2-(2-phenyl-5,6,7,8-tetrahydro-indolizin-3-yl)-acetamide |
| 27 | N-{3-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide |
| 28 | N-Naphthalen-1-yl-2-oxo-2-(2-phenyl-5,6,7,8-tetrahydro-indolizin-3-yl)-acetamide |
| 29 | N-{3-(2-Dimethylamino-ethoxymethyl)-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide |
| 30 | N-{2-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide |
| 31 | N-{4-[4-(4,6-Dimethyl-pyridin-2-yl)-piperazin-1-yl]-3-hydroxy-phenyl}-2-oxo-2-(2-phenyl-5,6,7,8-tetrahydro-indolizin-3-yl)-acetamide |
| 32 | N-(2,3-Dihydro-benzofuran-6-yl)-2-oxo-2-(2-phenyl-5,6,7,8-tetrahydro-indolizin-3-yl)-acetamide |

| Example No. | NMR Data | MS Spectrum |
|---|---|---|
| 1 | $^1$H (400 MHz, CDCl$_3$): δ 8.15 (s, 1H), 7.33-7.28 (m, 2H), 7.25-7.18 (m, 3H), 7.06 (d, 2H), 6.79 (d, 2H), 6.1 (s, 1H), 4.9 (d, 2H), 4.35 (t, 2H), 3.15 (m, 4H), 2.9 (m, 4H), 2.5 (m, 4H), 2.0 (m, 2H), 1.92 (d, 2H), 1.75 (s, 3H). | 483 (M + H) |
| 2 | $^1$H (400 MHz, CDCl$_3$): δ 8.15 (s, 1H), 7.40-7.15 (m, 5H), 7.10 (d, 2H), 6.79 (d, 2H), 6.10 (s, 1H), 4.35 (t, 2H), 3.10 (m, 4H), 2.90 (t, 2H), 2.65 (m, 4H), 2.15 (m, 2H), 2.10-1.80 (m, 4H), 0.85 (s, 9H) | 499 (M + H) |
| 3 | $^1$H (400 MHz, CDCl$_3$): δ 8.14 (s, 1H), 7.31 (d, 2H), 7.26-7.22 (m, 3H), 7.09 (d, 2H), 6.83 (d, 2H), 6.38 (s, 1H), 6.31 (s, 1H), 6.08 (s, 1H), 4.33 (t, 2H), 3.65 (t, 4H), 3.22 (t, 4H), 2.88 (t, 2H), 2.37 (s, 3H), 2.23 (s, 3H), 2.05-1.97 (m, 2H), 1.91-1.85 (m, 2H) | 534 (M + H) |
| 4 | $^1$H (400 MHz, CDCl$_3$): δ 8.33 (broad s, 1H), 7.54 (d, 2H), 6.97 (d, 2H), 6.39 (s, 1H), 6.32 (s, 1H), 5.93 (s, 1H), 4.21 (t, 2H), 3.68 (t, 4H), 3.34 (m, 1H), 3.27 (t, 4H), 2.79 (t, 2H), 2.38 (s, 3H), 2.24 (s, 3H), 2.00 (m, 2H), 1.90 (m, 2H), 1.80 (m, 2H), 1.71 (m, 2H), 1.57 (m, 2H), 1.49 (m, 2H) | 526 (M + H) |
| 5 | $^1$H (400 MHz, CDCl$_3$): δ 8.07 (s, 1H), 7.32 (d, 2H), 7.28-7.22 (m, 3H), 7.01 (d, 2H), 6.58 (d, 2H), 6.24 (s, 1H), 6.09 (d, 2H), 4.32 (t, 2H), 3.87 (t, 2H), 3.58 (t, 2H), 3.46-3.40 (m, 4H), 2.87 (t, 2H), 2.32 (s, 3H), 2.19 (s, 3H), 2.07-1.98 (m, 4H), 1.86 (t, 2H) | 548 (M + H) |
| 6 | $^1$H (400 MHz, CDCl$_3$): δ 7.44-7.34 (m, 5H), 6.83-6.74 (m, 4H), 6.39 (s, 1H), 6.31 (m, 1H), 5.78 (s, 1H), 4.18 (t, 2H), 3.64 (t, 4H), 3.23 (t, 4H), 2.71 (d, 2H), 2.68 (s, 3H), 2.37 (s, 3H), 2.23 (s, 3H), 1.85 (m, 2H), 1.73 (m, 2H). | 548 (M + H) |
| 7 | $^1$H (400 MHz, CDCl$_3$): δ 8.09 (s, 1H), 7.34-7.31 (m, 2H), 7.28-7.22 (m, ~3H, solvent overlap), 7.05-7.01 (m, 2H), 6.70 (d, 2H), 6.28 (s, 1h), 6.08 (s, 1H), 6.04 (s, 1H), 4.33 (t, 2H), 3.69 (t, 2H), 3.48 (t, 2H), 2.98 (s, 3H), 2.92 (s, 3H), 2.89-2.86 (m, 2H), 2.38 (s, 3H), 2.19 (s, 3H), 2.06-1.97 (m, 2H), 1.89-1.85 (m, 2H). | 536 (M + H) |
| 8 | $^1$H (400 MHz, CDCl$_3$): δ 8.15 (s, 1H), 7.35-7.30 (m, 2H), 7.26-7.23 (m, 3H), 7.09 (d, 2H), 6.83 (d, 2H), 6.15 (s, 1H), 6.09 (s, 1H), 5.98 (s, 1H), 4.32 (t, 2H), 3.80 (s, 3H), 3.65 (s, 4H), 3.22 (s, 4H), 2.88 (t, 2H), 2.38 (s, 3H), 2.00 (m, 2H), 1.86 (m, 2H) | 550 (M + H) |
| 9 | $^1$H (400 MHz, CDCl$_3$): δ 8.13 (s, 1H), 7.32-7.29 (d, 2H), 7.24-7.20 (m, 3H), 7.08 (d, 2H), 6.80 (d, 2H), 6.56 (s, 1H), 6.39 (s, 1H), 6.08 (s, 1H), 4.61 (t, | 510 (M + H) |

| Example No. | NMR Data | MS Spectrum |
|---|---|---|
| | 2H), 4.33 (t, 2H), 4.25 (t, 2H), 2.88 (t, 2H), 2.36 (s, 3H), 2.23 (s, 3H), 2.04-1.97 (m, 2H), 1.90-1.84 (m, 2H) | |
| 10 | $^1$H (400 MHz, CDCl$_3$): δ 8.37 (s, 1H), 7.56 (d, 2H), 6.98 (d, 2H), 6.39 (s, 1H), 6.33 (s, 1H), 5.95 (s, 1H), 4.22 (t, 2H), 3.97 (m, 2H), 3.69 (t, 4H), 3.41 (t, 2H), 3.28 (t, 4H), 3.16 (m, 1H), 2.81 (t, 2H), 2.38 (s, 3H), 2.24 (s, 3H), 1.94 (m, 2H), 1.84-1.62 (m, ~6H, water overlap). | 542 (M + H) |
| 11 | $^1$H (400 MHz, CDCl$_3$): δ 8.35 (broad s, 1H), 7.56 (d, 2H), 7.00 (d, 2H), 6.40 (s, 1H), 6.33 (s, 1H), 5.94 (s, 1H), 4.21 (t, 2H), 3.69 (t, 4H), 3.29 (t, 4H), 2.89-2.86 (m, 3H), 2.80 (t, 2H), 2.38 (s, 3H), 2.25 (s, 3H), 2.24 (s, 3H), 1.97-1.71 (m, 10H) | 555 (M + H) |
| 12 | $^1$H (400 MHz, CDCl$_3$): δ 7.33-7.26 (m, 5H), 7.24-7.22 (m, 2H), 6.90 (d, 2H), 6.83 (t, 1H), 6.28 (d, 1H), 6.04 (s, 1H), 4.28 (t, 2H), 3.50 (m, 3H), 2.86 (m, 2H), 2.75 (t, 2H), 1.98 (m, 2H), 1.85 (m, 2H), 1.76 (d, 2H), 1.47-1.41 (m, 2H) | 428 (M + H) |
| 13 | $^1$H (400 MHz, CDCl$_3$): δ 8.15 (s, 1H), 7.32-7.30 (m, 2H), 7.27-7.21 (m, 3H), 7.09 (d, 2H), 6.83 (d, 2H), 6.08 (s, 1H), 6.04 (s, 1H), 5.95 (s, 1H), 4.33 (t, 2H), 3.86 (s, 3H), 3.65 (t, 4H), 3.21 (t, 4H), 2.88 (t, 2H), 2.23 (s, 3H), 2.04-1.99 (m, 2H), 1.88-1.85 (m, 2H). | 550 (M + H) |
| 14 | $^1$H (400 MHz, CDCl$_3$): δ 8.15 (s, 1H), 7.31 (d, 2H), 7.24-7.20 (m, overlaps with solvent, ~3H), 7.10 (d, 2H), 6.80 (d, 2H), 6.54 (s, 2H), 6.09 (s, 1H), 4.35-4.26 (m, 6H), 2.88 (t, 2H), 2.48 (s, 6H), 2.00 (m, 2H), 1.87 (m, 2H) | 510 (M + H) |
| 15 | $^1$H (400 MHz, CDCl$_3$): δ 8.15 (s, 1H), 7.42 (t, 1H), 7.31 (d, 2H), 7.26-7.21 (m, overlaps with solvent, ~3H), 7.09 (d, 2H), 6.84 (d, 2H), 6.53-6.48 (m, 2H), 6.09 (s, 1H), 4.33 (t, 2H), 3.68 (t, 4H), 3.23 (t, 4H), 2.88 (t, 2H), 2.68 (q, 2H), 2.00 (d, 2H), 1.87 (d, 2H), 1.27 (t, 3H) | 534 (M + H) |
| 16 | $^1$H (400 MHz, CDCl$_3$): δ 8.15 (s, 1H), 8.04 (s, 1H), 7.35-7.30 (m, 3H), 7.26-7.21 (m, overlaps with solvent ~3H), 7.09 (d, 2H), 6.83 (d, 2H), 6.63 (d, 1H), 6.09 (s, 1H), 4.33 (t, 2H), 3.62 (t, 4H), 3.23 (t, 4H), 2.88 (t, 2H), 2.21 (s, 3H), 2.04-1.97 (m, 2H), 1.90-1.86 (m, 2H) | 520 (M + H) |
| 17 | $^1$H (400 MHz, CDCl$_3$): δ 8.17 (s, 1H), 8.10 (d, 1H), 7.32 (d, 2H), 7.25-7.21 (m, overlaps with solvent, ~2H), 7.09 (d, 2H), 6.83 (d, 2H), 6.54 (m, 2H), 6.08 (s, 1H), 4.32 (t, 2H), 3.69 (t, 4H), 3.23 (t, 4H), 2.88 (t, 2H), 2.58 (q, 2H), 1.99 (m, 2H), 1.86 (m, 2H), 1.25 (t, 3H) | 534 (M + H) |
| 18 | $^1$H (400 MHz, CDCl$_3$): δ 8.15 (s, 1H), 8.10 (d, 1H), 7.51-7.48 (dd, 1H), 7.32-7.30 (m, 2H), 7.26-7.21 (m, overlaps with solvent, ~3H), 7.09 (d, 2H), 6.83 (d, 2H), 6.67 (d, 1H), 6.08 (s, 1H), 4.33 (t, 2H), 3.70-3.66 (m, 8H), 3.38 (s, 2H), 3.23 (t, 4H), 2.88 (t, 2H), 2.42 (s, 4H), 2.08-1.87 (m, 2H), 1.86-1.84 (m, 2H) | 605 (M + H) |
| 19 | $^1$H (400 MHz, CDCl$_3$): δ 8.11 (s, 1H), 7.33 (d, 2H), 7.27-7.23 (m, overlaps with solvent, ~3H), 7.02 (d, 2H), 6.57 (d, 2H), 6.28 (s, 1H), 6.10-6.09 (m, 2H), 4.34 (t, 2H), 3.58 (t, 2H), 3.31 (t, 2H), 3.00 (s, 3H), 2.90-2.88 (m, 5H), 2.35 (s, 3H), 2.19 (s, 3H), 2.09 (m, 2H), 1.89-1.83 (m, 4H) | 550 (M + H) |
| 20 | $^1$H (400 MHz, CDCl$_3$): δ 8.08 (s, 1H), 7.34-7.26 (m, 5H), 7.09 (d, 1H), 6.74 (d, 1H), 6.68 (dd, 1H), 6.38 (s, 1H), 6.30 (s, 1H), 6.08 (s, 1H), 4.33 (t, 2H), 3.64 (t, 4H), 3.21 (t, 4H), 2.88 (t, 2H), 2.37 (s, 3H), 2.25 (s, 3H), 2.23 (s, 3H), 2.00 (m, 2H), 1.87 (m, 2H). | 548 (M + H) |
| 21 | $^1$H (400 MHz, CDCl$_3$): δ 8.27 (s, 1H), 7.35 (d, 2H), 7.31 (d, 2H), 7.25-7.22 (m, 3H), 7.15 (d, 2H), 6.34 (s, 1H), 6.33 (s, 1H), 6.09 (s, 1H), 4.33 (t, 2H), 4.20 (t, 2H), 3.37 (t, 2H), 3.29 (t, 2H), 2.38 (s, 3H), 2.22 (s, 3H), 2.10 (m, 2H), 2.00 (m, 2H), 1.87 (m, 2H), 1.78 (d, 2H) | 549 (M + H) |
| 22 | $^1$H (400 MHz, CDCl$_3$): δ 8.12 (s, 1H), 7.32-7.23 (m, overlaps with solvent, ~5H), 6.98-6.95 (m, 2H), 6.89 (d, 2H), 6.37 (s, 1H), 6.31 (s, 1H), 6.08 (s, 1H), 4.33 (t, 2H), 3.62 (m, 4H), 2.34 (m, 4H), 2.88 (t, 2H), 2.37 (s, 3H), 2.28 (s, 3H), 2.23 (s, 3H), 2.00 (m, 2H), 1.88 (m, 2H) | 548 (M + H) |
| 23 | $^1$H (400 MHz, CDCl$_3$): δ 8.21 (s, 1H), 7.32-7.30 (m, 2H), 7.25-7.16 (m, 5H), 6.95 (d, 1H), 6.38 (s, 1H), 6.31 (s, 1H), 6.09 (s, 1H), 4.50 (s, 2H), 4.33 (t, 2H), 3.63 (s, 4H), 3.42 (s, 3H), 2.97 (t, 4H), 2.89 (t, 2H), 2.38 (s, 3H), 2.23 (s, 3H), 2.00 (m, 2H), 1.88 (m, 2H) | 578 (M + H) |
| 24 | $^1$H (400 MHz, CDCl$_3$): δ 9.28 (s, 1H), 7.35-7.33 (m, 2H), 7.25-7.21 (m, overlaps with solvent, ~4H), 6.76 (m, 2H), 6.38 (s, 1H), 6.31 (s, 1H), 6.07 (s, 1H), 4.48 (s, 2H), 4.35 (t, 2H), 3.65 (m, 4H), 3.47 (s, 3H), 3.21 (m, 4H), 2.87 (t, 2H), 2.37 (s, 3H), 2.23 (s, 3H), 1.99 (m, 2H), 1.88 (m, 2H) | 578 (M + H) |
| 25 | $^1$H (400 MHz, CDCl$_3$): δ 8.14 (s, 1H), 7.32-7.30 (m, 2H), 7.26-7.20 (m, overlaps with solvent, ~4H), 7.13-7.10 (m, 1H), 6.70 (d, 1H), 6.34 (s, 1H), 6.25 (s, 1H), 6.08 (s, 1H), 4.33 (t, 2H), 3.96 (t, 2H), 3.52 (m, 6H), 2.88 (t, 2H), 2.57-2.51 (m, 14H), 2.36 (s, 3H), 2.29 (s, 3H), 2.21 (s, 3H), 2.03-1.90 (m, 4H), 1.87 (m, 2H) | 704 (M + H) |
| 26 | $^1$H (400 MHz, CDCl$_3$): δ 8.15 (s, 1H), 7.31 (dd, 2H), 7.24-7.20 (m, 3H), 7.14-7.11 (m, 2H), 6.71 (d, 1H), 6.35 (s, 1H), 6.25 (s, 1H), 6.08 (s, 1H), 4.33 (t, 2H), 3.98 (t, 2H), 3.72 (t, 4H), 3.54 (broad s, 6H), 2.88 (t, 2H), 2.57 (broad s, 2H), 2.52 (t, 2H), 2.46 (m, 4H), 2.35 (s, 3H), 2.21 (s, 3H), 2.02-1.86 (m, 6H) | 691 (M + H) |
| 27 | $^1$H (400 MHz, CDCl$_3$): δ 8.14 (s, 1H), 7.31-7.25 (m, overlaps with solvent, ~5H), 7.19 (d, 1H), 7.05-7.02 (dd, 1H), 6.92 (d, 1H), 6.39 (s, 1H), 6.31 (s, 1H), 6.10 (s, 1H), 4.33 (t, 2H), 3.67 (broad s, 4H), 3.09 (broad s, 4H), 2.88 (t, 2H), 2.37 (s, 3H), 2.24 (s, 3H), 2.04-1.98 (m, 2H), 1.93-1.86 (m, 2H) | 568 (M + H) |
| 28 | $^1$H (400 MHz, CDCl$_3$): δ 8.85 (broad s, 1H), 7.91 (d, 1H), 7.84 (d, 1H), 7.63 (d, 1H), 7.56-7.48 (m, 2H), 7.39-7.31 (m, 4H), 7.26-7.24 (m, overlaps with | 395 (M + H) |

| Example No. | NMR Data | MS Spectrum |
|---|---|---|
| | solvent, ~3H), 6.12 (s, 1H), 4.39 (t, 2H), 2.90 (t, 2H), 2.02 (m, 2H) 1.90 (m, 2H) | |
| 29 | $^1$H (400 MHz, CDCl$_3$): δ 8.14 (s, 1H), 7.32-7.30 (m, 2H), 7.24-7.22 (m, 3H), 7.14-7.10 (m, 2H), 6.71 (d, 1H), 6.34 (s, 1H), 6.25 (s, 1H), 6.08 (s, 1H), 4.33 (t, 2H), 4.03 (t, 2H), 3.52 (m, 6H), 2.88 (t, 2H), 2.72 (t, 2H), 2.56 (t, 4H), 2.36 (s, 3H), 2.33 (s, 6H), 2.21 (s, 3H), 1.99 (m, 2H), 1.88 (m, 2H) | 635 (M + H) |
| 30 | $^1$H (400 MHz, CDCl$_3$): δ 8.60 (s, 1H), 7.49 (d, 1H), 7.32-7.21 (m, overlaps with solvent, ~5H), 6.91 (d, 1H), 6.69 (dd, 1H), 6.39 (s, 1H), 6.30 (s, 1H), 6.09 (s, 1H), 4.35 (t, 2H), 3.64 (t, 4H), 3.22 (t, 4H), 2.88 (t, 2H), 2.37 (s, 3H), 2.23 (s, 3H), 2.01 (m, 2H), 1.89 (m, 2H) | 566 (M − H) |
| 31 | $^1$H (400 MHz, DMSO-d$_6$): δ 10.16 (s, 1H), 8.94 (s, 1H), 7.26-7.25 (m, 2H), 7.14-6.99 (m, 3H), 6.87 (d, 1H), 6.72 (d, 1H), 6.59 (dd, 1H), 6.46 (s, 1H), 6.36 (s, 1H), 6.05 (s, 1H), 4.29 (t, 2H), 3.57 (s, 4H), 2.93 (s, 4H), 2.85 (t, 2H), 2.26 (s, 3H), 2.18 (s, 3H), 1.99 (m, 2H), 1.80 (m, 2H) | 550 (M + H) |
| 32 | $^1$H (400 MHz, CDCl$_3$): δ 8.12 (broad s, 1H), 7.32-7.23 (m, overlaps with solvent, ~5H), 6.99 (t, 1H), 6.81 (d, 1H), 6.55 (d, 1H), 6.09 (s, 1H), 4.55 (t, 2H), 4.32 (t, 2H), 3.03 (t, 2H), 2.89 (t, 2H), 2.00 (m, 2H), 1.87 (m, 2H) | 387 (M + H) |

Example 33

Measurement of Minimum Inhibitory Concentrations (MICs)

Between 1 and 5 mgs of compound were accurately weighed out into a sterile Eppendorf tube. The compound was dissolved in DMSO to give a solution containing 5 mg/mL. Tubes were stored at −20° C. until required.

On the day of testing thawed solutions were vortex mixed to ensure homogeneity. 30 µL of solution was removed and added to 570 µL of sterile water in a separate sterile Eppendorf. The thoroughly mixed solution was used to prepare a series of doubling dilutions in water, in a deep well plate. Thirteen replicate plates were prepared using a Minitrak by aspirating 204 from each well into eleven clear polystyrene 96 well plates.

Spores of *Aspergillus* spp. (*Aspergillus fumigatus* [two strains], *Aspergillus terreus* [two strains], *Aspergillus niger* and *Aspergillus flavus*) were harvested from cultures grown on Sabarauds agar for 5 days, and resuspended in PBS/Tween 80 to approx 1×10$^7$ cfu/mL. Each organism suspension was diluted in YAG medium (1% glucose, 1% ammonium chloride and 0.5% yeast extract) to 0.5-2×10$^4$ cfu/mL. 80 µL of an organism suspension was added to each well of the plate containing drug dilutions.

This produced MIC plates with a drug range 50-0.05 mg/L and organism inocula of 1-2×10$^4$ cfu/mL for *Aspergillus* spp. All plates were incubated for 24 hrs at 35° C. Growth was assessed by monitoring the optical density at 485 nm for each well. The MIC of a compound is the lowest drug concentration that inhibits growth of an organism by >70% compared with a drug free control. MICs are recorded as mg/L. In cases where the MIC of an organism is >=0.05 mg/L the MIC is repeated using a concentration range of 0.5-0.0005 mg/L. Other growth media can be used for susceptibility testing, and the activity of the described compounds was also assessed in RPMI medium containing 2% glucose, and 0.135M MOPS buffer. MIC tests in YAG medium have more clear-cut endpoints and have slightly lower MICs than those performed in RPMI medium.

The following organisms were tested: *Aspergillus flavus*, *Aspergillus fumigatus* AF293 and AF210, *Aspergillus niger* and *Aspergillus terreus* AT4 and AT49.

Other fungi including *Absidia coiymbifera*; *Acremonium* spp; *Alternaria alternata*; *Aspergillus nidulans*; *Aspergillus parasiticus*; *Bipolaris* spp; *Blastomyces dermatitidis*; *Blumeria graminis*; *Candida albicans*; *Candida glabrata*; *Candida krusei*; *Candida parapsilosis*; *Candida tropicalis*; *Cladosporium cladosporoides*; *Cladosporium herbarium*; *Coccidioides immitis*; *Coccidioides posadasii*; *Colletotrichium trifolii*; *Curvularia lunata*; *Colletotrichium trifolii*; *Cryptococcus neoformans*; *Encephalitozoon cuniculi*; *Epicoccum nigrum*; *Epidermophyton floccosum*; *Exophiala* spp; *Exserohilum rostratum*; *Fusarium graminearium*; *Fusarium solani*; *Fusarium sporotrichoides*; *Histoplasma capsulatum*; *Leptosphaeria nodorum*; *Magnaporthe grisea*; *Microsporum canis*; *Mycosphaerella graminicola*; *Neurospora crassa*; *Paecilomyces lilanicus*; *Paecilomyces varioti*; *Penicillium cluysogenum*; *Phytophthora capsici*; *Phytophthora infestans*; *Plasmopara viticola*; *Pneumocystis jiroveci*; *Puccinia coronata*; *Puccinia graminis*; *Pyricularia oryzae*; *Pythium ultimum*; *Rhizomucor* sp.; *Rhizoctonia solani*; *Rhizomucor* spp.; *Rhizopus* spp.; *Scedosporium apiospermum*; *Scedosporium prolificans*; *Scopulariopsis brevicaulis*; *Trichophyton interdigitale*; *Trichophyton mentagrophytes*; *Trichophyton rubrum*; *Trichosporon asahii*; *Trichosporon beigelii*; and *Ustilago maydis* may also be used in the above assay. Fungi are cultured by standard methods known to those skilled in the art, and MICs determined as above.

MIC Results in mg/L (YAG Medium):

The following MIC results have been banded into grades. Thus, a grade of 1 represents an MIC of greater than 10 mg/L. A grade of 2 represents an MIC of from 1 to 10 mg/L. A grade of 3 represents an MIC of less than 1 mg/L.

| Example Number | A. flavus | A. fumigatus | A. fumigatus 210 | A. niger | A. terreus | A. terreus 49 |
|---|---|---|---|---|---|---|
| 1 | 3 | 3 | 3 | 3 | 3 | 3 |
| 2 | 3 | 3 | 3 | 3 | 3 | 3 |
| 3 | 3 | 3 | 3 | 3 | 3 | 3 |

-continued

| Example Number | A. flavus | A. fumigatus | A. fumigatus 210 | A. niger | A. terreus | A. terreus 49 |
| --- | --- | --- | --- | --- | --- | --- |
| 4 | 3 | 3 | 3 | 3 | 3 | 3 |
| 5 | 3 | 3 | 3 | 3 | 3 | 3 |
| 6 | 1 | 2 | 2 | 1 | 1 | 2 |
| 7 | 3 | 3 | 3 | 3 | 3 | 3 |
| 8 | 3 | 3 | 3 | 2 | 3 | 3 |
| 9 | 3 | 3 | 3 | 3 | 3 | 3 |
| 10 | 3 | 3 | 3 | 3 | 3 | 3 |
| 11 | 1 | 1 | 1 | 1 | 1 | 1 |
| 12 | 1 | 3 | 3 | 3 | 3 | 3 |
| 13 | 3 | 3 | 3 | 3 | 3 | 3 |
| 14 | 2 | 2 | 2 | 2 | 2 | 3 |
| 15 | 3 | 3 | 3 | 3 | 3 | 3 |
| 16 | 3 | 3 | 3 | 3 | 3 | 3 |
| 17 | 3 | 3 | 3 | 3 | 3 | 3 |
| 18 | 3 | 3 | 3 | 3 | 3 | 3 |
| 19 | 3 | 3 | 3 | 3 | 3 | 3 |
| 20 | 3 | 3 | 3 | 3 | 3 | 3 |
| 21 | 3 | 3 | 3 | 3 | 3 | 3 |
| 22 | 3 | 3 | 3 | 3 | 3 | 3 |
| 23 | 3 | 3 | 3 | 3 | 3 | 3 |
| 24 | 3 | 3 | 3 | 3 | 3 | 3 |
| 25 | 1 | 1 | 1 | 1 | 1 | 1 |
| 26 | 2 | 1 | 1 | 1 | 1 | 1 |
| 27 | 3 | 3 | 3 | 3 | 3 | 3 |
| 28 | 3 | 3 | 3 | 3 | 3 | 3 |
| 29 | 1 | 1 | 2 | 1 | 2 | 2 |
| 30 | 3 | 3 | 3 | 3 | 3 | 3 |
| 31 | 3 | 3 | 3 | 3 | 3 | 3 |
| 32 | 3 | 3 | 3 | 3 | 3 | 3 |

MIC Results in mg/L (RPMI Medium):

The following MIC results have been banded into grades as defined above.

| Example Number | A. flavus | A. fumigatus | A. fumigatus 210 | A. niger | A. terreus | A. terreus 49 |
| --- | --- | --- | --- | --- | --- | --- |
| 1 | 3 | 3 | 3 | 3 | 3 | 3 |
| 2 | 3 | 3 | 3 | 3 | 3 | 3 |
| 3 | 3 | 3 | 3 | 3 | 3 | 3 |
| 4 | 3 | 3 | 3 | 3 | 3 | 3 |
| 5 | 3 | 3 | 3 | 3 | 3 | 3 |
| 6 | 1 | 1 | 1 | 1 | 1 | 1 |
| 7 | 3 | 3 | 3 | 3 | 3 | 3 |
| 8 | 2 | 3 | 2 | 2 | 3 | 3 |
| 9 | 3 | 3 | 3 | 3 | 3 | 3 |
| 10 | 3 | 3 | 3 | 3 | 3 | 3 |
| 11 | 1 | 1 | 1 | 1 | 1 | 1 |
| 12 | 1 | 2 | 2 | 2 | 2 | 2 |
| 13 | 3 | 3 | 3 | 3 | 3 | 3 |
| 14 | 1 | 2 | 2 | 2 | 3 | 3 |
| 15 | 3 | 3 | 3 | 3 | 3 | 3 |
| 16 | 3 | 3 | 3 | 3 | 3 | 3 |
| 17 | 3 | 3 | 3 | 3 | 3 | 3 |
| 18 | 3 | 3 | 3 | 3 | 3 | 3 |
| 19 | 3 | 3 | 3 | 3 | 3 | 3 |
| 20 | 3 | 3 | 3 | 3 | 3 | 3 |
| 21 | 3 | 3 | 3 | 3 | 3 | 3 |
| 22 | 3 | 3 | 3 | 3 | 3 | 3 |
| 23 | 3 | 3 | 3 | 3 | 3 | 3 |
| 24 | 2 | 2 | 2 | 2 | 3 | 3 |
| 25 | 1 | 1 | 1 | 1 | 1 | 1 |
| 26 | 1 | 1 | 1 | 1 | 1 | 1 |
| 27 | 3 | 3 | 3 | 3 | 3 | 3 |
| 28 | 3 | 1 | 1 | 3 | 3 | 3 |
| 29 | 1 | 1 | 1 | 2 | 1 | 2 |
| 30 | 3 | 3 | 3 | 3 | 3 | 3 |
| 31 | 3 | 3 | 3 | 3 | 3 | 3 |
| 32 | 2 | 2 | 2 | 3 | 3 | 3 |

The invention claimed is:

1. A tetrahydroindolizine derivative of formula (I), or a pharmaceutically or agriculturally acceptable salt thereof:

(I)

[Chemical structure of formula (I) showing indolizine core with substituents R3, R4, R5, R6, R7, R8, R2, and carbonyl-C(=O)-N(R8)-(A1)n-L1-R1]

wherein:
R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2 or -A2-L3-A3;
A1, A2 and A3 are the same or different and represent C3-C6 cycloalkyl or an unsubstituted or substituted C6-C10 aryl or 5- to 12-membered heterocyclyl group;
L1 represents a bond, a C1-C6 alkylene group in which none, one, two or three —CH$_2$— groups are independently replaced by —O—, —S— or —NR'—, or a 5- to 12-membered heterocyclyl group;
L2 represents —NR'—, —O—, —CO—, —OCO—, —OCONR'R"—, —CONR'R"— or —SO$_2$—;
L3 represents a bond or a C1-C4 alkylene group in which none, one or two —CH$_2$— groups are independently replaced by —O—, —S— or —NR'—;
n represents 0 or 1;
R8 represents hydrogen or C1-C4 alkyl;
R2 represents an unsubstituted or substituted group selected from C6-C10 aryl, a 5- to 12-membered heterocyclyl group, C1-C8 alkyl and C3-C6 cycloalkyl, halogen or a group of formula —B1—B2;
B1 represents an unsubstituted or substituted C6-C10 aryl group;
B2 represents an unsubstituted or substituted C6-C10 aryl or 5- to 12-membered heterocyclyl group;
R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, C1-C8 alkyl, C2-C8 alkenyl, C2-C8 alkynyl, halogen, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R";
R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;
Y represents C1-C8 alkylene, C2-C8 alkenylene or C2-C8 alkynylene;
Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and
R' and R" independently represent hydrogen, C1-C8 alkyl, C2-C8 alkenyl or C2-C8 alkynyl.

2. A compound according to claim 1, wherein n is 1; L1 is an unsubstituted, saturated 5- to 7-membered heterocyclyl group containing at least two nitrogen atoms, a group of formula —(CH$_2$)$_{m+1}$-Het- or a group of formula -Het-(CH$_2$)$_m$-Het-, wherein m is 2 or 3 and each Het may be the same or different and represents —O— or —NR'—, wherein R' is hydrogen or C1-C4 alkyl; and A1 is phenyl or a 5- or 6-membered heterocyclyl group.

3. A compound according to claim 1, wherein A1 is unsubstituted phenyl or unsubstituted pyridinyl, or is a phenyl or pyridinyl group substituted with one group of formula —Y—Z, —Y—X—Z or —Y—X-A4 where Y is an unsubstituted C1-C8 alkylene group, X is an —O—(C2-C3 alkylene) - group, Z is —OR' or —NR'R" where R' and R" are hydrogen or C1-C2 alkyl, and A4 is a 5- or 6-membered heterocyclyl group which is unsubstituted or substituted with one C1-C2 alkyl group.

4. A compound according to claim 1, wherein R1 is a C1-6 alkyl, C2-C6 alkenyl or C2-C6 alkynyl group which is unsubstituted or substituted with 1, 2, or 3 halogen atoms; unsubstituted —SO$_2$(C1-C4 alkyl); or a group -A2, -L2-A2, -L3-A2 or -A2-L3-A3;
L3 is unsubstituted methylene or ethylene;
A2 is C3-C6 cycloalkyl, phenyl or a monocyclic, saturated or unsaturated, 5- or 6-membered heterocyclic group; and
A3 is phenyl or a monocyclic, saturated or unsaturated, 5- or 6-membered heterocyclic group.

5. A compound according to claim 1, wherein R8 is hydrogen.

6. A compound according to claim 1, wherein R2 is phenyl, C1-C4 alkyl, C5 or C6 cycloalkyl or a 5- or 6-membered heterocyclyl group.

7. A compound according to claim 1 which is a tetrahydroindolizinyl derivative of formula (Ia) or a pharmaceutically or agriculturally acceptable salt thereof:

(Ia)

[Chemical structure of formula (Ia) showing tetrahydroindolizine with C(=O)-C(=O)-NH-A1-L1-R1 and R2 substituents]

wherein:
R1 is a C1-6 alkyl, C2-C6 alkenyl or C2-C6 alkynyl group which is unsubstituted or substituted with 1, 2, or 3 halogen atoms; unsubstituted —SO$_2$(C1-C4 alkyl); or a group -A2, -L2-A2, -L3-A2 or -A2-L3-A3;
A1 is unsubstituted phenyl or pyridyl, or is a phenyl or pyridinyl group substituted with one group of formula —Y—Z, —Y—X—Z or —Y—X-A4 where Y is an unsubstituted C1-C8 alkylene group, X is an —O—(C2-C3 alkylene)- group, Z is —OR' or —NR'R" where R' and R" are hydrogen or C1-C2 alkyl, and A4 is a 5- or 6-membered heterocyclyl group which is unsubstituted or substituted with one C1-C2 alkyl group;
A2 is unsubstituted C3-C6 cycloalkyl or a phenyl or a monocyclic, saturated or unsaturated, 5- or 6-membered heterocyclyl group which is unsubstituted or substituted with one, two or three substituents selected from halogen, unsubstituted C1-C4 alkyl, unsubstituted C1-C4 alkoxy or C1-C4 alkoxy which is substituted with —OMe or —OEt;

A3 is phenyl or a monocyclic, saturated or unsaturated, 5- or 6-membered heterocyclyl group which is unsubstituted or substituted with one, two or three substituents selected from halogen, unsubstituted C1-C4 alkyl and unsubstituted C1-C4 alkoxy;

L1 is an unsubstituted, saturated 5- to 7-membered heterocyclyl group containing at least two nitrogen atoms, a group of formula —(CH$_2$)$_{m+1}$-Het- or a group of formula -Het-(CH$_2$)$_m$-Het-, wherein m is 2 or 3 and each Het may be the same or different and represents —O— or —NR'—, wherein R' is hydrogen or C1-C4 alkyl;

L2 is —SO$_2$—;

L3 is unsubstituted methylene; and

R2 is unsubstituted C1-C4 alkyl, unsubstituted phenyl, unsubstituted C5 or C6 cycloalkyl, unsubstituted tetrahydropyranyl or N-methyl-piperidinyl.

8. A method of treating a fungal disease in a subject, wherein the disease is caused by an *Aspergillus* species, which method comprises administering to said subject an effective amount of a compound or pharmaceutically acceptable salt as defined in claim 7.

9. A compound according to claim 1 which is

N-{4-[2-(4,6-Dimethyl-pyridin-2-yloxy)-ethoxy]-phenyl}-2-oxo-2-(2-phenyl-5,6,7,8-tetrahydro-indolizin-3-yl)-acetamide;

N-{4-[4-(4-Methoxy-6-methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-(2-isopropyl-5,6,7,8-tetrahydro-indolizin-3-yl)-2-oxo-acetamide;

2-(2-Cyclohexyl-5,6,7,8-tetrahydro-indolizin-3-yl)-N-{4-[4-(4,6-dimethyl-pyridin-2-yl)-piperazin-1-yl]-phenyl}-2-oxo-acetamide;

2-Oxo-2-(2-phenyl-5,6,7,8-tetrahydro-indolizin-3-yl)-N-[4-(4-pyridin-3-yl-piperazin-1-yl)-phenyl]-acetamide;

2-Oxo-2-(2-phenyl-5,6,7,8-tetrahydro-indolizin-3-yl)-N-{4-[2-(pyridin-2-yloxy)-ethylamino]-phenyl}-acetamide;

N-(4-{4-[4-(2-Methoxy-ethoxy)-6-methyl-pyridin-2-yl]-piperazin-1-yl}-phenyl)-2-oxo-2-(2-phenyl-5,6,7,8-tetrahydro-indolizin-3-yl) -acetamide;

N-[4-({2-[(4,6-Dimethyl-pyridin-2-yl)-methyl-amino]-ethyl}-methyl-amino)-phenyl]-2-oxo-2-(2-phenyl-5,6,7,8-tetrahydro-indolizin-3-yl)-acetamide;

N-{5-[4-(2,2-Dimethyl-propyl)-piperazin-1-yl]-pyridin-2-yl}-2-oxo-2-(2-phenyl-5,6,7,8-tetrahydro-indolizin-3-yl)-acetamide;

N-{4-[4-(4-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(6-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyrimidin-2-yl)-piperazin-1-yl]-phenyl}-2-oxo-2-(2-phenyl-5,6,7,8-tetrahydro-indolizin-3-yl)-acetamide;

N-{6-[4-(2,2-Dimethyl-propyl)-piperazin-1-yl]-pyridin-3-yl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-pyridin-2-yl-piperazin-1-yl)-phenyl]-acetamide;

N-[4-(4-Benzyl-piperazin-1-yl)-phenyl]-2-oxo-2-(2-phenyl-5,6,7,8-tetrahydro-indolizin-3-yl)-acetamide;

N-[4-(4-Isobutyl-piperazin-1-yl)-phenyl]-2-oxo-2-(2-phenyl-5,6,7,8-tetrahydro-indolizin-3-yl)-acetamide;

N-[4-(4-Cyclopropyl-piperazin-1-yl)-phenyl]-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-thiophen-2-ylmethyl-piperazin-1-yl)-phenyl]-acetamide;

N-[4-(4-Furan-2-ylmethyl-piperazin-1-yl)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-[2-tetrahydro-pyran-4-yl)-5,6,7,8-tetrahydro-indolizin-3-yl]-acetamide;

N-{5-[4-(4,6-Dimethyl-pyridin-2-yl)-piperazin-1-yl]-pyridin-2-yl}-2-oxo-2-(2-phenyl-5,6,7,8-tetrahydro-indolizin-3-yl)-acetamide;

N-{6-[4-(4,6-Dimethyl-pyridin-2-yl)-piperazin-1-yl]-pyridin-3-yl}-2-oxo-2-(2-phenyl-5,6,7,8-tetrahydro-indolizin-3-yl)-acetamide;

N-{4-[4-(5-Methyl-pyridin-2-yl)-piperazin-1-yl]-phenyl}-2-oxo-2-(2-phenyl-5,6,7,8-tetrahydro-indolizin-3-yl)-acetamide;

N-{4-[4-(4-Methyl-pyridin-2-yl)-[1,4]diazepan-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-pyridin-2-yl-[1,4]diazepan-1-yl)-phenyl]-acetamide;

N-{4-[4-(6-Methyl-pyridin-2-yl)-[1,4]diazepan-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-propyl-piperazin-1-yl)-phenyl]-acetamide;

N-{4-[4-(3-Methyl-butyl)-piperazin-1-yl]-phenyl}-2-oxo-2-(2-phenyl-5,6,7,8-tetrahydro-indolizin-3-yl)-acetamide;

2-Oxo-2-(2-phenyl-5,6,7,8-tetrahydro-indolizin-3-yl)-N-[4-(4-prop-2-ynyl-piperazin-1-yl)-phenyl]-acetamide;

N-[4-(4-Butyl-piperazin-1-yl)-phenyl]-2-oxo-2-(2-phenyl-5,6,7,8-tetrahydro-indolizin-3-yl)-acetamide;

N-[4-(4-Allyl-piperazin-1-yl)-phenyl]-2-oxo-2-(2-phenyl-5,6,7,8-tetrahydro-indolizin-3-yl)-acetamide;

N-{4-[4-(3-Methyl-but-2-enyl)-piperazin-1-yl]-phenyl}-2-oxo-2-(2-phenyl-5,6,7,8-tetrahydro-indolizin-3-yl)-acetamide;

N-{4-[((E)-4-But-2-enyl)-piperazin-1-yl]-phenyl}-2-oxo-2-(2-phenyl-5,6,7,8-tetrahydro-indolizin-3-yl)-acetamide;

N-{4-[((Z)-4-But-2-enyl)-piperazin-1-yl]-phenyl}-2-oxo-2-(2-phenyl-5,6,7,8-tetrahydro-indolizin-3-yl)-acetamide;

2-(2-Isopropyl-5,6,7,8-tetrahydro-indolizin-3-yl)-N-{4-[4-(2-methyl-allyl)-piperazin-1-yl]-phenyl}-2-oxo-acetamide;

N-{4-[4-(2,2-Dimethyl-propyl)-piperazin-1-yl]-phenyl}-2-(2-isopropyl-5,6,7,8-tetrahydro-indolizin-3-yl)-2-oxo-acetamide;

N-{4-[4-(4,6-Dimethyl-pyridin-2-yl)-[1,4]diazepan-1-yl]-phenyl}-2-(2-isopropyl-5,6,7,8-tetrahydro-indolizin-3-yl)-2-oxo-acetamide;

2-(2-Cyclohexyl-5,6,7,8-tetrahydro-indolizin-3-yl)-N-{4-[4-(2-methyl-allyl)-piperazin-1-yl]-phenyl}-2-oxo-acetamide;

2-(2-Cyclohexyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclohexyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-N-{4-[4-(2-methyl-allyl)-piperazin-1-yl]-phenyl}-2-oxo-acetamide;

2-(2-Cyclopentyl-5,6,7,8-tetrahydro-indolizin-3-yl)-N-{4-[4-(2,2-dimethyl-propyl)-piperazin-1-yl]-phenyl}-2-oxo-acetamide;

2-(2-Cyclopentyl-5,6,7,8-tetrahydro-indolizin-3-yl)-N-{4-[4-(4,6-dimethyl-pyridin-2-yl)-[1,4]diazepan-1-yl]-phenyl}-2-oxo-acetamide;

2-(2-Cyclopentyl-5,6,7,8-tetrahydro-indolizin-3-yl)-2-oxo-N-[4-(4-pyridin-2-yl-piperazin-1-yl)-phenyl]-acetamide;

2-(2-Cyclopentyl-5,6,7,8-tetrahydro-indolizin-3-yl)-N-{4-[4-(4-methyl-pyridin-2-yl)-piperazin-1-yl]-phenyl}-2-oxo-acetamide;

2-(2-Cyclopentyl-5,6,7,8-tetrahydro-indolizin-3-yl)-N-{4-[4-(6-methyl-pyridin-2-yl)-piperazin-1-yl]-phenyl}-2-oxo-acetamide;

2-(2-Cyclopentyl-5,6,7,8-tetrahydro-indolizin-3-yl)-N-{4-[2-(4,6-dimethyl-pyridin-2-yloxy)-ethoxy]-phenyl}-2-oxo-acetamide;

2-(2-Cyclopentyl-5,6,7,8-tetrahydro-indolizin-3-yl)-N-{4-[4-(4-methoxy-6-methyl-pyridin-2-yl)-piperazin-1-yl]-phenyl}-2-oxo-acetamide;

2-(2-Cyclopentyl-5,6,7,8-tetrahydro-indolizin-3-yl)-N-[4-({2-[(4,6-dimethyl-pyridin-2-yl)-methyl-amino]-ethyl}-methyl-amino)-phenyl]-2-oxo-acetamide;

N-[4-({3-[(4,6-Dimethyl-pyridin-2-yl)-methyl-amino]-propyl}-methyl-amino)-phenyl]-2-oxo-2-(2-phenyl-5,6,7,8-tetrahydro-indolizin-3-yl)-acetamide;

N-{4-[4-(2-Methyl-allyl)piperazin-1-yl]-phenyl}-2-oxo-2-(2-phenyl-5,6,7,8-tetrahydro-indolizin-3-yl)-acetamide;

N-{4-[4-(2,2-Dimethyl-propyl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-oxo-2-(2-phenyl-5,6,7,8-tetrahydro-indolizin-3-yl)-acetamide;

2-(2-Cyclopentyl-5,6,7,8-tetrahydro-indolizin-3-yl)-N-{4-[4-(4,6-dimethyl-pyridin-2-yl)-piperazin-1-yl]-phenyl}-2-oxo-acetamide;

N-{4-[4-(4,6-Dimethyl-pyridin-2-yl)-[1,4]diazepan-1-yl]-phenyl}-2-oxo-2-(2-phenyl-5,6,7,8-tetrahydro-indolizin-3-yl)-acetamide; N-{4-[4-(4,6-Dimethyl-pyridin-2-yl)-piperazin-1-yl]-phenyl}-N-methyl-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-phenyl}-2-[2-(1-methyl-piperidin-4-yl)-5,6,7,8-tetrahydro-indolizin-3-yl]-2-oxo-acetamide;

2-Oxo-N-(1-phenyl-piperidin-4-yl)-2-(2-phenyl-5,6,7,8-tetrahydro-indolizin-3-yl)-acetamide;

N-{4-[4-(6-Methoxy-4-methyl-pyridin-2-yl)-piperazin-1-yl]-phenyl}-2-oxo-2-(2-phenyl-5,6,7,8-tetrahydro-indolizin-3-yl)-acetamide;

N-{4-[2-(2,6-Dimethyl-pyridin-4-yloxy)-ethoxy]-phenyl}-2-oxo-2-(2-phenyl-5,6,7,8-tetrahydro-indolizin-3-yl)-acetamide;

N-[4-[4-(6-Ethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4-Ethyl-pyridin-2-yl)-piperazin-1-yl]-phenyl}-2-oxo-2-(2-phenyl-5,6,7,8-tetrahydro-indolizin-3-yl)-acetamide;

N-{4-[4-(5-Morpholin-4-ylmethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methyl-phenyl}-2-oxo-2-(2-phenyl-5,6,7,8-tetrahydro-indolizin-3-yl)-acetamide;

N-[4-(4-Hydroxy-4',6'-dimethyl-3,4,5,6-tetrahydro-2H-[1,2']bipyridinyl-4-yl)-phenyl]-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-2-methoxymethyl-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-[3-(4-methyl-piperazin-1-yl)-propoxymethyl]-phenyl}-2-oxo-2-(2-phenyl-5,6,7,8-tetrahydro-indolizin-3-yl)-acetamide;

N-[4-[4-(4,6-Dimethyl-pyridin-2-yl)-piperazin-1-yl]-3-(3-morpholin-4-yl-propoxymethyl)-phenyl]-2-oxo-2-(2-phenyl-5,6,7,8-tetrahydro-indolizin-3-yl)-acetamide;

N-{3-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-Naphthalen-1-yl-2-oxo-2-(2-phenyl-5,6,7,8-tetrahydro-indolizin-3-yl)-acetamide;

N-{3-(2-Dimethylamino-ethoxymethyl)-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{2-Chloro-4-[4-(4,6-dimethyl-pyridin-2-yl)-piperazin-1-yl]-phenyl}-2-oxo-2-(2-phenyl-5,6,7,8-tetrahydro-indolizin-3-yl)-acetamide;

N-{4-[4-(4,6-Dimethyl-pyridin-2-yl)-piperazin-1-yl]-3-hydroxy-phenyl}-2-oxo-2-(2-phenyl-5,6,7,8-tetrahydro-indolizin-3-yl)-acetamide; and N-(2,3-Dihydro-benzofuran-6-yl)-2-oxo-2-(2-phenyl-5,6,7,8-tetrahydro-indolizin-3-yl)-acetamide.

10. A method of treating a fungal disease in a subject, wherein the disease is caused by an *Aspergillus* species, which method comprises administering to said subject an effective amount of a compound or pharmaceutically acceptable salt as defined in claim 9.

11. A pharmaceutical composition comprising a compound or pharmaceutically acceptable salt as defined in claim 1 and a pharmaceutically acceptable carrier or diluent.

12. A composition comprising a compound or agriculturally acceptable salt as defined in claim 1 and an agriculturally acceptable carrier or diluent.

13. A method of treating a fungal disease in a subject, wherein the disease is caused by an *Aspergillus* species, which method comprises administering to said subject an effective amount of a compound or pharmaceutically acceptable salt as defined in claim 1.

14. A method according to claim 13 wherein the disease is Allergic Bronchopulmonary Aspergillosis (ABPA).

15. A method according to claim 13 wherein the disease is asthma.

16. A method of controlling a fungal disease in a plant, wherein the disease is caused by an *Aspergillus* species, which method comprises applying to the locus of the plant a compound or agriculturally acceptable salt as defined in claim 1.

* * * * *

UNITED STATES PATENT AND TRADEMARK OFFICE
CERTIFICATE OF CORRECTION

PATENT NO. : 8,524,705 B2
APPLICATION NO. : 12/601284
DATED : September 3, 2013
INVENTOR(S) : Payne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this
Twenty-third Day of May, 2017

Michelle K. Lee
*Director of the United States Patent and Trademark Office*